US010571465B2

(12) United States Patent
Szmacinski et al.

(10) Patent No.: US 10,571,465 B2
(45) Date of Patent: Feb. 25, 2020

(54) PLASMONIC SUBSTRATES FOR METAL-ENHANCED FLUORESCENCE BASED SENSING, IMAGING AND ASSAYS FOR CELLS

(71) Applicant: The University of Maryland, Baltimore, Baltimore, MD (US)

(72) Inventors: Henryk Szmacinski, Mariottsville, MD (US); Joseph R. Lakowicz, Ellicott City, MD (US)

(73) Assignee: The University of Maryland, Baltimore, Baltimore, MD (US)

( * ) Notice: Subject to any disclaimer, the term of this patent is extended or adjusted under 35 U.S.C. 154(b) by 690 days.

(21) Appl. No.: 14/965,560

(22) Filed: Dec. 10, 2015

(65) Prior Publication Data

US 2017/0168048 A1    Jun. 15, 2017

(51) Int. Cl.
| | |
|---|---|
| *G01N 33/543* | (2006.01) |
| *G01N 33/553* | (2006.01) |
| *G01N 21/64* | (2006.01) |
| *G01N 21/27* | (2006.01) |

(52) U.S. Cl.
CPC ......... *G01N 33/553* (2013.01); *G01N 21/648* (2013.01); *G01N 21/6408* (2013.01); *G01N 33/54346* (2013.01); *G01N 21/274* (2013.01)

(58) Field of Classification Search
None
See application file for complete search history.

(56) References Cited

U.S. PATENT DOCUMENTS

| | | | | |
|---|---|---|---|---|
| 7,527,939 | B2 | 5/2009 | Davey | |
| 2003/0143641 | A1 | 7/2003 | Brice et al. | |
| 2007/0010488 | A1* | 1/2007 | Youssef | A61K 31/35 514/63 |
| 2007/0178449 | A1 | 8/2007 | Braesch-Andersen | |
| 2008/0305086 | A1* | 12/2008 | Poole | C12N 5/0623 424/93.7 |
| 2009/0309617 | A1* | 12/2009 | Fang | C12Q 1/025 324/692 |
| 2010/0003695 | A1 | 1/2010 | Geddes | |
| 2010/0035335 | A1* | 2/2010 | Lakowicz | G01N 21/648 435/287.1 |
| 2013/0078148 | A1* | 3/2013 | Kaya | G01N 21/648 422/69 |
| 2013/0130301 | A1* | 5/2013 | Yoon | B01L 3/502738 435/30 |
| 2013/0172207 | A1* | 7/2013 | Dai | G01N 33/553 506/9 |
| 2014/0287224 | A1* | 9/2014 | Geddes | G01N 21/6408 428/328 |
| 2015/0247846 | A1 | 9/2015 | Gerion | |
| 2015/0338345 | A1* | 11/2015 | Lakowicz | G01N 33/58 435/5 |
| 2015/0338402 | A1* | 11/2015 | Lakowicz | G01N 33/54373 506/9 |
| 2016/0025744 | A1* | 1/2016 | Feldman | G01N 33/54373 506/9 |
| 2016/0069909 | A1* | 3/2016 | Nakamura | G01N 33/54346 436/501 |
| 2016/0146799 | A1* | 5/2016 | Robinson | G01N 33/54346 506/4 |
| 2016/0355869 | A1* | 12/2016 | Blair | G01N 33/54373 |

OTHER PUBLICATIONS

Kadir Aslan et al., Metal-Enhanced Fluorescence Solution-Based Sensing Platform, Journal of Fluorescence, 2004, pp. 677-679, vol. 14, No. 6, Publisher: Springer Science.
ISA/KR, International Search Report and Written Opinion for the corresponding PCT application PCT/US2012/066451, dated Feb. 26, 2013, pp. 1-12.
Krishanu Ray et al., Metal-enhanced Intrinsic Fluorescence of Proteins on Silver Nanostructured Surfaces towards Label-Free Detection, The Journal of Physical Chemistry C: Nanomaterials and Interfaces, 2008, pp. 17957-17963, vol. 112, No. 46, Publisher: ACS Publications.
Scott M. Tabakman et al., Plasmonic substrates for multiplexed protein microarrays with femtomolar sensitivity and broad dynamic range, Nature Communications, 2011, p. 466 vol. 13, No. 2, Publisher: Nature Publishing Group.
Giakos G., et al, (2002) "Exploitation of Enhanced Fluorescence via Cross-Coupling Principles Toward the Design of an Optical Integrated Thin-Film Sensor for Nanotechnology and Biomedical Applications", IEEE Trans. Instr. Measurem, vol. 51, Issue 5, pp. 970-975. Matveeva E., et al, (2004) "Metal-enhanced fluorescence immunoassays using total internal reflection and silver island-coated surfaces", Anal. Biochem, vol. 334, pp. 303-311.
Matveeva E., et al, (2007) "Metal particle-enhanced fluorescent immunoassays on metal mirrors", Anal. Biochem. vol. 361, pp. 239-245.
Szmacinski H., et al, (2008) "A novel method for monitoring monoclonal antibody production during cell culture", Bioeng. Biotechnol, vol. 100, pp. 448-457.
Szmacinski H., et al, (2010), "Time-resolved fluorometric method for one-step immunoassays using plasmonic nanostructures", J. Phys. Chem. C, vol. 114, pp. 7236-7241.
Tabakman, et al, (2011), "Plasmonic substrates for multiplexed protein microarrays with femtomolar sensitivity and broad dynamic range", Nat. Commun., pp. 1-9.

(Continued)

*Primary Examiner* — Ann Y Lam
(74) *Attorney, Agent, or Firm* — Beusse Wolter Sanks & Maire; Engene J. Molinelli

(57) ABSTRACT

Techniques for metal enhanced fluorescence include determining a calibration curve that relates concentration of a particular analyte to at least one of intensity or lifetime of fluorescent emissions at a plasmonic substrate in response to incident light, for a plurality of known concentrations of the particular analyte mixed with a reagent. The reagent comprises a detection molecule. A concentration of the particular analyte in a vicinity of a cell in a sample is determined directly from the calibration curve and measurements, in response to the incident light, of at least one of intensity or lifetime of fluorescent emissions at the plasmonic substrate in contact with the cell and reagent.

19 Claims, 26 Drawing Sheets

(56) References Cited

OTHER PUBLICATIONS

Zhang J., et al, (2005) "Surface-enhanced fluorescence of fluorescein-labeled oligonucleotides capped on silver nanoparticles", J. Phys. Chem. B vol. 109, pp. 7643-7648.

* cited by examiner

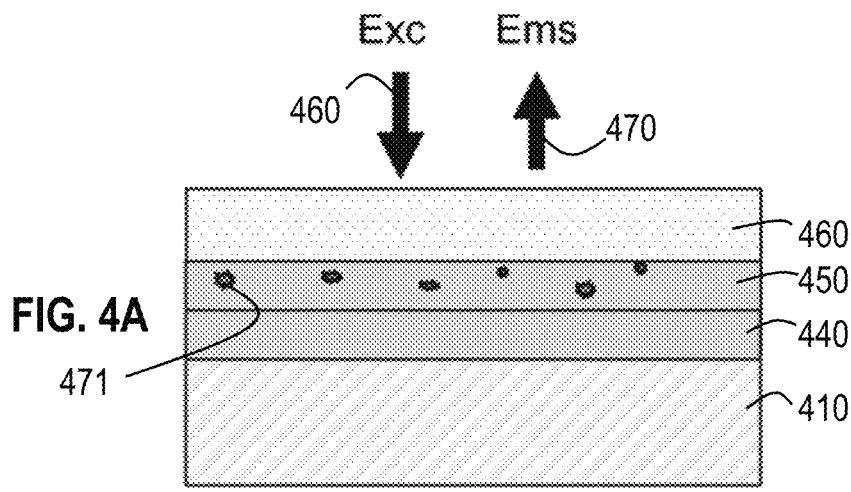
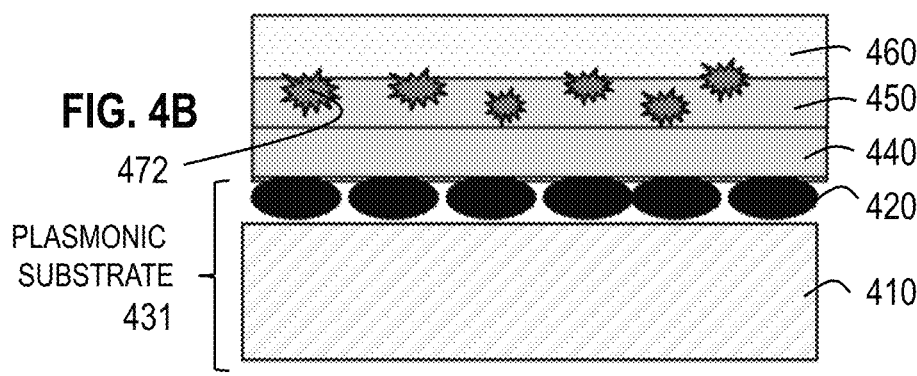
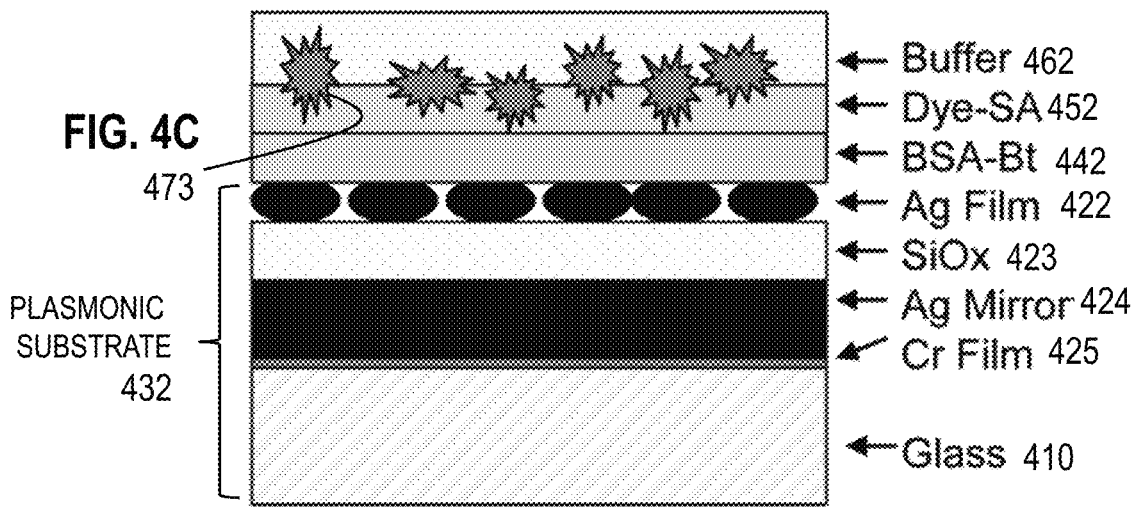

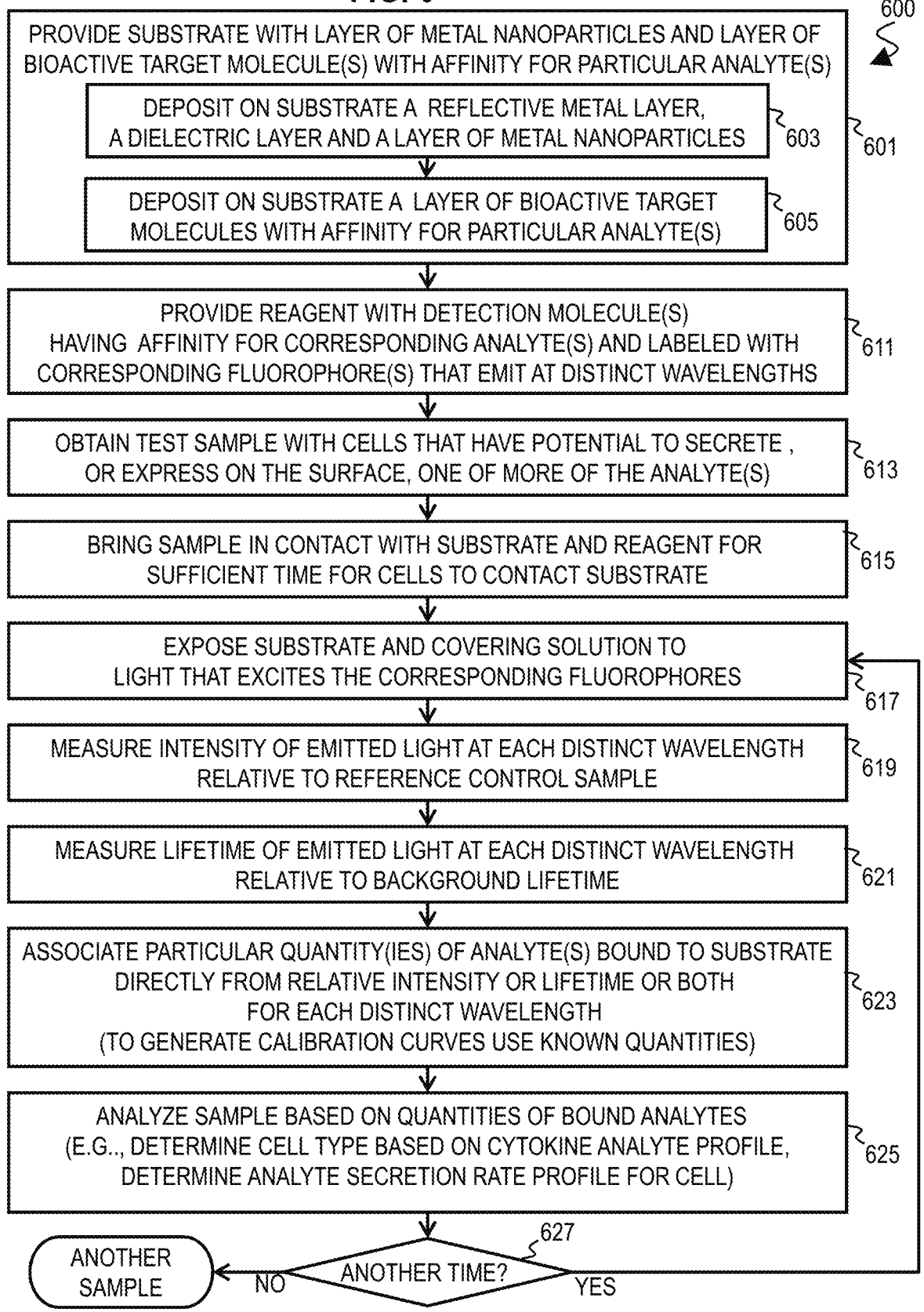

FIG. 8A
FIG. 8B
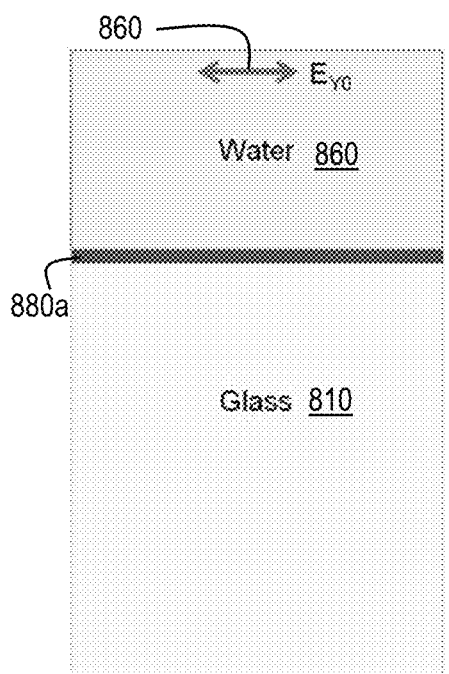
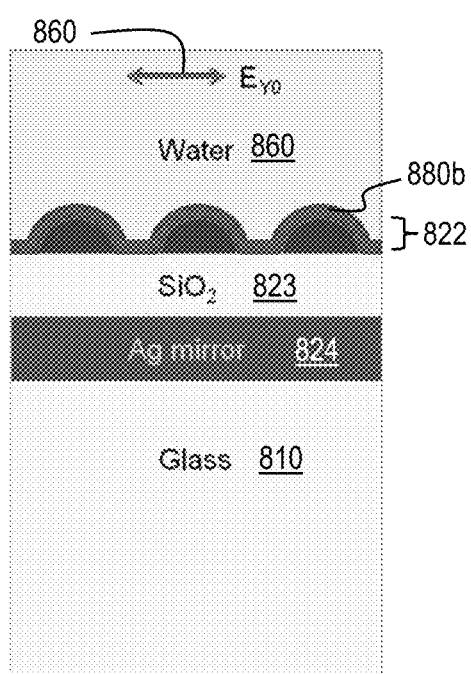

FIG. 16A
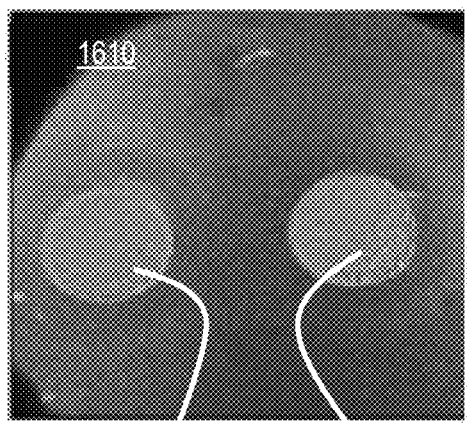
IFNγ 1611    TNFα 1612
FIG. 16B
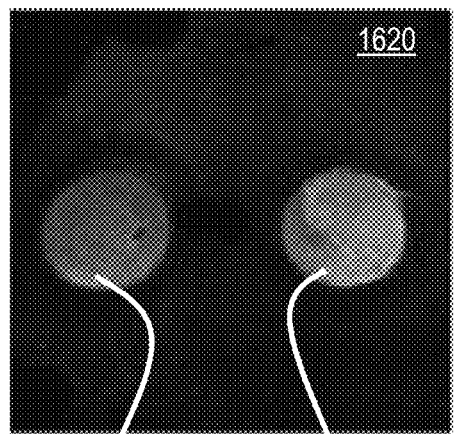
IFNγ 1621    TNFα 1622
FIG. 17A
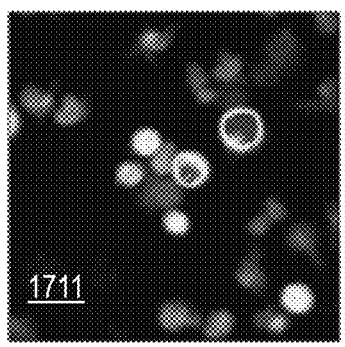
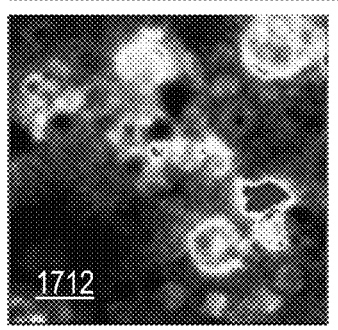
FIG. 17B
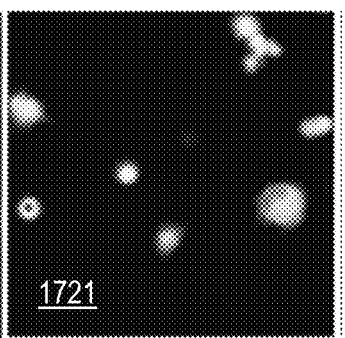
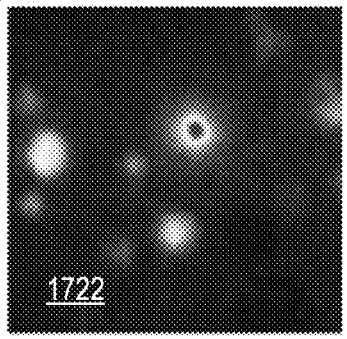
FIG. 17C
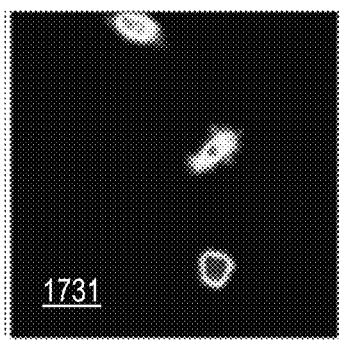
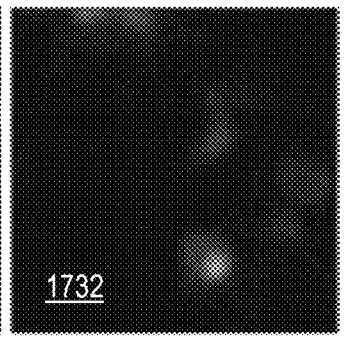

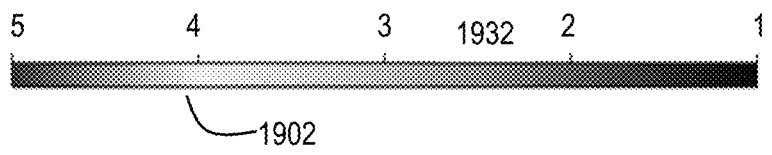

Cells mono cultures

Cells co-culture

PLASMONIC SUBSTRATES FOR METAL-ENHANCED FLUORESCENCE BASED SENSING, IMAGING AND ASSAYS FOR CELLS

CROSS-REFERENCE TO RELATED APPLICATIONS

This application is related to U.S. Utility application Ser. No. 14/359,343 filed May 20, 2014 which claims priority to Patent Cooperation Treaty application PCT/US2012/066451 filed Nov. 23, 2012 which claims priority to Provisional Appln. 61/562,667, filed Nov. 22, 2011, and Provisional Appln. 61/592,851, filed Jan. 31, 2012, and the entire contents of each of which are hereby incorporated by reference as if fully set forth herein, under 35 U.S.C. § 119(e).

BACKGROUND OF THE INVENTION

In affinity assays, a known quantity of a labeled probe competes with or binds to an unknown quantity of unlabeled analyte at binding sites on a target molecule for which the analyte has an affinity. The labeled probe that is bound to the target molecule presents a different measurable phenomenon than the labeled probe that is unbound. Calibration curves relate the presence or quantity of the analyte to the relative amount of bound to unbound labeled probe. The calibration curves are generated by measuring the relative amounts of bound and unbound labeled probe in the presence of known quantities of analyte. In sandwich binding assays, the probe binds to the analyte that is bound to the target molecule. In immunoassays, the analyte is an antigen and the target molecule is an antibody.

Cytokines are important antigens that are secreted by cells to promote a function of the cell. Cytokines control many biological processes including inflammation and disease; therefore, cytokine measurements are widely used in basic research and diagnostics. Cytokines are small regulatory proteins and peptides (with mass in a range from about 8 to about 30 kiloDaltons, kDa, $1\ kDa=10^3$ daltons, 1 dalton=one twelfth of the mass of an unbound neutral atom of carbon-12) that exhibit a wide range of biological activities. Cytokines are released in unique profiles in response to inflammation, infection, systemic infections such as sepsis, chronic wound healing, and even as predictors of mortality.

Affinity assays for cytokines secreted by a cell are especially important but are beset by several challenges. Physiological levels are often low; less than 10 picograms per milliliter (pg/ml, where $1\ pg=10^{-12}$ grams and $1\ ml=10^{-3}$ liters), which corresponds to a range from about 0.5 pico-Molar (pM, $1\ pM=10^{-12}$ Molar, 1 Molar=1 mole per liter) to about 5 pM. The detection of cytokines is also complicated by spatial heterogeneity of their secretion, rapid turnover and short life-time. Many techniques involve the removal, degradation or death of cells that secrete the cytokines, which make it difficult to assess the rate of secretion or the phenotype associated with a cytokine profile.

A majority of cytokine assays developed over the past decade use specific anti-cytokine antibodies. Currently there are two dominant technologies for the measurement of multiple cytokines in biological samples including cell supernatants: multiplex sandwich ELISA and bead-based assays.

One important aspect of biological and clinical studies is finding correlation of cell phenotypes with the profile of cytokines secreted by these cells. Technologies for single cell assay include flow cytometry or intracellular cytokine cytometry (ICC) and ELISPOT.

Flow cytometry is currently mostly used for measurements of cell surface molecules and intracellular levels of cytokines. There are several advantages of flow cytometry: single cell measurement; multiple biomarker detection; and sorting of cell populations for subsequent analysis. There are also several limitations of cytometry: requirement for expensive equipment and trained personnel; inability to measure secreted proteins from live cells; and difficulties in performing analysis with samples of limited cell number. For cytometry, the cell must be permeabilized and treated with secretion inhibitors which, at the very least, interfere with normal cell function.

ELISPOT assays permit the ex vivo identification of cells actively secreting cytokines and can detect a single cell out of a million, based on well-defined spots that clearly represent numbers of cytokine-secreting cells. Several limitations of ELISPOT assays include: no quantitative information on the level of secreted cytokines; difficult multiplexing (even double cytokines is difficult); and, a multi-step protocol that makes ELISPOT usage difficult. To address the need for double cytokine profiling, a fluorometric modification of ELISPOT (FLUOROSPOT) has been reported. However, because of insufficient fluorescence signal, a complex biochemical amplification is needed which is not convenient for practical use. Simultaneous correlation of cell phenotypes (or cell viability) with cytokine secretion is impossible to realize with ELISPOT or standard fluorometric approaches because of the required washing steps that remove the cells before the imaging process.

SUMMARY OF THE INVENTION

The inventors have determined that improved techniques are desirable for measuring rapidly cytokines and other analytes in small quantities, or in the presence of living cells, or directly without rinsing, or some combination. Techniques are provided for plasmonic substrates for metal-enhanced fluorescence based sensing, imaging and assays that alleviate one or more deficiencies of prior art approaches.

In a first set of embodiments, a method includes direct measurement of analytes on a surface of a cell in a sample, even at small concentrations. The method includes providing a plasmonic substrate. The method also includes providing a reagent comprising a detection molecule for the particular analyte. The method further includes determining a calibration curve that relates concentration of the particular analyte to at least one of intensity or lifetime of fluorescent emissions at the plasmonic substrate in response to incident light for a plurality of known concentrations of the particular analyte mixed with the reagent. A sample and the reagent are brought into contact to the plasmonic substrate. Measurements are obtained of at least one of intensity or lifetime of fluorescent emissions at the plasmonic substrate in contact with the sample and reagent in response to the incident light. The method includes determining a concentration of the particular analyte in the sample directly from the calibration curve and the measurements.

For example, in some embodiments of the first set, the sample and reagent are not rinsed from the plasmonic substrate before obtaining the measurements. Furthermore, in some embodiments, the sample comprises a living cell and the analyte is receptor on the surface of the living cell. In still further embodiments, the analyte is a cytokine receptor, chemokine receptor or cluster differentiation protein, or an inhibitory marker, or some combination. In some embodiments, the sample comprises a plurality of different types of living cells and the analyte is a plurality of analytes including a different surface receptor to distinguish each type of living cell of the plurality of different types and at least one secretion from one type of living cell from the plurality of living types.

In a second set of embodiments, an article of manufacture is a plasmonic substrate that includes a layer of metal configured as a mirror to reflect light. The substrate also includes a layer of dielectric material having a thickness greater than about 20 nanometers disposed on the mirror. The substrate still further includes a layer of metal nanoparticles disposed on the layer of dielectric material.

In a third set of embodiments, an article of manufacture is a fluorescence affinity assay kit that includes a plasmonic substrate that comprises a layer of metal nanoparticles affixed to a substrate. The kit still further includes a reagent comprising at least one plurality of substantively identical detection molecules. The detection molecule includes a fluorophore; and, the detection molecule has affinity for the particular analyte. In some embodiments, the kit includes a bioactive target molecule that binds to the plasmonic substrate and a cell receptor that is not an analyte on a cell type of interest.

In other sets of embodiments, an apparatus or a computer-readable not-transitory medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 4A, FIG. 4B, FIG. 4C and FIG. 4D are block diagrams that illustrates an example reference functionalized substrate without a plasmonic substrate and with two example plasmonic substrates, according to multiple embodiments;

FIG. 6 is a flow chart that illustrates an example method to directly assay the quantity of an analyte in a sample without removing the sample, according to an embodiment;

FIG. 8A and FIG. 8B are block diagrams that illustrate example configurations in the vicinity of a substrate for which optical fields are simulated to determine the effects of a dielectric layer on fluorescence enhancement, according to an embodiment;

FIG. 16A and FIG. 16B are images that illustrate example spot quantification of two cytokines with and without washing, according to various embodiments;

FIG. 17A, FIG. 17B and FIG. 17C are images that illustrate example spot quantification of fluorescence in the presence of cells for three concentrations of cells, respectively, according to various embodiments;

DETAILED DESCRIPTION

Figure 1:
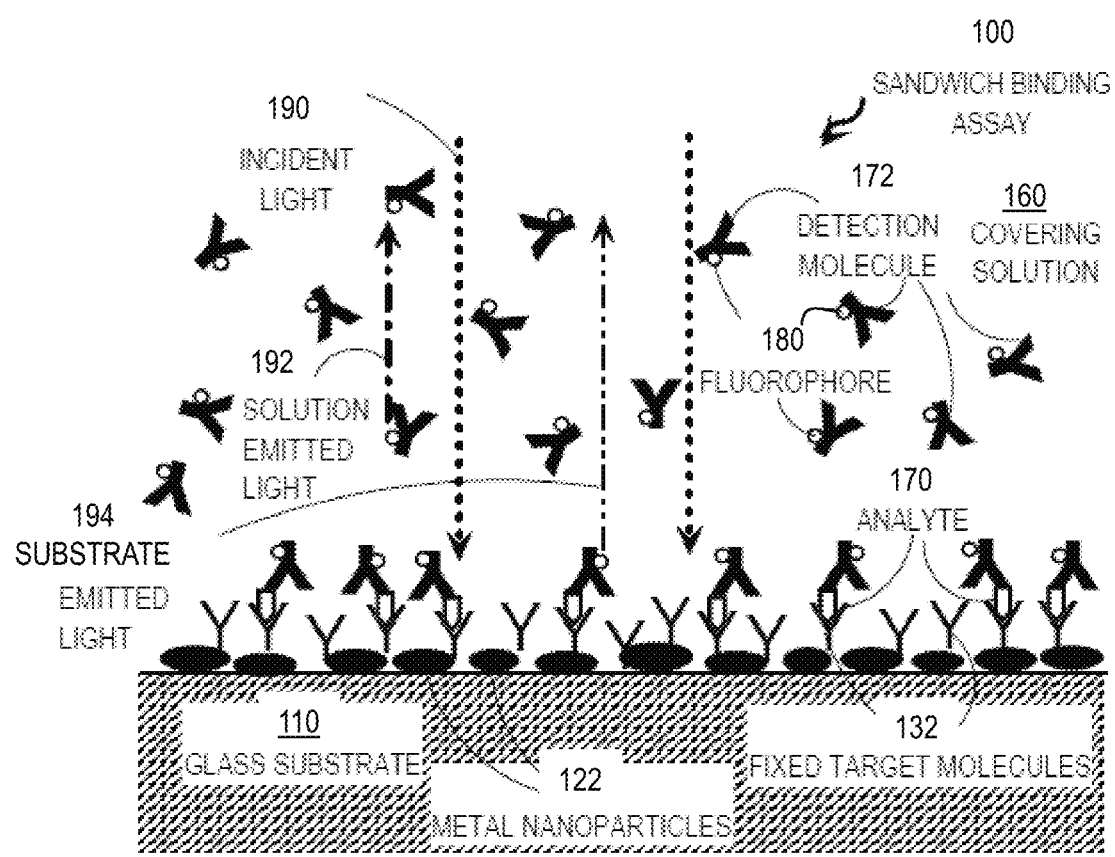
FIG. 1 is a block diagram that illustrates an example sandwich assay, according to an embodiment.

Techniques are described for metal-enhanced fluorescence (MEF) based sensing, imaging and assays. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

The inventors have discovered a surprisingly stable increase in intensity and decrease in lifetime of fluorescent emissions in the presence of metal nanoparticles on a dielectric layer deposited on a metallic mirror. These changes are shown to be related to interactions between the plasmons on the nanoparticles and fluorophores in their vicinity in the presence of excitation and emission waveforms, as described in more detail below. A plasmon is an oscillation of free electron density in a metal particle which can form waves on metal surfaces with the same electric fields and frequencies but shorter wavelengths than electromagnetic waves. Metal surface plasmons with frequencies in the visible spectrum can interact with light. Subsequently, the inventors determined how these properties can be used to design a new family of assays for direct quantification of analytes, such as cytokines, at even very small concentrations, such as associated with cytokine secretion from a single cell, and in real-time.

Some embodiments of the invention are described below in the context of fluorescent immunoassays for cytokines in the presence of silver nanoparticles on a substrate with a silicon dioxide dielectric layer and a silver mirror. However, the invention is not limited to this context. In other embodiments any biological entity may be the analyte and any molecule with analyte affinity may be the target molecule and any metal may be used for the nanoparticles with or without the dielectric layer or mirror or both and the mirror may be made of any metal or other reflective surface. Furthermore, any fluorophore may be used to label a detection molecule used to determine binding of analyte to target molecule.

1. DEFINITIONS

As used in this description, the following terms have the meanings given here.

| | |
|---|---|
| amino acids | An organic molecule comprising both carboxyl and amino groups that can form peptide bonds with complementary groups on other amino acids. 22 amino acids comprise all the proteins found in most living organisms. |
| analyte | a component of a sample for which a quantity is to be determined, including but not limited to a polymer, a ligand, an antigen, an antibody, a protein, a peptide, DNA, RNA, oligonucleotide, a virus or a bacterium. |
| assay | a method to determine the quantity (e.g., the presence, absence, or concentration) of one or more components called analytes in a test sample. |
| assay kit | a collection of materials to be used in an assay. |
| BSA-bt | biotinylated bovine serum albumin, an example target molecule. |
| Cell surface receptor | (also called receptor, cell surface marker or cell marker, herein) a biomolecule expressed on the cell surface, including but not limited to a cytokine receptor, chemokine receptor, cluster of differentiation protein, an antigen, an antibody, another protein or a cell membrane. |
| concentration | a fraction of a sample by weight or volume which is due to a component of the sample. |
| cytokine | A short protein or peptide associated with one or more cell functions or reactions to outside stimulation that serves as one of the signaling molecules used in intercellular communication. |
| detection molecule | a molecule labeled with a fluorophore that is used to detect binding of an analyte to a target molecule by binding to the analyte or by competing with the analyte for binding sites on the target molecule. Also called a probe-fluorophore conjugate or probe-dye conjugate. |
| fluorophore | a functional group in a molecule which absorbs electromagnetic waves at a specific wavelength and subsequently emits electromagnetic waves at a different specific wavelength. Fluorophores include, but are not limited to, fluoresceins, eosin, coumarines, rhodamines, cyanines, benzophenoxazines, phycobiliproteins or fluorescent proteins. |
| functionalized substrate | a substrate that is conditioned to perform a particular function by deposition of layers of one or more types of molecules, such as a glass slide coated with bioactive molecules that facilitate fixing of an analyte or a cell to the substrate. |
| ligand | a functional group in a molecule which binds to a metal, generally involving formal donation of one or more of its electrons. Metal-ligand bindings range from covalent bonds to electrostatic attraction between ions (ionic bonding). |

| | -continued |
|---|---|
| light | electromagnetic (em) waves in a visible portion of the electromagnetic spectrum, which includes wavelengths in air from about 300 to about 800 nanometers (nm, 1 nm = $10^{-9}$ meters). |
| nanoparticles | particles each having a dimension in a size range from about 1 to about 1000 nanometers, nm. 1 nm = $10^{-9}$ meters. |
| plasmon | an oscillation of free electron density in a metal particle which can form waves on metal surfaces with the same electric fields and frequencies but shorter wavelengths than incident electromagnetic waves. Metal surface plasmons with frequencies in the visible spectrum can interact with light. |
| Plasmonic substrate | A substrate that includes a layer of metal nanoparticles that form plasmons with frequencies in a spectral band of one or more fluorophores |
| probe | a molecule that is used to detect binding of an analyte to a target molecule by binding to the analyte or by competing with the analyte for binding sites on the target molecule (the portion of a detection molecule excluding the fluorophore). Probes include, but are not limited to, a polymer, a ligand, an antigen, an antibody, a protein, an oligomer, a protein, a peptide, DNA, RNA or an oligonucleotide. |
| probe-fluorophore conjugate | A detection molecule. |
| protein | A large molecule made up of a long chain of amino acids. Shorter chains of amino acids are called peptides or protein fragments. |
| reagent | substance or compound consumed during a chemical reaction. |
| solution | a liquid mixture. |
| streptavidin-dye conjugate | the protein streptavidin labeled with one or more fluorophores, and thus an example detection molecule. |
| substrate | a material on which a process is conducted |
| target molecule | a molecule which has an affinity for a particular analyte. Target molecules include, but are not limited to, a polymer, a ligand, an antigen, an antibody, a protein, a peptide, DNA, RNA, an oligonucleotide. Also called a capture molecule. |
| test sample | a sample, such as a biological sample, with an unknown quantity of an analyte |

2. OVERVIEW

Sandwich assays using plasmonic substrates are presented that provide unique capabilities suitable for the quantification or temporal monitoring of cytokines and other analytes secreted by living cells or otherwise present in small or temporally changing concentrations. The amplified florescence by plasmonic structures is called metal-enhanced fluorescence (MEF), and occurs when a fluorophore is excited close to the surface of metal particles or nanostructures, typically within a range from about 3 nm to about 50 nm. The amplification of fluorescence is due to an enhanced excitation field (interaction of incident light with nanoparticles), enhanced emissive properties of the fluorophore (increased quantum efficiency of coupled fluorophore plasmon system), and enhanced emission collection (light reflected or directed into a detector). The mechanism of interaction of light with metallic nanostructures is well understood and many experimental and theoretical works have been published, including their applications to biotechnology. Other previous approaches explored individual metallic particles for biosensing applications.

The inventors recognized that the geometrical configuration of MEF is ideal for construction of surface-based bioassays where the transduction signal originates from changes in the location of a dye-labeled biomolecule. Binding of a dye-labeled antibody to the surface-captured antigen will result in a dramatic increase in intensity and decrease in fluorescence lifetime due to the MEF. Thus, detection sensitivity of a typical sandwich-type immunoassay can be improved proportionally to the amplified fluorescence. This leads, in some embodiments, to direct readout without need for rinsing off a reagent or sample.

In some embodiments, a MEFspot method involves the use of plasmonic substrates that optically amplify a signal from surface-bound fluorescent probes resulting in the ability to image intensity and/or lifetime changes. The substantial improvements over conventional approaches are substantially simplified biochemical procedures and new capabilities. The simplified procedure includes a one-step assay and the ability to use live cells with detection sensitivity of ELISA and ELISPOT. New capabilities include real-time monitoring of secreted proteins by cells, their direct quantification, and multiplexing. In addition, the MEFspot method provides the opportunity for detailed studies of selected live cells (or cell clusters) using standard fluorescence microscopy. The method has transformative potential in that that new approaches can be undertaken for studies of cellular function in a heterogeneous cell population, for example by selection of relevant spots (cells) and their detailed studies in environments that closely mimic their natural biological environments. Abilities of MEFspot for detailed cellular studies can lead to better understanding the pathways and mechanisms that underpin cytokine release in broad range of cells.

In some embodiments, MEFspot is used with Fluorescence Lifetime Imaging Microscopy (FLIM), which provides a broad range of image processing with simple visualization of cell function processes which can elucidate cellular mechanisms underlying cancer initiation and progression as well as information about other diseases. Such disciplines as cell physiology, immunology, and cancer research are examples where the MEFspot could substantially facilitate research and provide significant, transformative scientific advancements. These advantages substantially broaden and increase sensitivity compared to traditional cytokine measurements.

FIG. 1 is a block diagram that illustrates an example sandwich assay, according to an embodiment. FIG. 1 depicts a portion of a functionalized substrate, including a glass substrate 110 and metal nanoparticles 122. The functionalized substrate also includes fixed target molecules 132 for a particular analyte as the fixed bioactive molecules. The functionalized substrate is in contact with a covering solution 160.

In typical sandwich assays, the covering solution 160 is a result of a three step process. First the functionalized substrate is contacted to a test sample that includes analyte molecules 170 that are not labeled with a fluorophore. The contact is maintained for sufficient time under conditions that allow the amount of analyte binding to the fixed target molecules 132 to be proportional to the amount of analyte in the test sample. Such times and conditions are easily determined by routine experimentation. Next, the functionalized substrate is washed to remove excess unbound analyte from the test sample. Then the functionalized substrate with bound analyte is contacted to a solution of reagent. The reagent includes detection molecules 172. Each detection molecule 172 includes a fluorophore 180 and a molecule that binds to the analyte 170 at a site on the analyte different from the site that binds the analyte to the fixed target molecule 132. In some embodiments, the reagent is also rinsed and a neutral rinsing buffer solution remains as the covering solution. The combination of the functionalized substrata, sandwiched analyte and covering solution in steady state is called a product of the assay.

The product of the assay is exposed to excitation electromagnetic waves at a specific wavelength that excites fluorescence of the fluorophore 180. In the illustrated example, the functionalized substrate and covering solution are exposed to excitation incident light 190 indicated by dotted arrows. The fluorophores in the detection molecules are excited by the incident light and fluoresce, emitting light at a different specific wavelength. The fluorophores on detection molecules that are free in cover solution 160 emit electromagnetic waves with particular properties. For example, a detection molecule in solution emits solution emitted light 192 indicated by a single dot dash arrow. The collection of these emissions has a first property value which is associated with the particular detection molecule. In contrast, the fluorophores on detection molecules that are bound to the analyte that is in turn bound to the fixed target molecules 132 emit electromagnetic waves with a different value of some property due to metal enhanced fluorescence (MEF). For example, detection molecules bound to analytes bound to fixed target molecules 132 emit substrate emitted light 194 indicated by a double dot dash arrow. For the sandwich assay to function successfully without rinsing the reagent, the collection of these emissions has an optical property value substantially different from the value of a collection of the solution emitted light 192. For example, the presence of nanoparticles 122 causes a change in lifetime or intensity of the substrate emitted light 194 compared to the solution emitted light 192, as described in more detail below.

Figure 3:
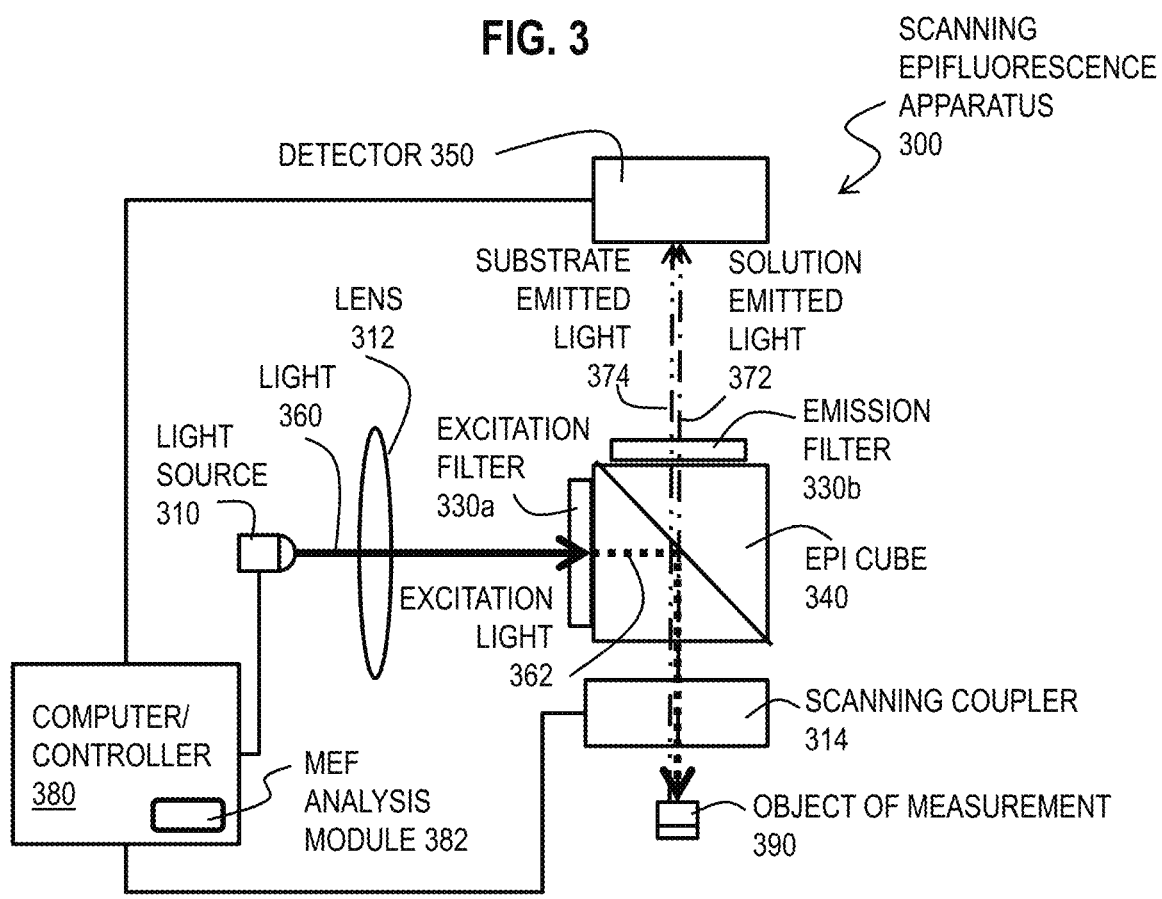
FIG. 3 is a block diagram that illustrates an example fluorescence measurement apparatus suitable for sensing or imaging fluorescence such as for an assay upon which an embodiment of the invention may be implemented.

One or more optical properties of the mixed solution and substrate emitted light are measured using an apparatus like apparatus 300 depicted in FIG. 3. The object 390 is the product of the assay, i.e., the functionalized substrate contacting the covering solution 160. A calibration curve is used in some embodiments to determine the ratio of bound to free detection molecules for a measured value of one or more optical properties. Other calibration curves, as is well known in the art, are used to determine a resulting analyte associated with such a ratio of bound to free detection molecules. The resulting analyte is used to determine the quantity (e.g., the presence, absence or concentration) of analyte in the test sample.

Figure 2:
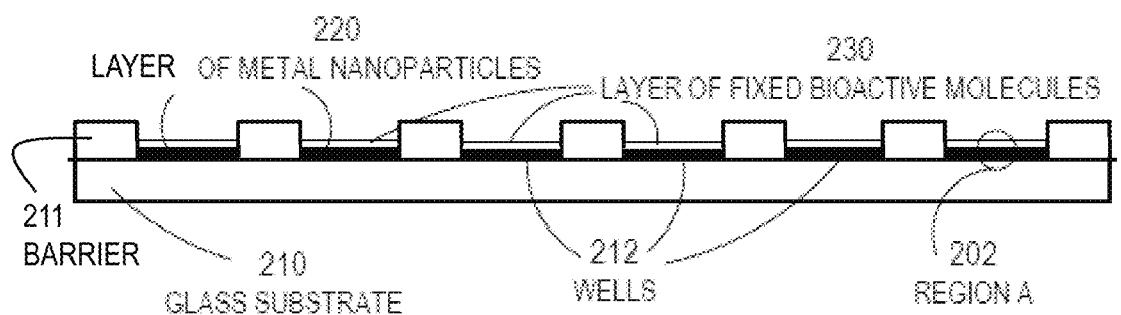
FIG. 2 is a block diagram that illustrates an example glass slide with multiple wells each containing a functionalized substrate that includes a plasmonic substrate, according to an embodiment.

FIG. 2 is a block diagram that illustrates an example glass slide with multiple wells each containing a functionalized substrate that includes a plasmonic substrate, according to an embodiment. The substrate includes a glass substrate 210, with several wells 212 formed by the application of an array of barriers 211 in the illustrated embodiment, but which may be etched in the glass in other embodiments. The wells are used for separating reactions on different portions of the substrate. Deposited in the wells is a layer (often called a film) 220 of metal nanoparticles. Deposited on the film of metal nanoparticles is a layer 230 of bioactive molecules. In some embodiments, there are no wells and the entire glass substrate is coated uniformly with a film 220 of metal nanoparticles and layer 230 of fixed bioactive molecules.

Any material which does not unduly interact with test samples, analytes, detection molecules or target molecules may be used as a substrate. For example glass, quartz and plastic are used as substrate in some embodiments. Substrates can be organic or inorganic.

Any noble metal may be deposited. In various embodiments, the film 220 of metal nanoparticles is one or more silver island films (SIFs) deposited as described below or films of one or more other metal nanoparticles such as gold, copper and aluminum.

Any method may be used to deposit the film of metal nanoparticles 220. For example, the metal nanoparticles may be deposited using a wet chemical deposition method to coat the substrate 210 with the SIFs. In other embodiments, other methods are used to deposit the metal nanoparticles, such as thermal vapor deposition or deposition by sputtering, or patterning using electron beam lithography. In some embodiments, an uneven film is converted to more discrete particles, e.g., by annealing as described in more detail below.

Any distribution of nanoparticle sizes may be deposited. In a preferred embodiment, the nanoparticle sizes include a large number in a size range that is small compared to the wavelengths of fluorescent emissions from a particular fluorophore or a particular set of one or more fluorophores to be used with the substrate. In an example embodiment, the nanoparticles are deposited in a dense configuration to reduce the area of voids where MEF does not occur. The void dimensions are preferably small compared to a maximum distance for effective MEF, such as 50 nm or less. In embodiments that use a mirror, as described in more detail below, it is desirable that some incident light be allowed to reach the mirror and be reflected. In such embodiments the nanoparticles are preferably formed to have an optical density in a range from about 0.2 to about 1.0, preferably about 1.0 (e.g., allow at least 10% of the incident light to pass into the layer below the nanoparticles.

Any molecule may be deposited in the bioactive molecule layer 230. The properties of the functionalized substrate are affected by the bioactive molecule deposited in layer 230. The molecule should include a functional group to affix the molecule to the substrate or metal film, such as a ligand to affix the molecule to a metal nanoparticle. The molecule should also be able to bind to a particular analyte of interest. Such a molecule is also called a target molecule for an assay for the analyte. In illustrated embodiments, all the molecules deposited in the layer 230 are substantively identical. In other embodiments, functionalized substrates are designed for multiple analytes and multiple populations of different target molecules are used in the same well for corresponding different analytes. Binding events of the different analytes would be marked by fluorophores in corresponding different detection molecules emitting at different optical wavelengths. In various embodiments, target molecules that are deposited in the layer 230 include, but are not limited to a polymer, a ligand, an antigen, an antibody, a protein, a peptide, DNA, RNA, or an oligonucleotide.

The functionalized substrate may be designed for any analyte to bind to an appropriately chosen target molecule. In various embodiments, the analyte includes, but is not limited to, a polymer, a ligand, an antigen, an antibody, a protein, a peptide, DNA, RNA, any form of RNA, an oligonucleotide, a virus, a bacterium or a cell.

Region A 202 in a well 212 of the functionalized substrate 200 is indicated in FIG. 2 as an example portion of the substrate 210, film 220 and layer 230, e.g., as depicted in FIG. 1 and FIG. 4.

FIG. 3 is a block diagram that illustrates an example fluorescence measurement apparatus suitable for sensing or imaging fluorescence such as for an assay upon which an embodiment of the invention may be implemented. The apparatus 300 is called a epifluorescence measurement apparatus and is suitable for MEF affinity assays. Apparatus 300 includes light source 310, such as a light emitting diode (LED), lens 312, filters 330a and 330b, Epi cube 340 and detector 350, such as a photo-multiplier tube (PMT) or a charge-coupled device (CCD). In some embodiments a scanning coupler 314 is included to obtain imagery data, e.g., in a FLIM device. In other embodiments, a single measure is made of the well; and, scanning coupler 314 is replaced with a simple coupler, such as another lens. A computer controller 380, such as the computer depicted in FIG. 23 or the chipset depicted in FIG. 24, is included to control the operation of light source 310, scanning coupler 314, if any, and to collect measurements from detector 350. The MEF analysis module 382 performs one or more of the processes for analyzing the data from a plasmonic substrate, such as determining calibration curves and converting intensities and lifetimes to concentrations of one or more analytes, as described in more detail below.

Although an object of measurement 390 is depicted in FIG. 3, the object 390 is not part of apparatus 300, but is operated upon by apparatus 300. In some embodiments, the object 390 is a product formed during an assay described below. During the experimental measurements described below, object 390 is prepared in accordance with one of the assays. Also depicted in FIG. 3 are light beams produced during operation of the apparatus 300, including light source light 360, filtered excitation light 362, solution emitted light 372 and substrate emitted light 374.

Light from LED 310 is collimated with lens 312a, directed through excitation bandpass filter 330a, dichroic splitter in Epi cube 340, and scanning optical coupler 314 (such as a rotating polygonal mirror) to scan the object 390. The fluorescent light emitted from the object 390 is passed through coupler 314, Epi cube 340, and emission filter 330b, and is collected at detector 350.

Lifetimes were determined, e.g., in module 382, using one- or two-exponential models fit to the observations. These models are represented by Equation 1.

$$I(t) = \Sigma_i \alpha i \exp(-t/\tau i) \tag{1}$$

where I is intensity at time t, i indicates an ith component of several exponential components, exp is the exponential function in which the base e is raised to the value of the argument inside parentheses, $\alpha i$ is amplitude of the ith component and $\tau i$ is the lifetime of the ith component at which time the component falls to 1/e of its value at time t=0. The number of components used is increased until a good fit is obtained for the data. Amplitude weighted lifetimes $<\tau>$ are defined by Equation 2a.

$$<\tau> = \Sigma_i \alpha i * \tau i \tag{2a}$$

Intensity weighted lifetimes, $\tau_M$, are defined by Equation 2b.

$$\tau_M = \Sigma_i f i * \tau i \tag{2b}$$

Where fi is the fractional intensity defined by Equation 2c $$fi = \alpha i * \tau i / \Sigma_i \alpha i * \tau i \tag{2c}$$

The spectroscopic properties of various streptavidin-dye conjugates in buffer solution are summarized in Table 1 for ten fluorophores that could simultaneously label ten different analytes. In other embodiments, more or fewer fluorophores are used. Dye to protein ratio (D/P) varied from about 1.0 to 3.9. Higher D/P ratios than 4 usually lead to the self quenching and depolarization effects. The spectral range of these fluorophores span a wide range of wavelengths from about 495 nm to about 675 nm. The extinction coefficient $\epsilon$ is a physical property of the conjugate in solution, is expressed in units of inverse Mole centimeters ($M^{-1}$ $cm^{-1}$, where 1 cm=$10^{-2}$ meters) and is akin to an optical cross section for interactions with an incident beam. The wavelengths of maximum absorption ($\lambda_{ABS}$) and the wavelength of maximum emission ($\lambda_{EMS}$) are given in nanometers. Intensity weighted lifetime and amplitude weighted lifetime are given in nanoseconds (ns, 1 ns=$10^{-9}$ seconds).

TABLE 1

Spectral properties of streptavidin-daye conjugates in solution

| Dye | D/P | ε | $\lambda_{ABS}/\lambda_{EMS}$ | $\tau_i$ (ns) | $\alpha_i$ | $f_1$ | $<\tau>$ | $\tau_M$ |
|---|---|---|---|---|---|---|---|---|
| Fluorescein-Bt | N/A | 68,000 | 494/518 | 4.11 | 1.0 | 1.0 | 4.11 | 4.11 |
| AlexaFluor 488 | 3.9 | 71,000 | 495/519 | 3.08 | 0.4778 | 0.7382 | 1.759 | 2.418 |
|  |  |  |  | 0.55 | 0.5222 | 0.2618 |  |  |
| DY495 | 1.0 | 70,000 | 495/520 | 3.91 | 0.4519 | 0.7991 | 2.211 | 3.287 |
|  |  |  |  | 0.81 | 0.5481 | 0.2009 |  |  |
| AlexaFluor 532 | 4.1 | 81,000 | 529/551 | 2.60 | 0.1530 | 0.4968 | 0.804 | 1.533 |
|  |  |  |  | 0.48 | 0.8470 | 0.5032 |  |  |
| DY547 | 1.0 | 150,000 | 553/572 | 3.76 | 0.0159 | 0.1926 | 0.316 | 0.934 |
|  |  |  |  | 0.26 | 0.9841 | 0.8074 |  |  |
| Cy 3 | 1.7 | 150,000 | 558/578 | 1.23 | 0.3145 | 0.6684 | 0.579 | 0.915 |
|  |  |  |  | 0.28 | 0.6855 | 0.3316 |  |  |
| AlexaFluor 635 | 1.5 | 140,000 | 632/647 | 4.88 | 0.3977 | 0.4681 | 3.995 | 4.037 |
|  |  |  |  | 3.41 | 0.6023 | 0.5139 |  |  |

TABLE 1-continued

Spectral properties of streptavidin-daye conjugates in solution

| Dye | D/P | ε | $\lambda_{ABS}/\lambda_{EMS}$ | $\tau_i$ (ns) | Intensity Decays $\alpha_i$ | $f_1$ | $<\tau>$ | $\tau_M$ |
|---|---|---|---|---|---|---|---|---|
| AlexaFluor 647 | 2.7 | 239,000 | 653/669 | 2.11 | 0.6260 | 0.4447 | 1.485 | 1.183 |
|  |  |  |  | 0.44 | 0.3740 | 0.5553 |  |  |
| Cy 5 | 0.9 | 250,000 | 657/678 | 1.86 | 1.0 | 1.0 | 1.86 | 1.86 |
| AlexaFluor 680 | 2.8 | 184,000 | 679/675 | 1.98 | 1.0 | 1.0 | 1.98 | 1.98 |

Although processes, equipment, and data structures are depicted in FIG. 3 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Figure 4D:
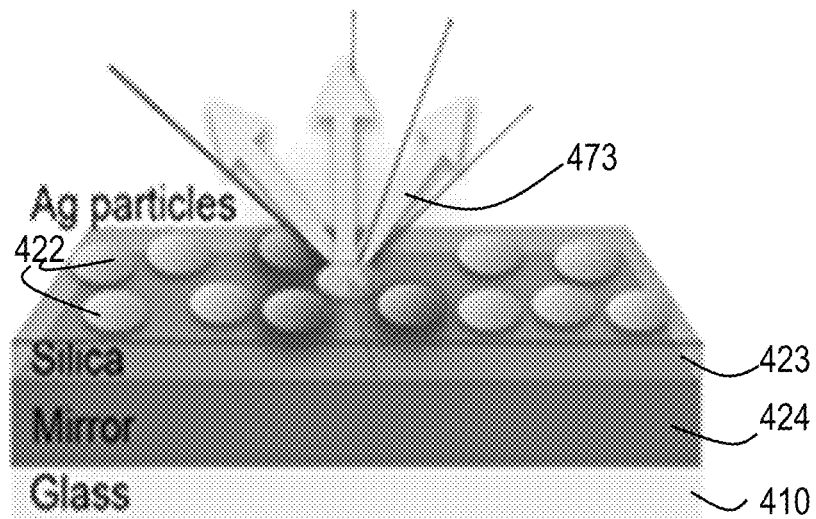

FIG. 4A, FIG. 4B, FIG. 4C and FIG. 4D are block diagrams that illustrate an example reference functionalized substrate without a plasmonic substrate and other functionalized substrates with two example plasmonic substrates, respectively, according to multiple embodiments. FIG. 4A is a block diagram that illustrates an example sandwich assay without a plasmonic substrate. A plasmonic substrate is one that includes metal nanoparticles that produce plasmons in response to excitation or emission light used in a fluorescent assay. In this example a glass substrate 410 supports a layer 440 of fixed bioactive target molecules that have affinity for an analyte. Deposited next is a layer 450 of the detection molecule with fluorophores that have bound to any analyte that binds to the target molecules in layer 440. The fluorophores in this layer fluoresce in the response to excitation light with a frequency of occurrence (and thus measured intensity) that depends on the number of fluorophores bound to the analytes that are bound to the layer of target molecules. This frequency of occurrence is related to the concentration of the analyte in the sample fluid which has since been washed away. The fluorescent output of each fluorophore is indicated by a flash 471. Above the layer 450 is a layer 460 of a covering solution, such as a buffer applied during the last rinse.

FIG. 4B is a block diagram that illustrates an example sandwich assay with a plasmonic substrate. Layers 410, 440, 450 and 460 are as described above. Layer 420 of metal nanoparticles on glass substrate 410 produces a plasmonic substrate 431. The proximity of the plasmonic substrate to the fluorophores in layer 450 of the bound detection molecules causes an increase of the fluorescent emissions from each fluorophore as indicated by the larger flashes 472. In general, the influence of plasmons induced in plasmonic substrate 431 on the intensity of emission from the fluorophores in layer 440 depends on the distance from layer 450 to layer 420 being on the order of about 3 to 50 nanometers. This distance can be assured by a proper choice of sizes and binding sites for the target molecules in layer 440 and the detection molecules in layer 450 and the added distance of the analyte sandwiched on the interface of those two layers. The combination of a plasmonic substrate, such as substrate 431, and the layer 440 of fixed target molecules is called the functionalized substrate hereinafter. The fluorescent output of each fluorophore is indicated by a flash 472, that is substantially greater than the output 471 without a plasmonic substrate.

FIG. 4C is a block diagram that illustrates an example sandwich assay with a superior plasmonic substrate 432, according to some example embodiments. The plasmonic substrate 432 includes, between the glass 410 and a layer of metal nanoparticles, a mirror, such as silver (Ag) mirror 424 and a dielectric layer, e.g., silicon oxide (SiOx) layer 423. In some embodiments, the dielectric layer may comprise silicon monoxide or silicon dioxide. In an experimental embodiment illustrated, the layer of metal nanoparticles is a layer 422 of silver film formed of silver nanoparticles, as described in more detail below. In some embodiments, the layer of nanoparticles includes any metal including, for example, silver, gold, or aluminum, as particles or a film with undulating surface. In various embodiments, the metallic mirror layer is constructed of any metal, such as silver, gold, or aluminum. In the illustrated embodiment, the Ag mirror is fixed to the glass substrate 410 by an adhesive layer, e.g., layer 425 of Chromium (Cr) film. In other embodiments, the adhesive layer may consist of any non-metallic material that will prevent slipping between the base layer and the metallic mirror layer, such as titanium oxide or silicon nitride. In the experimental embodiment, the layer 460 of supernatant fluid is a layer 462 of a buffer solution, such as phosphate buffer saline (PBS). In this embodiment, the detection molecule layer 450 is a layer 452 of dye-streptavidin conjugate (Dye-SA) bound to the analyte that binds to the target molecule layer (where the dye is one of the fluorophores in Table 1). Also, in this embodiment, the fixed target molecule layer 440 is a layer 442 of biotinylated bovine serum albumin (BSA-Bt). The fluorescent output of each fluorophore is indicated by a flash 473 that is substantially greater than the output 472 from the plasmonic substrate of FIG. 4B or the output 471 without a plasmonic substrate. FIG. 4D is a block diagram that illustrates an example perspective view of a small portion of a plasmonic substrate, according to an embodiment. The layers 422, 423, 424 and 410 are as described above for FIG. 4C. The enhanced far field fluorescent emissions are represented by the yellow arrows that correspond to flashes 473.

For the substrates with Ag nanoparticles on the glass as depicted in FIG. 4B, it was found that excitation and observation at the other side of the glass (opposite to the protein-fluorophore layers) resulted in fluorescence signals comparable to those for direct excitation/observation conditions. This implies that for direct excitation/emission configuration, a significant amount of fluorescence is coupled into a glass substrate and radiated in the opposite direction to the detector. This is because the under layer of glass has a higher permittivity than the aqueous solution above the silver nanostructures, and highly efficient coupling of fluorescence occurs into the glass substrate 410. Therefore, inventors determined to include a proper mirror and layer of dielectric to redirect the scattered light toward the observation path. The scattered light trapped in dielectric layer is reflected by the mirror which efficiently increases the excitation and redirect fluorescence into the observation path. The process of reflections within a dielectric layer will occur multiple times since the outer layer of silver nanostructures is semitransparent.

This configuration of layers was found to have a surprisingly large enhancement of fluorescent far field emission intensity (up to about 200-fold), indicated by the much larger flashes 473. Associated with this surprising enhancement is a commensurate surprising decrease in fluorescence lifetime. Decreases in lifetime associated with increases in emission intensity are characteristic of plasmon-fluorophore interactions.

The inventors recognized that such increases in intensity and decreases in lifetime as depicted in FIG. 4B and FIG. 4C made it easy to distinguish fluorophores in solution from those bound in the vicinity of the layer of metal nanoparticles, and direct measurements are enabled in some assay embodiments so that there is no need to rinse either the sample with analyte or the reagent with detection molecules from the covering solution above the functionalized substrate.

Figure 5:
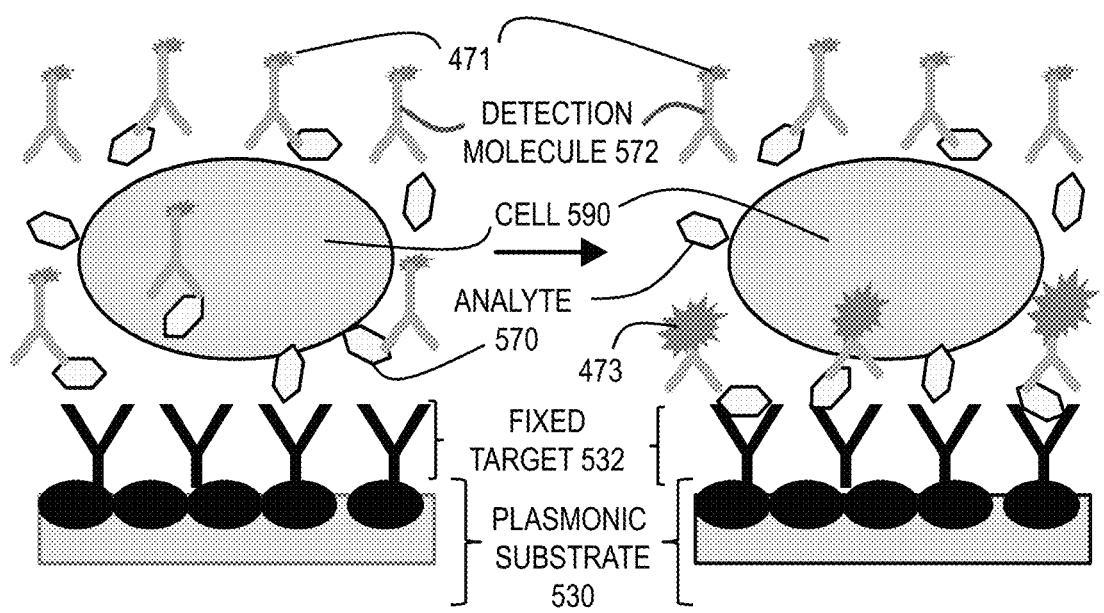
FIG. 5 is a block diagram that illustrates an example measurement of quantity of analytes from a single cell, according to an embodiment.

This ability to provide direct measurements without rinsing away a sample fluid has great advantages for detection and analysis of secretions, such as cytokines, from cells. FIG. 5 is a block diagram that illustrates an example measurement of quantity of analytes from a single cell, according to an embodiment. A plasmonic substrate 530 (such as plasmonic substrate 431 of FIG. 4B or plasmonic substrate 432 of FIG. 4C) supports a layer 532 of fixed target molecules. A cell 590 secretes analytes 570 (such as one or more different cytokines). These analytes bind to the detecting molecules 572, either in solution or bound to the fixed target molecules 532. The unbound detection molecules fluoresce with un-enhanced intensity and non-shortened lifetimes indicated by small flashes 471, while, at least after a time (indicated by the horizontal arrow pointing to the right), the detection molecules bind to the target molecules via secreted protein (analyte) and fluoresce with enhanced intensity and shortened lifetimes indicated by large flashes 473. Upon binding a spot with increased intensity and decreased lifetime is formed. The distinction can be observed even without rinsing the reagent with detection molecules 572, or the sample with cell 590, from the covering solution. With the surprisingly enhanced emissions of 473, even low levels of an analyte can be detected, such as is the case with cytokines secreted from a single cell. The change in enhanced emission or lifetimes over time can be monitored as the cell continues to live in the sample during the measurements. This capability is not believed to be present in the prior art approaches.

FIG. 6 is a flow chart that illustrates an example method to directly assay the quantity of an analyte in a sample without removing the sample, according to an embodiment. Although steps are depicted in FIG. 6 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. For example, in some embodiments, one or more rinsing steps are added.

In step 601, a functionalized substrate is provided. In an illustrated embodiment, the functionalized substrate includes a plasmonic substrate with a layer of metal nanoparticles that are smaller than wavelengths emitted from a particular set of one or more fluorophores to be used in an assay. In this embodiment, the functionalized substrate also includes a layer of one or more populations of substantively identical bioactive target molecules that bind to a particular analyte of interest for corresponding one or more analytes of interest. In some embodiments, the target molecules for different analytes are in separate wells. In other embodiments, target molecules for two or more analytes are included in the same well, either intermixed or segregated.

The functionalized substrate can be provided in any manner. For example, in some embodiments, the substrate is obtained (e.g., from a commercial supplier) with both the metal nanoparticles and layer of bioactive molecule. In some embodiments, the substrate is obtained with the metal nanoparticles already deposited but without the bioactive layer, and the bioactive layer is deposited during step 605. In some of these embodiments the bioactive molecule is supplied and shipped in a separate container (e.g., to preserve its efficacy) as part of an assay kit, and deposited during step 605 to form the functionalized substrate when desired for use. In some other embodiments, the substrate is obtained with neither the metal nanoparticles nor the bioactive layer. In such embodiments, the metal nanoparticles are deposited during step 603 to form a plasmonic substrate, and the bioactive molecule layer is deposited during step 605. In some embodiments, step 603 includes depositing a reflective metal layer configured as a mirror, and depositing on the mirror a dielectric material, and depositing the metal nanoparticles on top of the dielectric layer.

Any metal may be used in the metal nanoparticles in various embodiments, such as gold, silver, copper and aluminum, or some combination. Any molecule may serve as the target molecule in the bioactive layer, such as a polymer, a ligand, an antigen, an antibody, a protein, a peptide, DNA, RNA, or an oligonucleotide.

In step 611, a reagent is provided, typically in solution. The solution of reagent includes a known quantity of a detection molecule comprising a probe and a fluorophore. The probe is selected to assay for the particular analyte. The probe is labeled with a particular fluorophore from the particular set of fluorophores with emission wavelengths suitable for plasmon light interactions. The reagent can be provided in any manner. For example, in some embodiments, the reagent is obtained from a commercial supplier. In some embodiments, the reagent is provided in an assay kit that also includes the plasmonic substrate and the bioactive molecule in a separate container. In some embodiments the reagent is prepared locally by a user of the assay. In some embodiments, the reagent includes known concentrations of each of several different detection molecules, each with corresponding different fluorophores and each with affinities for corresponding different analytes, e.g., different cytokines secreted from a single cell or different cell surface receptors (also called cell markers), or some combination.

Any molecule may be included as the probe in the detection molecule, such as a polymer, a ligand, an antigen, an antibody, a protein, an oligomer, a protein, a peptide, DNA, RNA or an oligonucleotide. Any fluorophore may be included in the detection molecule, such as fluoresceins, eosin, coumarines, rhodamines, cyanines, benzophenoxazines, phycobiliproteins or fluorescent proteins.

In step 613 a test sample is obtained with a quantity of a particular one or more analytes to be determined by the assay. During a calibration phase used in some embodiments, step 613 includes providing a control sample with known quantities of the one or more particular analytes. For assays that are previously developed, with a known calibration curve, a control sample is not used during step 613. The quantity (such as the presence or concentration) of each of the one or more analytes in the test sample is determined during step 623, described below. Any material may serve as the one of the one or more analytes, such as a polymer, a ligand, an antigen, an antibody, a protein, a cytokine, a peptide, DNA, RNA, oligonucleotide, a virus, bacterium, or a cell from a patient. Analytes for cell markers include one or more of a cytokine receptor, a chemokine receptor, a cluster differentiation protein, another protein in the cell surface membrane.

In step 615, the functionalized substrate is contacted with the test sample and the reagent for sufficient time to produce binding of the one or more different detection molecules to the one or more different analytes or to produce binding of the one or more different analytes to the one or more different fixed bioactive target molecules. To monitor temporal progression of a cell-oriented process, steady state conditions do not need to be reached. Unlike previous sandwich assays, the functionalized substrate need not be brought into contact with the test sample first and allowed to remain in contact for sufficient time to allow the analyte to bind to the target molecules fixed to the substrate in amounts that are proportional to the amount of analyte in the test sample. The functionalized substrate with bound analyte does not then need to be washed to remove excess analyte. The functionalized substrate with bound analyte is not then contacted with the solution of the reagent in a separate step and then maintained for sufficient time to allow the detection molecule to bind to the analyte fixed by the target molecule to the functionalized substrate. The functionalized substrate does not need to be rinsed again to remove the excess detection molecules. In some embodiments for cell processes and cell cell interactions, the plasmonic layer is functionalized with a bioactive molecule that binds to a cell marker that is not an analyte, to cause a low adherence cell to adhere to the substrate via the cell marker bound to the bioactive layer. In some embodiments for cell processes and cell cell interactions, the plasmonic layer is not functionalized with a bioactive molecule because the cell type of interest adheres to the substrate naturally via gravity or some other cell process, In step 617, the substrate and covering solution resulting from step 615 are exposed to excitation electromagnetic waves, such as light, that excites fluorescence in the one or more particular fluorophores corresponding to the different analytes.

In step 619 the relative intensity of emission electromagnetic waves is measured at the emission wavelength of the fluorophore corresponding to each of the one or more analytes. In some embodiments, the measurement is made relative to a reference, such as a control well with no analyte or a control well with no functionalized substrate. In some embodiments, the measurement is made relative to an area of minimum intensity. In the illustrated embodiment, step 619 overlaps in time step 617, as the substrate and covering solution are excited and fluoresce measured at the same or overlapping times. In some embodiments that include step 621, step 619 is omitted.

In step 621 the relative lifetime of emission electromagnetic waves is measured at the emission wavelength of the fluorophore corresponding to each of the one or more analytes. In some embodiments, the measurement is made relative to a reference, such as a control well with no analyte or a control well with no functionalized substrate. In some embodiments, the measurement is made relative to an area of maximum lifetime, since plasmons tend to reduce the lifetime of fluorescent emissions. Any method may be used to measure lifetime, such as measuring time-dependent emission intensity and fitting to a one or two decay coefficients as described above with reference to Equation 1. In some embodiments, lifetime is measured by the phase difference between amplitude modulated excitation and emitted waveforms, with increasing lifetimes causing larger phase differences. In the illustrated embodiment, step 621 overlaps in time step 617, as the substrate and covering solution are excited and fluoresce measured at the same or overlapping times. In some embodiments that include step 619, step 621 is omitted.

The lifetime measurements provide valuable information about the mechanism of the enhancement. For example, if the intensity is enhanced but the lifetime is not changed, this means that the mechanism of intensity enhancement is due to enhanced excitation intensity or an increase in the fluorophore concentration. However, if the fluorescence enhancement is accompanied by a lifetime decrease, the effect of the surface plasmons on the decay rates of the fluorophore needs to be considered. In some embodiments, phase modulation fluorometry is used to acquire data on lifetime changes at the same time as steady-state intensity measurements.

In step 623, a particular quantity of analyte bound to one or more areas on the functionalized substrate is associated with the measured value of relative intensity or lifetime or both. During a calibration phase, the known quantity of analyte in the control sample is associated with the measured values to add points to the calibration curves.

In step 625, one or more analyses of the sample are performed based on the quantities of the bound analytes. For example, one or more functions of an immune system cell are determined by a profile of cytokines secreted during measurement. As another example, a rate of secretion of the analyte by cell is determined based on a difference with a prior or subsequent measurement. In some embodiments, step 625 includes exposing the sample to one or more stimulants, e.g., to induce an immune reaction in a sample that includes one or more cells of an immune system.

In step 627, it is determined whether to make a measurement of the same sample at another time. This is only possible because the sample and reagent do not need to be rinsed off to make the measurement. If so, then control passes back to step 617 to expose the sample again to excitation electromagnetic waves. If not, then another sample, if any, is measured on another substrate, e.g., on another well of the same glass substrate or on other slide altogether, e.g., by returning to step 601 or step 613. In some embodiments, the next measurement is with another known quantity of analyte in another control sample to produce another point for the calibration curve. In a post calibration operational phase, a quantity on the established calibration curve associated with the measured intensity or lifetime, or both, is determined to be the quantity of the analyte in the test sample. The quantity indicates, for example, the presence, absence or concentration of the analyte.

As described in more detail below, the inventors developed planar plasmonic substrates that provide fluorescence amplification of more than 200-fold and demonstrated cytokine assay sensitivities in the range of 10 pg/ml and below.

Further, the inventors demonstrated that the developed plasmonic substrates are robust and applicable to cellular studies. Because this approach is similar to ELISPOT, these MEF-based assays for single cell analysis are called MEF-spot. The MEF-based approach provides an opportunity for platform technology applicable to a broad range of immunoassays including single cell assays. The MEF-based technology described has attributes of ELISA (sensitivity and application to liquid samples), ELISPOT (sensitivity and applications to single cells), and flow cytometry (quantitation of production of cytokines by single cells).

In addition there are several advantages. There is no requirement for specific assay reagents; standard kits for sandwich type assay are used in various embodiments. There is no requirement for specific fluorescent probes; every fluorophore undergoes MEF. There is no requirement for special detection devices; all fluorometric readers are used in various embodiments; microscopy is used for imaging cell populations. There is no requirement for new special procedures. Procedures are simplified compared to ELISA and ELISPOT. The techniques are amendable for high-throughput and printable protein arrays. The techniques are easy to customize for particular assays, are easy to use as a one-step assay, and are cost effective because they are effective with small samples, small cell numbers, and the plasmonic substrates can be mass produced. As described in more detail below, MEFspot technology has a further advantage of enabling simultaneous detection of cell-secreted proteins and cell-surface expressed receptors.

Advantages of the high contrast generated by minute amount of bound probe in MEFspot results in new capabilities for cellular studies not available with other techniques, including: real-time monitoring of protein secretion; direct quantification of secretion; dual modality for secretion verification using both intensity and lifetime; multiplexing and simultaneous detection of cell phenotype and function; and, monitoring simultaneously cell viability and cell function.

It is anticipated that MEFspot will be regarded as a highly innovative detection platform for immunoassays and cellular analysis of heterogeneous cell populations which will have high impact in cancer research, immunology, diagnostics, and therapeutic development, among others.

Some embodiments of the invention are directed to an MEFspot assay kit. In these embodiments, the user is a recipient of the kit. In one embodiment, this kit includes a plasmonic substrate and one or more containers of target molecules in solution to functionalize the substrate for assays for one or more corresponding analytes. In some embodiments, the kit also includes one or more containers of detection molecules for the one or more corresponding analytes. In some embodiments, the kit includes containers of unlabeled biomolecules to serve as probes for detection molecules for the one or more corresponding analytes, and containers for one or more fluorophores. Recall that a detection molecule includes a probe and a fluorophore. The fluorophores are selected from a particular set for which emission wavelengths are long compared to the nanoparticle sizes on the substrate. The user labels the biomolecules with a fluorophore chosen from an included container to produce a reagent of detection molecules. In a preferred embodiment, the probe molecules are already labeled with the selected fluorophore and provided in a container as a reagent of detection molecules. In some embodiments, one or more control samples with known quantities of analyte are also included to be used to generate calibration curves. In some embodiments, printed media or a computer-readable medium is included with data that indicates a calibration curve and software to compute the various analyses that can be performed with the data, such as phasor diagrams described below.

The MEFspot assay kit provides the recipient with materials to perform a MEFspot assay on the recipient's own one or more test samples according to one or more embodiments of method 600.

2. EXAMPLE EMBODIMENTS

Here are described planar plasmonic substrates that provide fluorescence amplification of about 200-fold and demonstrate cytokine assay sensitivities in the range of 10 pg/ml and below as well as improved performance for cell interaction assays.

2.1 Plasmonic Substrates.

In some embodiments, silicon monoxide and silver wire (99.999%) were obtained from SIGMA-ALDRICH™ of St. Louis, Mo. Streptavidin (SA) or avidin (Av) conjugated dyes, Alexa Fluor 350 (AF350-Av), Alexa Fluor 488 (AF488-SA), and Alexa Fluor 647 (AF647-SA) were obtained from INVITROGEN™ of Carlsbad, Calif.). Phosphate buffer saline (PBS) pH 7.4 and biotinylated bovine serum albumin (BSA-Bt) were from SIGMA-ALDRICH™. Ultrapure water (>18.0 MΩ) purified using a Millipore Milli-Q gradient system was used in preparation of buffers and aqueous solutions.

For fabrication of multilayered plasmonic substrates, in some embodiments, glass microscope slides were purchased from VWR™ of Radnor, Pa. Glass slides were cleaned with "piranha solution" (35% H2O2/H2SO4, 1:3) overnight, rinsed with distilled deionized water, and dried with nitrogen before thermal vacuum deposition steps. Metallic and dielectric layers were deposited by thermal evaporation (Edward, model 306) or magnetron sputtering (AJA model ATC 1800-V). For thermal deposition, chromium (adhesion layer) and silver (mirror and outer layer) were evaporated from tungsten boats at $2 \times 10^{-7}$ Torr and silicon monoxide at $5 \times 10^{-6}$ Torr with a deposition rate of ~1.0 nm/minute. In some embodiments, after coating with silicon monoxide (or silicon dioxide), slides were silanized by immersion in a water solution of 1% of aminopropyl trimethoxysilane (APS), for 30 min. The silanized slides were dried in air and used for deposition of a final thin layer of Ag followed by thermal annealing in air at various temperatures and various annealing times.

For evaluation of fluorescence enhancements, the surfaces of annealed and non-annealed slides were covered with a self-adhesive silicone/rubber of thickness of 2 millimeter (mm, 1 mm=$10^{-3}$ meters) with wells of 2.5 mm diameter. First, the BSA-Bt solution (100 micograms per milliliter, μg/ml, 1 mg=$10^{-6}$ grams) in sodium phosphate buffer (50 milliMolar, mM, 1 mM=$10^{-3}$ Molar, pH of 7.2) was added into the wells (10 μl, 1 μl=$10^{-6}$ liters) and incubated for 1 hour. This step facilitated a monolayer of BSA-Bt that provided the means for immobilization of streptavidin-dye conjugates. The same procedure was used for preparation of control samples using bare glass slides. After incubation with dye-streptavidin conjugates (25 μg/ml), the wells were washed with PBS buffer to remove unbound dye streptavidin conjugates. Finally, the wells were filled with PBS and covered with a microscope coverslip for spectroscopic measurements. The schemes of multilayer substrates with immobilized dye-streptavidin conjugates are shown in FIG. 4C and FIG. 4D.

In some embodiments, absorption spectra were acquired with a Hewlett-Packard 8453 spectrophotometer. For baseline corrections, bare glass substrate and SiOx coated glass slides were used. Steady-state intensities were measured on the multilayer substrates and compared with the signal of the respective samples on bare glass. Fluorescence enhancement was determined as the intensity ratio of the fluorescence signal measured on the multilayer substrate divided by the signal in respective reference sample on bare glass using identical experimental conditions. Fluorescence from surfaces was measured with epi-fluorescence configuration (e.g., see FIG. 3 with lens instead of scanning coupler 314) using a fluorescence microscope (Axiovert 135TV, Zeiss) with a 10×, NA 0.30 objective (UPlanFl, Olympus). The excitations were provided using ultraviolet (UV) light emitting diode (LED) (Nichia NSHU590E) with a peak wavelength at 374 nm, blue LED (Nichia NSPB500S) with a peak wavelength at 467 nm, and red LED (Nichia NSPR510CS) at 625 nm and emission observed at band-pass filters of 460/50 nm (AF350-Av), 535/50 nm (AF488-SA), and long pass filter above 655 nm (AF647-SA). Time-resolved data were measured using a phase-modulation fluorometer (K2 from ISS, Champagne, Ill.). The LEDs were modulated by applying a RF driving signal from a Marconi model 2022A frequency synthesizer (from Marconi Instruments, Allendale, N.J.) to the LED.

Scanning electron microscopy (SEM) images were collected with a Hitachi SU-70 SEM instrument, and surface morphologies were studied using an atomic force microscope (AFM), model D3000 (from Digital Instruments, Inc.).

A set of silver films with nominal thicknesses 9, 15, 20, 23, 30, and 36 nm were prepared by thermal evaporation of silver (Ag) onto silanized SiOx coated microscope slides. Part of the slide from each set was annealed for 3 hours at 230° C. in air. SEM images and absorption spectra of annealed and non-annealed films were obtained (not shown). In some embodiments, the measurements of absorption spectra were performed for surfaces wetted with phosphate buffer, pH 7.2

Figure 7A:
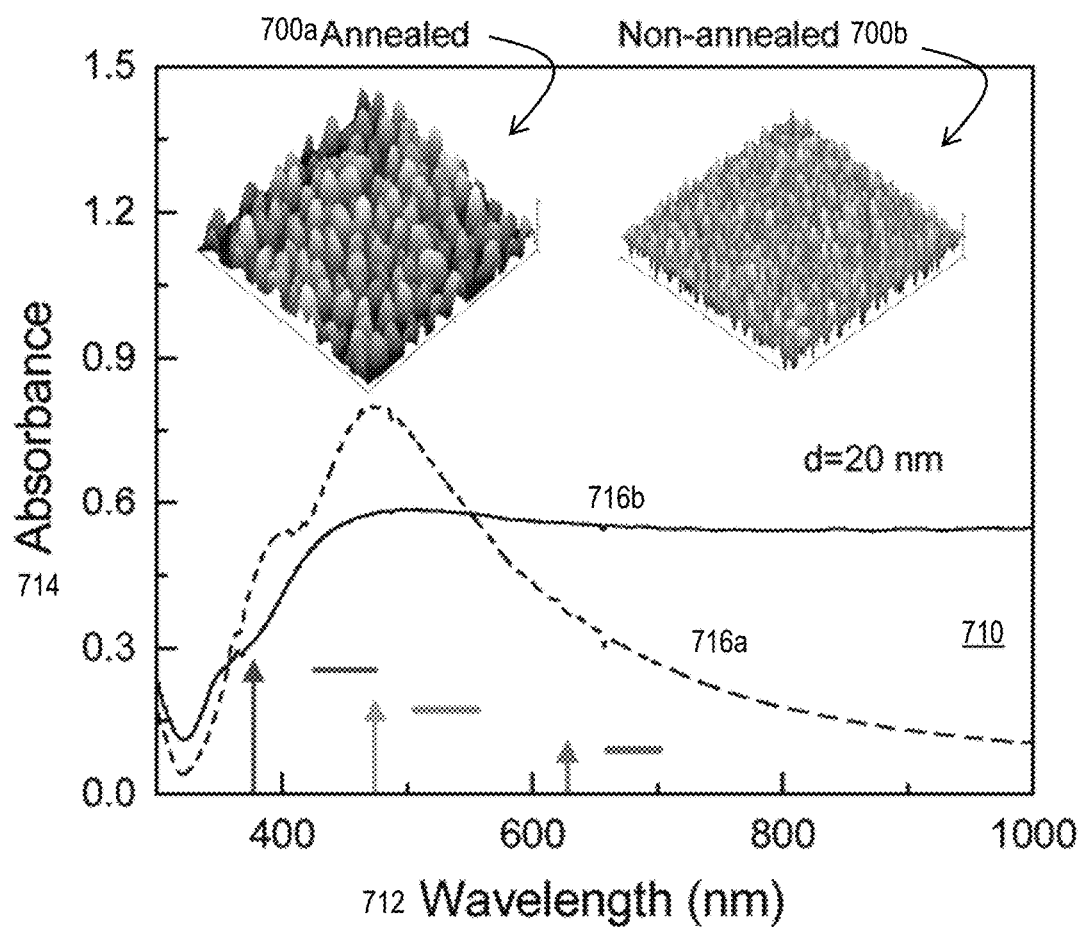
FIG. 7A, FIG. 7B and FIG. 7C are graphs that illustrates example effects of annealing on shape and optical absorption of nanoparticles in a plasmonic substrate, according to an embodiment.
Figure 7B:
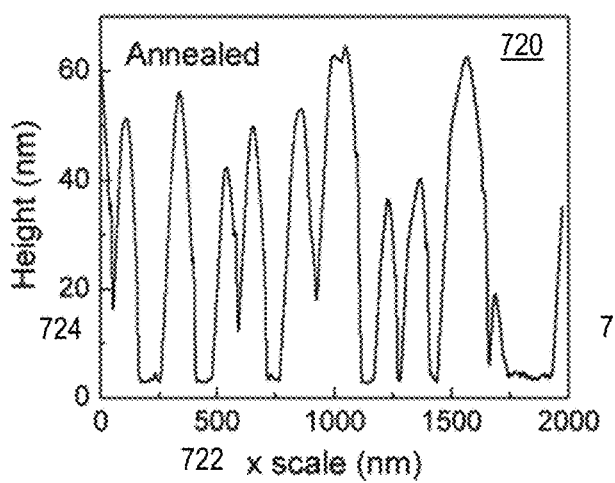
Figure 7C:
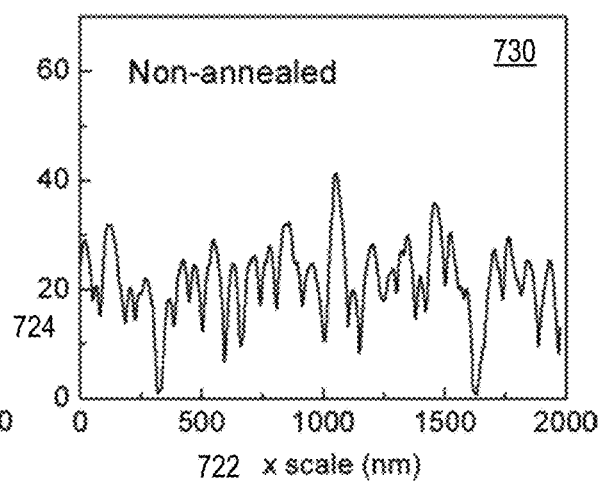

In some embodiments, the layer of metal nanoparticles for the plasmonic substrate obtains improved performance by annealing. FIG. 7A, FIG. 7B and FIG. 7C are graphs that illustrates example effects of annealing on shape and optical absorption of nanoparticles in a plasmonic substrate, according to an embodiment. FIG. 7A is a graph 710 that illustrates example absorbance spectra of annealed and non-annealed Ag layers of 20 nm effective thicknesses on the glass substrate, which were fabricated simultaneously with Ag mirrored substrates coated with dielectric layers. The horizontal axis 712 is optical wavelength and the vertical axis 714 indicates absorbance in units of optical density. Graph 710 shows the respective absorption spectra of annealed (trace 716a) and non-annealed (trace 716b) substrates and three excitation wavelengths (arrows) and three spectral windows (horizontal bars) used for evaluation of fluorescence enhancements. The selected spectral windows overlap with the plasmon spectrum over a broad range of wavelengths representative of the fluorescent dyes commonly used in biotechnology applications. AFM images 700a for annealed and 700b for non-annealed show that the annealing process results in substantial changes in the surface morphology, increasing both lateral and axial dimensions of Ag nanostructures. FIG. 7B is a graph 720 that illustrates an example particle height profile across the annealed image 700a. The horizontal axis 722 is distance in nanometers and the vertical axis is height of particle in nanometers. FIG. 7C is a graph 730 that illustrates an example particle height profile across the non-annealed image 700b. The height profiles indicate that smaller silver nanostructures are formed during the vacuum deposition, with an average height close to the effective deposition thickness of 20 nm.

After annealing, the height of the particles increased up to about 60 nm and the lateral size also increased up to about 150 nm.

Effects of the above fabricated Ag nanostructures on the fluorescence were determined in on embodiment using three fluorophores (AF350, AF488, and AF647). The selected fluorophores have distinct spectral ranges representing coumarins (UV-blue), fluoresceins (blue-green), and cyanines (red), respectively. The selected dye-strept(avidin) conjugates display similar quantum yields: 0.55 (AF350-Av), 0.42 (AF488-SA), and 0.33 (AF647-SA). Similar quantum yields of fluorophores allow more proper characterization of the plasmonic effects of Ag nanostructures on fluorescence enhancement over the broad spectral range. It is known that low quantum yield fluorophores undergo larger fluorescence enhancements compared with that of high quantum yield. Additional advantages of using Alexa Fluors with plasmonic nanostructures are: their better photostabilities; and less self-quenching when labeled with proteins, compared with conventional dyes. The avidin and streptavidin conjugated dyes were immobilized on substrates that were precoated with BSA-Bt. The binding interaction between streptavidin and biotin is very strong and results in a stable monolayer of dye-streptavidin over the BSA. The layer of BSA-Bt serves also as a separation layer between the fluorophores and the silver surface. The average distance between fluorophores (bound to SA) and the surface is about 6 to about 7 nm. This separation prevents fluorescence quenching when the dye is in direct contact with the metallic surface or in close proximity to the surface where the quenching effects are more dominant over the enhancement effects. All investigated substrates, including control bare glass slides, were treated with the same protein concentrations to facilitate a direct comparison of fluorescence signals Because the annealing process has a significant effect on the Ag film morphology and on the overall fluorescence enhancements, the effect of annealing temperature and annealing time on the performance of Ag film-based substrates was investigated. For this study, silver films with a thickness of 30 nm were deposited on the glass substrates having a 25 nm SiOx under layer and annealed at various temperatures for a fixed time (2 hours). A Ag thickness of 30 nm was selected to possibly maximize the annealing effect on the fluorescence enhancement. Note that this Ag thickness is not optimal for enhancement. The second set of substrates was annealed for different times at a fixed temperature (180° C.). The fluorescence enhancements for annealed and non-annealed films showed that the optimal annealing temperature is in a broad range from about 100 to 200° C., and sufficient annealing time is from about 5 minutes to about 60 minutes, preferably about 60 minutes.

FIG. 8A and FIG. 8B are block diagrams that illustrate example configurations in the vicinity of a substrate for which optical fields are simulated to determine the effects of the dielectric layer thickness on fluorescence enhancement, according to an embodiment. FIG. 8A depicts a reference model with a layer 860 of water overlaying a layer 810 of glass. Incident light has an electric field $E_{y0}$ that is polarized parallel to the interface between the layers 810 and 860. The average excitation field intensity and radiation power of randomly distributed dipoles were computed for a 10 nm layer 880a above the interface. FIG. 8B depicts a model of an advantageous plasmonic substrate. The model plasmonic substrate includes glass layer 810 and water layer 860 but includes a silver (Ag) mirror layer 824 above the glass, a silicon dioxide ($SiO_2$) layer 823 above the mirror, and a silver (Ag) nanoparticle layer 822 above the $SiO_2$ layer 824.

The average excitation field intensity and radiation power of randomly distributed dipoles were computed for a 10 nm layer 880b above the interface of the layers 822 and 824 with the water 860. The parameters of the plasmonic substrate model include Ag array of semi-spheres with diameter of 60 nm and 40 nm edge-to-edge spacing, Ag mirror with thickness of 48 nm, $SiO_2$ layer with variable thickness from 0 to 240 nm and water thickness of 500 nm.

Numerical calculations were based on the finite-element method (FEM) using COMSOL Multiphysics version 3.5a from COMOL INC.™ of Burlington, Mass. Two mechanisms of fluorescence enhancement caused by the multi-layered substrates were considered: enhancement in the excitation and enhancement in the emission confined to the region where fluorescent probes are located. Thus we performed two set of calculations: (1) calculating the effect of coupling of excitation light into a multi-layered substrate via average field intensity within a 10 nm layer above the surface and (2) calculating the emission enhancement of randomly distributed and randomly oriented dipoles (representing fluorophores) within a 10 nm layer above the Ag nanoparticles.

For experimental comparisons, in some embodiments, glass slides (from VWR) were cleaned with "piranha solution" (35% $H_2O_2/H_2SO_4$, 1:3) overnight, rinsed with distilled deionized water and dried with nitrogen before performing vacuum deposition steps. Metallic and dielectric layers were deposited using magnetron sputtering (AJA Model ATC 1800-V from AJA INTERNATIONAL INC.™ of Scituate, Mass.). First, a 1.5 nm chromium layer was deposited on glass for adhesion of an Ag layer of 200 nm thickness. After deposition of Ag film, a silicon dioxide layer with thickness varying from 3 to 300 nm. A final thin layer of Ag of about 13 nm was deposited followed by thermal annealing in air at 180° C. for 1 hour.

The surfaces of the substrates and reference glass slides were coated with biotinylated bovine serum albumin (BSA-Bt) using 100 μg/ml solution in phosphate buffer with an incubation time of 1 hour. This step formed a monolayer of BSA-Bt that facilitated the immobilization of streptavidin-dye conjugates (5 μg/ml). Streptavidin (SA) conjugated dyes are: Alexa Fluors from INVITROGEN™ AF488-SA, AF647-SA, AF680-SA, and AF750-SA; and the infra red dye IRD800-SA from LICOR™ of Lincoln, Neb. Phosphate buffer (PB) pH 7.4 and biotinylated bovine serum albumin (BSA-Bt) were from SIGMA-ALDRICH™. Ultrapure water (>18.0 MΩ) (Millipore Milli-Q gradient system) was used in the preparation of buffers and aqueous solutions.

Extinction spectra were measured with a Hewlett-Packard 8453 spectrophotometer from HEWLETT-PACKARD™ of Palo Alto, Calif., relative to the bare glass. Reflectance spectra were acquired with a Cary 100 Bio spectrophotometer from VARIAN MEDICAL SYSTEMS INC.™ of Palo Alto, Inc., equipped with an external specular reflection attachment with fixed angle of incidence of 12 degrees. For baseline correction, a reference aluminum mirror (reflectance accessory) was used. Scanning Electron Microscopy (Hitachi SU-70 from HITACHI, LTD.™ of Tokyo, Japan) was used for surface morphology imaging. Fluorescence from surfaces was measured using an epi-fluorescence microscope (Axiovert 135TV from ZEISS GMBH™ of Jena, Germany, see FIG. 3) with 10x, NA 0.30 objective (UPlanFl from OLYMPUS CORPORATION™ of Tokyo, Japan). Excitation was provided using either a blue LED (NSPB500S from NICHIA CORPORATION™ of Tokushima, Japan) with peak wavelength at 470 nm or a red LED (NSPR510CS from NICHIA CORPORATION™) at 630 nm, and the emission was observed through a band pass filter of 535/50 nm (AF488-SA) and long pass filter above 655 nm (red dyes). An NIR reader Odyssey from LICOR™ was used for NIR dyes at laser excitation of 680 and 780 nm. Steady-state intensities were measured on the multi-layer substrates and compared to the signal of the respective samples on bare glass. Fluorescence enhancement was determined as the intensity ratio of the fluorescence signal measured from the multi-layer substrate over the signal from the respective reference sample on bare glass using identical experimental conditions. Time-resolved data were measured using phase-modulation fluorometer (K2 from ISS, Champagne, Ill.). The LEDs were modulated by applying a RF driving signal from a Marconi Model 2022A frequency synthesizer (from MARCONI INSTRUMENTS™, Allendale, N.J.) to the LED.

Figure 9A:
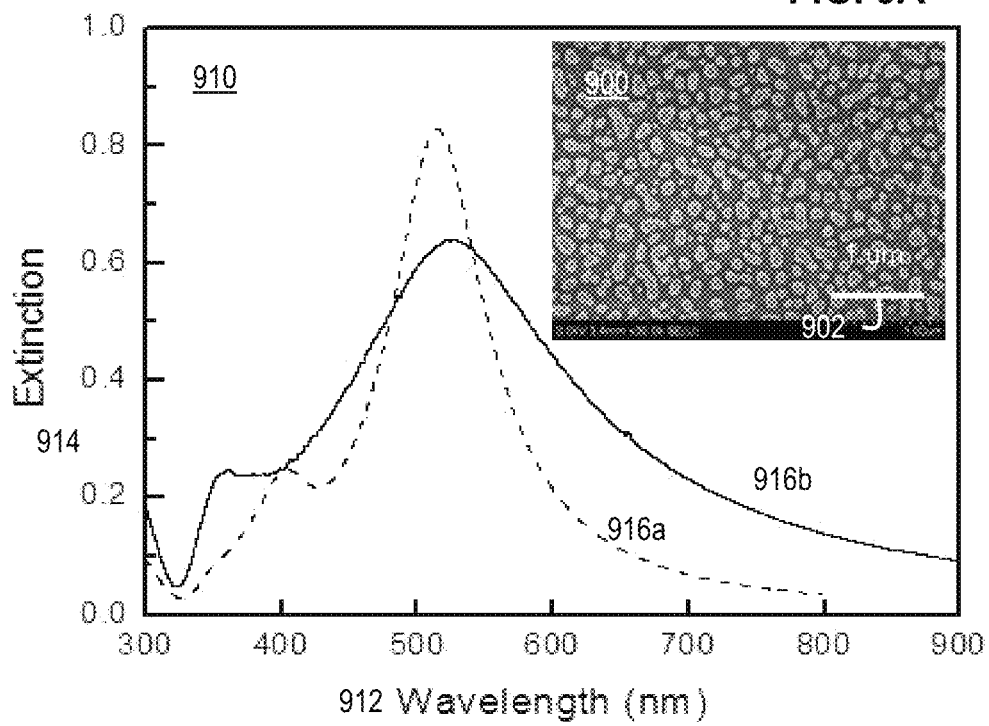
FIG. 9A and FIG. 9B are graphs that illustrate the ability of the simulation to match data, according to an embodiment.
Figure 9B:
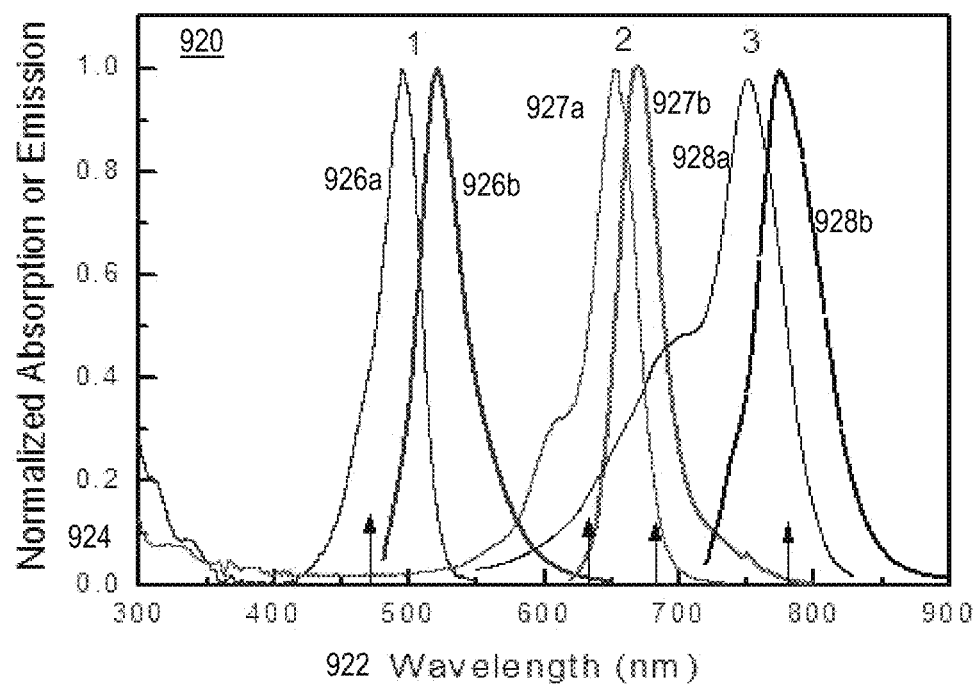

FIG. 9A and FIG. 9B are graphs that illustrate the ability of the simulation to match data, according to an embodiment. FIG. 9A is a graph 910 and image inset 900. The inset 900 presents an example scanning electron micrograph (SEM) image of Ag nanoparticles obtained after annealing an Ag film with thickness of 13 nm on silica coated glass. The Ag nanostructures can be considered as a collection of nanoparticles heterogeneous in size and shape. Using an imaged area of 2×2 μm², the estimated filling factor is 24%, with about 11% of the area covered with circular particles of average diameter of 81±26 nm and 13% with elongated particles of average size 77 nm×132 nm.

Graph 910 has a horizontal axis 912 that indicate optical wavelength in nanometers, and a vertical axis 914 that indicates extinction, a dimensionless quantity. Calculated extinction (E) is determined from the calculated transmission (T) of incident light using the formula $E = \log(1/T)$. The graph depicts example extinction spectrum of Ag nanoparticles on silica coated glass (solid line 916b) and the numerically calculated spectrum for Ag array of semispherical nanoparticles of 60 nm diameter and edge-to-edge spacing of 40 nm (dashed line 916a). There is good qualitative agreement.

FIG. 9B is a graph 920 that illustrates example absorption and emission spectra of selected fluorophores. The horizontal axis 922 is optical wavelength in nanometers and the vertical axis 924 indicates normalized intensity in arbitrary units. Graph 920 depicts absorption spectra (thin lines 926a, 927a and 928a) and emission spectra (thick lines 926b, 927b and 928b) of the AF488-SA (1), AF647-SA (2), and AF750-SA (3) fluorophores, respectively. For clarity of figure, spectra of other fluorophores are not included. Arrows indicate the experimental excitation wavelengths within the absorption peaks for some embodiments.

When the silica thickness is increased above the 75 nm in some embodiments, the reflectance spectra are more complex, displaying well-defined minima and maxima specific to the particular silica thickness. Reflectance properties of the substrates indicate that incident light can be highly reflected, almost to 100%, as well as can be highly absorbed or transmitted (low reflectance of about 5%). Measurements of UV/Visible/near infrared (NIR) reflectance and extinction suggest a complex interaction of light with plasmonic structures coupled to a photonic cavity. Therefore, in order to better understand the fluorescence enhancement and to gain insights on rational design of the substrates, numerical calculations were used to determine the effect of variation in silica thickness of multi layered substrates on the excitation and emission enhancements for selected wavelengths. An important factor is the interplay between Ag surface plasmon resonance and resonance within a silica layer which can be constructive as well as destructive as indicated by the reflectance spectra.

Figure 10A:
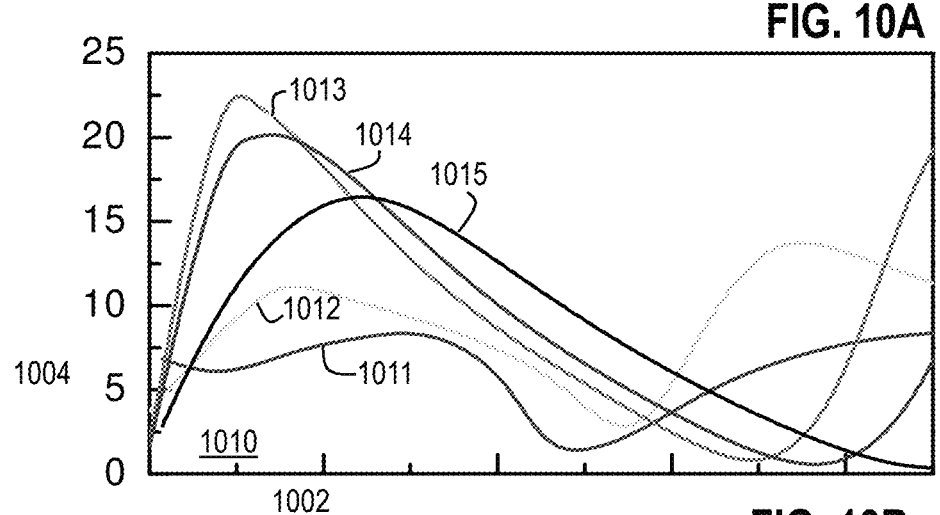
FIG. 10A, FIG. 10B and FIG. 10C are graphs that illustrate example enhancement of excitation light intensity based on thickness of dielectric layer, according to various embodiments.
Figure 10B:
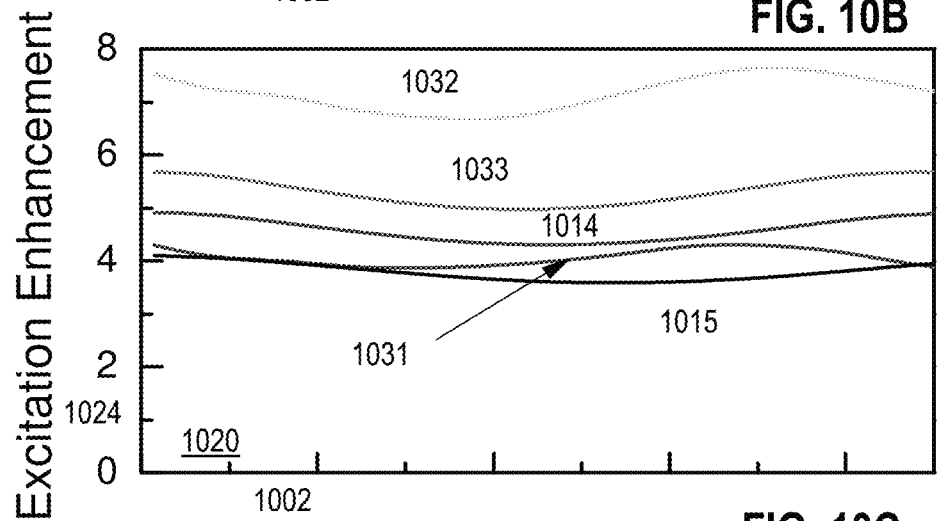
Figure 10C:
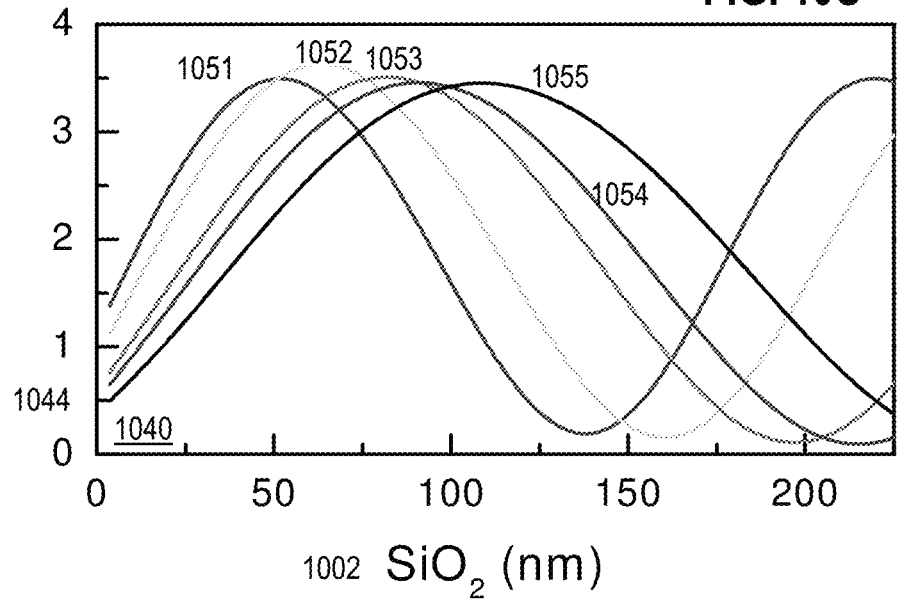

The excitation enhancement was calculated as the ratio of average electromagnetic power within the 10 nm volume above the surface of the substrate to that of bare glass with the same silica thicknesses. FIG. 10A, FIG. 10B and FIG. 10C are graphs 1010, 1020, 1040 that illustrate example enhancement of excitation light intensity based on thickness of dielectric layer, according to various embodiments. The horizontal axis 1002 indicates thickness of the SiO2 layer. The vertical axes 1004, 1024, 1044, respectively, indicate the excitation enhancement, which is dimensionless. FIG. 10A is for a plasmonic substrate with mirror, dielectric layer and Ag nanoparticles. FIG. 10B is for a plasmonic substrate with dielectric layer and Ag nanoparticles. FIG. 10B is for a substrate with a mirror and dielectric layer abut no Ag nanoparticles. On each graph there are five traces corresponding to five excitation wavelengths. For the three graphs, respectively, enhancements at 470 nm are shown on traces 1011, 1031, 1051; enhancements at 530 nm are shown on traces 1012, 1032, 1052; enhancements at 630 nm are shown on traces 1013, 1033, 1053; enhancements at 680 nm are shown on traces 1014, 1034, 1054; and, enhancements at 780 nm are shown on traces 1015, 1035, 1055. These calculations indicate that the substrate with mirror, silica cavity and AgNP provides the most efficient excitation enhancements.

The substrate with silica layer thickness of approximately 25-60 nm facilitates similar enhancements across a broad range of excitation wavelengths. Using greater silica thicknesses above 150 nm, one can also obtain high excitation enhancement (second peak) which varies strongly with wavelength; therefore multiple spectrally-distinct fluorophores may display very different enhancements or even quenching. Such strong wavelength dependence may be useful for construction of substrates for detection systems where some wavelengths need to be enhanced and other suppressed. Thus plasmonic substrates with thickness from about 20 nm to about 75 nm, and preferably a range from about 25 nm to about 60 nm, are used for a wide range of fluorophores in some embodiments. In some embodiments, one or more of the larger thicknesses of the dielectric layer are chose to enhance a particular fluorophore at the expense of other fluorophores. Thus, in some embodiments, a thickness of the dielectric layer is selected to maximize fluorescent enhancement for a particular fluorophore in the detection molecule For emission enhancement calculations a random distribution of point dipoles (fluorophores) was assumed both in terms of the orientation of the transition dipole moments and in distances from the surface within a 10 nm conformal layer. The total number of dipoles was 81 in the volume of 100×100×10 nm³ with transition moments equally distributed over the X, Y, and Z direction (27 dipoles per direction). It was found that two-fold increase of number of dipoles resulted in minor increase in calculated emission enhancement of about 5%. The enhancement factors were calculated relative to the reference system of the glass slide without any additional dielectric or metal layers. For the reference sample, only dipoles oriented in the Y direction were considered.

Figure 11A:
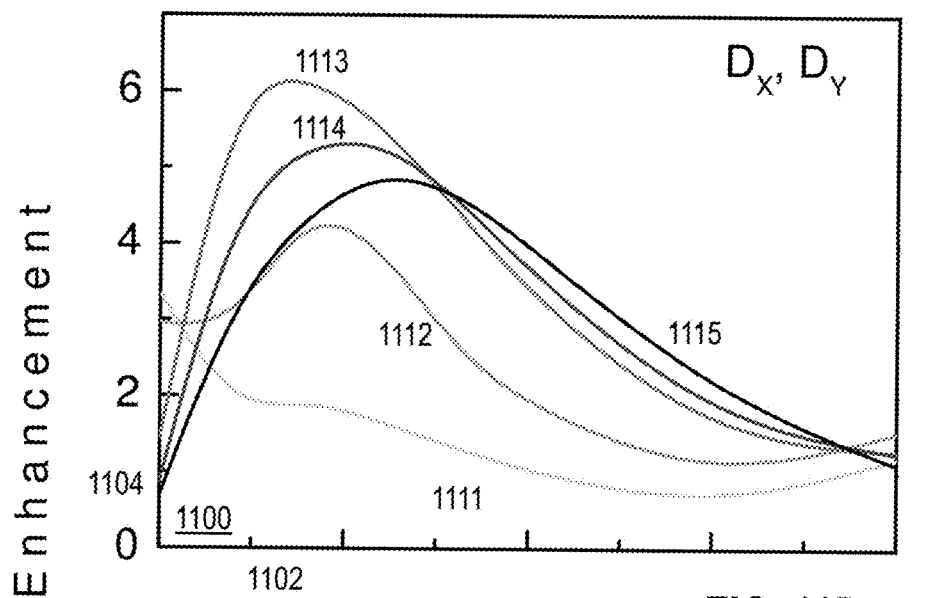
FIG. 11A and FIG. 11B are graphs that illustrate example enhancement of emission light intensity based on thickness of dielectric layer, according to various embodiments.
Figure 11B:
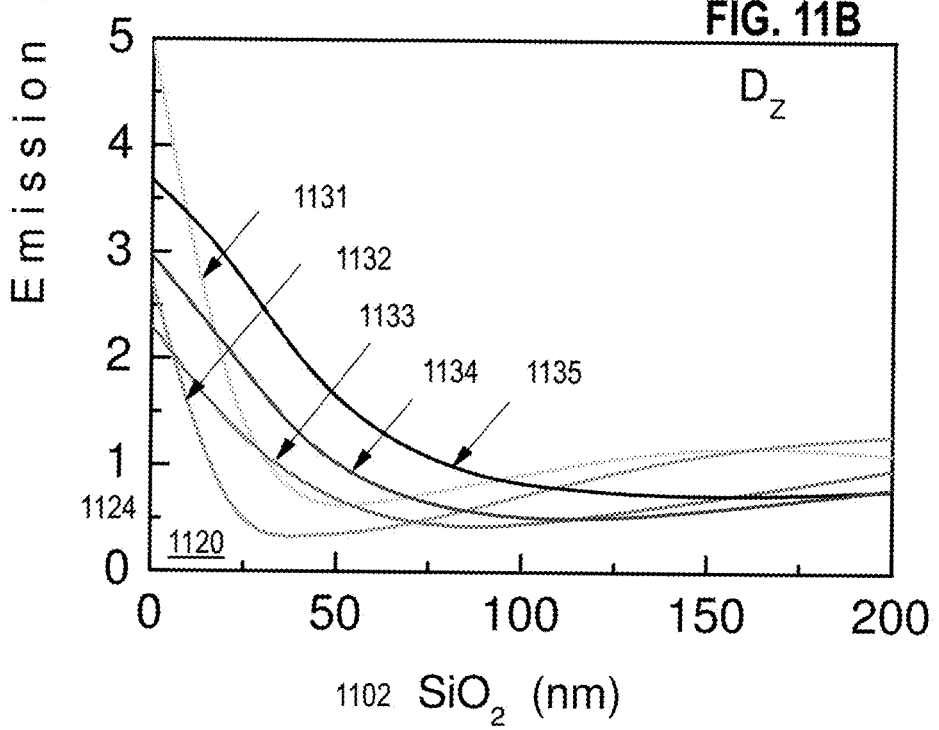

FIG. 11A and FIG. 11B are graphs 1100, 1120, respectively, that illustrate example enhancement of emission light intensity based on thickness of dielectric layer, according to various embodiments. The horizontal axis 1102 indicates thickness of the $SiO_2$ layer. The vertical axes 1104, 1124, respectively, indicate the emission enhancement, which is dimensionless. The measurement of radiation power is within a cone of 18 degrees. FIG. 11A graphs the dipole transition moment parallel to the interface (Dx, Dy); and FIG. 11B graphs the dipole transition moment perpendicular to that surface (Dz). On each graph there are five traces corresponding to five excitation wavelengths. For the two graphs, respectively, enhancements at 550 nm are shown on traces 1111, 1131; enhancements at 580 nm are shown on traces 1012, 1132; enhancements at 680 nm are shown on traces 1113, 1133; enhancements at 720 nm are shown on traces 1114, 1134; and, enhancements at 800 nm are shown on traces 1115, 1135. The dependence of X dipole emission on silica thickness is similar to the excitation dependence (FIG. 10A), for example, the enhancements are maximal at about 25 nm for excitation at 630 nm and for X-oriented emitter at 680 nm. However, the enhancement is quite different for the Z-oriented emitter; the greatest enhancement is observed for no silica layer, while some quenching (<1.0) or no enhancement (~1.0) is observed for most of the silica thicknesses.

The lack of sharp layer-thickness-dependent enhancements is advantageous for the applications of these Ag film/dielectric substrates. This is because it allows relaxed conditions for reproducible fabrication. In addition, it allows use of the same substrate for a broad range of fluorophores, an important aspect for multiplexing approaches. These results show that substrates fabricated using two different vacuum deposition systems, thermal and magnetron sputtering, resulted in a very similar performance. It is anticipated that this approach finds immediate applications in surface-based sensor designs because of easy fabrication and the availability of a broad range of fluorescent probes for various biotechnological applications.

Figure 12A:
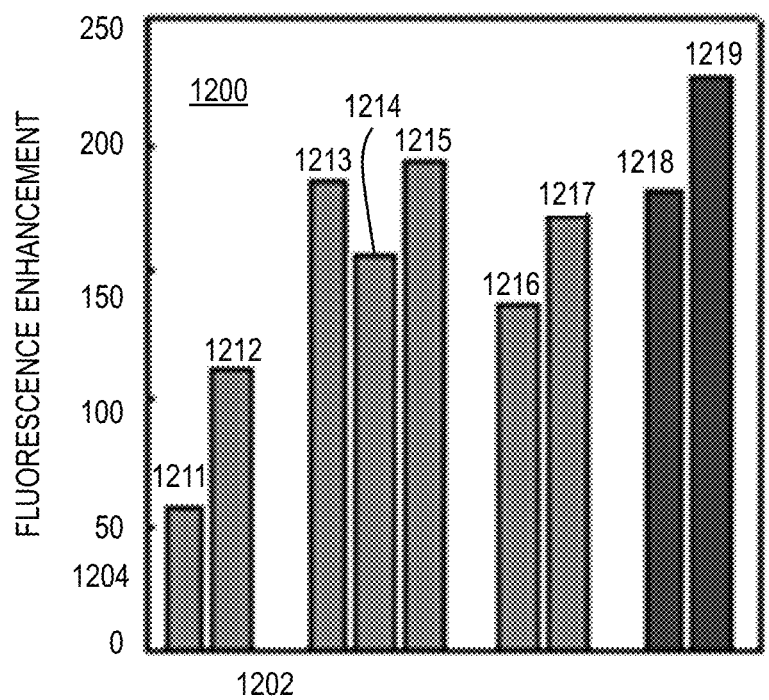
FIG. 12A is a graph that illustrates example measured enhancements of fluorescence intensity for an example plasmonic substrate at multiple optical frequencies, according to various embodiments.

FIG. 12A is a graph 1200 that illustrates example measured enhancements of fluorescence intensity for an example plasmonic substrate at multiple optical frequencies, according to various embodiments. The horizontal axis 1202 indicates individual fluorophores. The vertical axis 1204 indicate fluorescence enhancement as a dimensionless factor. Fluorescence enhancements are depicted for Alexa Fluors and DY dyes in blue-green, including AF488 as bar 1211, AF532 as bar 1212; in red including AF632 as bar 1213, AF647 as bar 1214, DY649 as bar 1215; in far red including: AF680 as bar 1216, DY680 as bar 1217; and in near infrared including: AF750 as bar 1218 and IRD800 as bar 1219. These results show fluorescence enhancements of more than 200-fold for an ensemble of dyes in a broad spectral range. Other results (not plotted) include fluorescence enhancements of about 400-fold to 1000-fold observed for Cy5 single molecules.

Figure 12B:
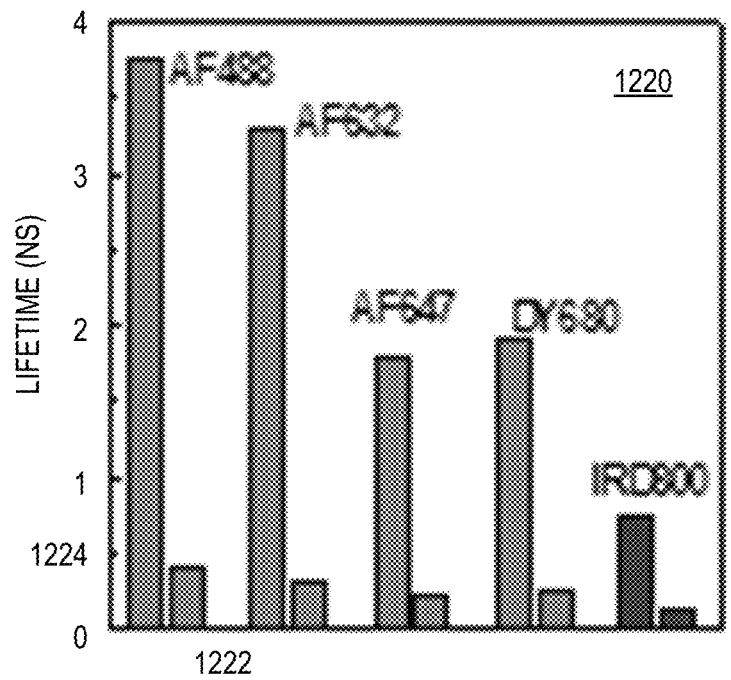
FIG. 12B is a graph that illustrates example measured lifetimes of fluorescent emission for an example plasmonic substrate at multiple optical frequencies, according to various embodiments.

FIG. 12B is a graph 1220 that illustrates example measured lifetimes of fluorescent emission for an example plasmonic substrate at multiple optical frequencies, according to various embodiments. The horizontal axis 1222 indicates 5 individual fluorophores with and without, respectively, these multiplayer plasmonic substrates with mirror and dielectric layer. The vertical axis 1204 indicates lifetime in nanoseconds (ns, 1 ns=$10^{-9}$ seconds). Lifetime of every fluorophore is decreased by about 10-fold.

The excess of the surface area due to Ag nanostructures was estimated to be less than 25% compared with the planar glass. This estimate assumed an array of semispherical particles with a diameter of 40 nm and spacing (side-to-side) of 40 nm and found that particles will increase the total surface area by about 21%. Therefore, the observed large fluorescence enhancements are due to surface enhanced phenomena and not the differences in the surface concentration of bound dye-streptavidin conjugates. In view of sensing applications, the increase in the sensing active area is desirable for improved sensitivity.

The intensity and lifetime data illustrate that fluorescence enhancement on multilayer substrates is due to several effects, including the reflective properties of mirrors with an optimal dielectric thickness layer, the surface plasmons of the outer layer of Ag nanostructures, and the increased surface area for protein binding. It is observed that fluorescence enhancement due to Ag nanostructures strongly depends on the spectral range. This suggests that the far-red (AF647) and possibly infrared wavelength ranges are the most promising for fluorescence enhancement with Ag nano structures. The proper combination of layers and the annealing process provides a convenient method for the fabrication of planar substrates suitable for stable fluorescence enhancements over 200-fold, which can be applied for the design of low-cost detection instrumentation for proteomics and genomics applications Deposition of thin silver films and subsequent thermal annealing provides a means for the fabrication of silver nanostructures that significantly amplify the fluorescence. The enhancement of fluorescence is highly dependent on the fabrication parameters and the spectral range. An average enhancement from about 50-fold in blue-green and up to 210-fold in the red range has been observed. A noted advantage of the fabrication method is its simplicity. The substrates can be deposited by a vacuum process, followed by annealing in air. In addition, because of the simplicity of the method, a large number of substrates can be produced using simple microscope glass slides that accommodate a large area for enhanced biosensing and can utilize many available fluorescent readers and fluorophores. It is expected that high reproducibility of substrates for enhanced fluorescence are achieved with the described fabrication process. This is because the critical thicknesses of the dielectric and Ag outer layers can be deposited with high accuracy using a vacuum deposition process. The two vacuum deposition systems used resulted in very similar values of fluorescence enhancements for two dyes and a broad range of dielectric thicknesses. Moreover, the optimal fluorescence enhancement occurs for a relatively broad range of dielectric as well as Ag effective thicknesses, which further assures the reproducible performance of the substrates.

To make use of the mirror's contribution to the enhancement it is desirable that the optical density of the metal nanoparticles not be so great as to block transmission of light into the dielectric layer. Therefore an optical density of less than about 1.0 (10% transmission) is desirable. In other embodiments, optical density is selected in a range from about 0.2 to 1.5.

2.2 Assays for Cytokines.

Figure 13:
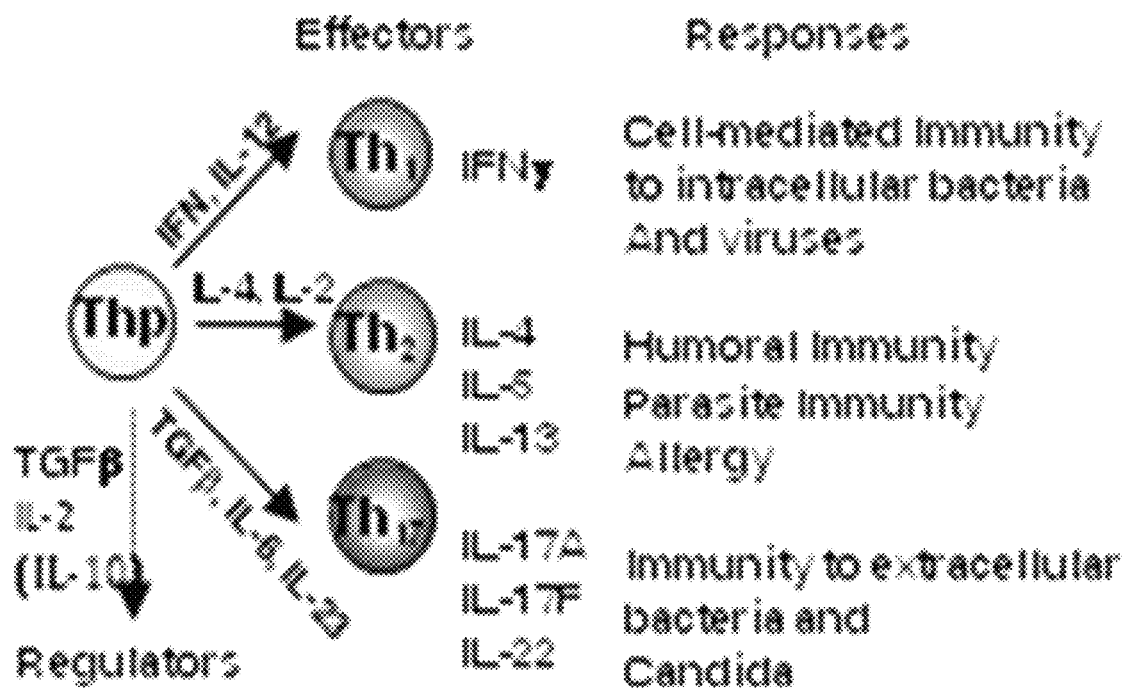
FIG. 13 is a block diagram that illustrates example cytokines of interest, according to various embodiments.

FIG. 13 is a block diagram that illustrates example cytokines of interest, according to various embodiments. Differentiation of naïve CD4+ cells (Thp) into T cell subsets are defined by their cytokine production profiles. IL-4 drives the differentiation of Th2 cells, which mainly produce IL-4, IL-5 and IL-13. IL-12 polarizes Thp cells towards Th1 cells, which mainly produce IFNγ. The presence of IL-6 and TGFβ causes Thp cells to form into Th17 cells which mainly produce IL-17A, IL-17F, and IL-22. Th1 cells are considered to be major effectors against viral infection, intracellular pathogens, and cancers. Recent studies indicate that detection of double IFNγ/IL-2 producing T cells provides additional clinical information regarding the prognosis of patients with human immunodeficiency virus (HIV) compared to enumeration of IFNγ or IL-2 secreting T cells alone. Furthermore, heterogeneity in IL-5-production by IL-4+ Th2 cells was observed in humans and was correlated with different allergic phenotypes. An association has also been found between the IL-13+ IFNγ+ double producers and enhanced allergic inflammation.

Figure 14:
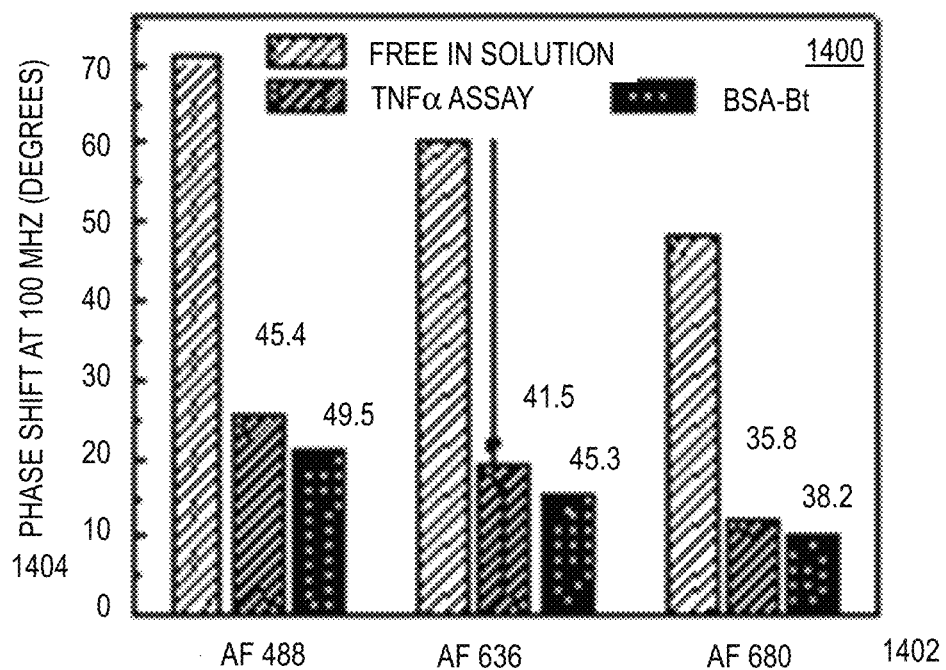
FIG. 14 is a graph that illustrates example differences among lifetimes of fluorescence emissions in various layers in or above the plasmonic substrate for three dyes, according to an embodiment.

In one embodiment, a high density of capture antibody on the surface of MEF substrate was demonstrated, along with the resulting intensity enhancement and lifetime decrease of fluorescence of detection antibody in sandwich cytokine assays. For this embodiment, results obtained with TNFα assay and biotinylated BSA (BSA-Bt) were compared. TNFα assay comprised of Ab1/TNF (500 ng/ml)/Ab2-Bt and detection was with dye-streptavidin conjugates. Phase shifts were measured for probes in solution and when bound to the surface via captured TNFα. The results were compared to biotinylated BSA (BSA-Bt) coated substrates. Blocking solution (5% BSA) was used to minimize non-specific binding. Control sample was surface-coated with BSA-Bt where typically a monolayer of BSA is formed on the surfaces. Probe concentration in each case was 2 μg/ml, to saturate the biotinylated surface FIG. 14 is a graph that illustrates example differences among lifetimes of fluorescence emissions in various layers in or above the plasmonic substrate for three dyes, according to an embodiment. The horizontal axis indicates each of three fluorophores (AF488, AF636, AF680) in each of three states (free in solution; in a TNFα assay; and on the BSA-Bt fixed target molecule). The vertical axis indicates phase shift at 100 megahertz (MHz, 1 MHz=$10^6$ Hertz, Hz, 1 Hz=1 cycle per second) in degrees. Fluorescence lifetime is related to this phase shift by $\tau=\omega^{-1}\tan\varphi$, where $\tau$ is lifetime, $\omega$ is radial modulation frequency, and $\varphi$ is phase shift. FIG. 14 shows that phase shifts up to almost 45 degrees (significant lifetime changes) were obtained in the assay configuration. These large phase changes imply great potential for the design of a sensitive assay using lifetime detection modality. Larger changes were observed for BSA-Bt because of the shorter distance between fluorophore in BSA-Bt/SA-dye compared to Ab1/TNF/Ab2-Bt/SA-dye. The intensity enhancements in this assay format were slightly smaller than observed for BSA-Bt of about 20% (not shown). These results indicate that sandwich assay for TNFα is not compromised as compared to BSA-Bt/SA-dye.

Calibration curves for several cytokines were generated using commercial reagents for ELISA (all from Pierce Biotechnology) with secondary biotinylated antibodies (Ab2-Bt) and using dye-streptavidin conjugates (dye-SA) as detection probes. Briefly, the procedure involved adsorption of the capture antibody on the surface by physical adsorption, blocking, adding 3-fold dilutions of cytokines, incubating with Ab2-Bt, and performing measurements in the presence or absence of the detection probe. With plasmonic substrates multiple calibration curves can be generated (while standard methods allow only single calibration curve at one time). Because of the high fluorescence amplification of bound probes, calibration curves can be generated without washing out the detection probe, which introduces intensity changes and/or lifetime (phase and modulation) changes. It was found that the most convenient way to display intensity calibrations is using the ratio of intensity to the baseline signal. The baseline signal includes the background from assay matrix (surface and sample reagent), background from non-specific binding, and the signal from the bulk detection probe (when not washing). This unified form of calibration includes information on the signal-to-background noise (S/N) and allows for direct comparison of various modalities. It is important to identify what contributes to, e.g. poor performance of assay, large background signal or poor performance of selected antibodies.

Figure 15A:
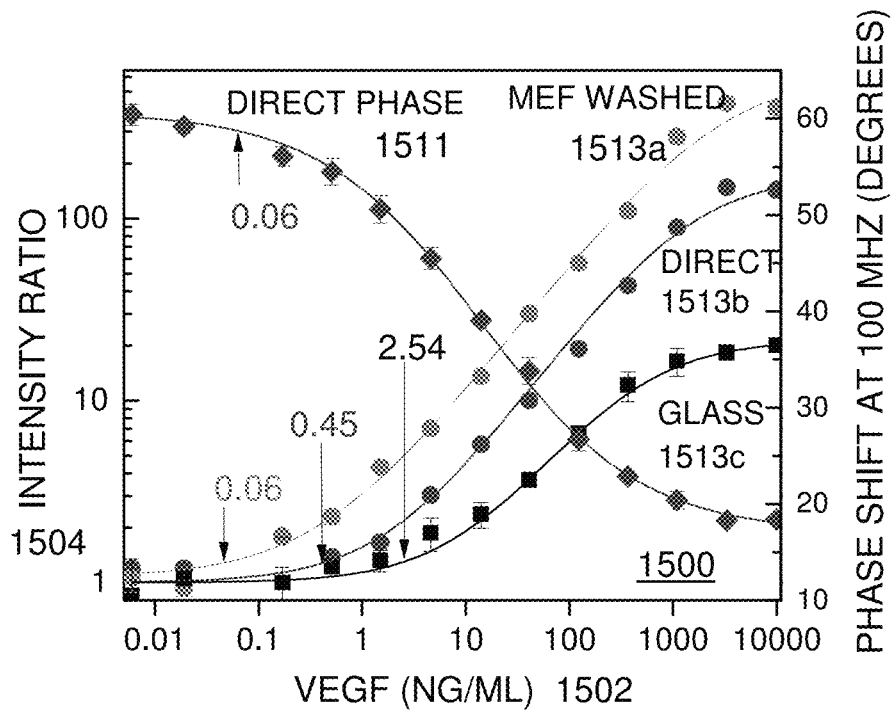
FIG. 15A and FIG. 15B are graphs that illustrate example fluorescence enhancement calibration curves for two cytokines, according to various embodiments.
Figure 15B:
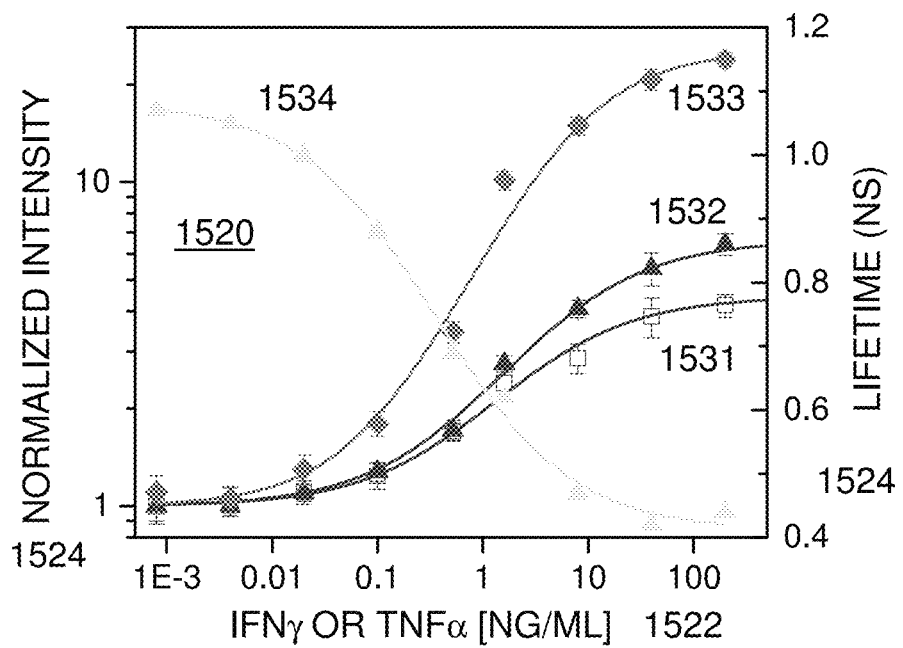

FIG. 15A and FIG. 15B are graphs 1500, 1520, respectively, that illustrate example fluorescence enhancement calibration curves for two cytokines, according to various embodiments. In graph 1500, the logarithmic horizontal axis 1502 indicates concentration of VEGF in nanograms per milliliter (ng/ml, 1 ng=$10^{-9}$ grams). The left side logarithmic vertical axis 1504 indicates intensity ratio, a dimensionless quantity; and the right side vertical axis 1505 indicates phase shift at 100 MHZ in degrees (which is proportional to lifetime). Graph 1500 displays three typical intensity calibration curves when using plasmonic substrates: directly based on intensity ratio and lifetime (expressed as phase shift) as trace 1513b and 1511; and also intensity after washing out the detection probe as trace 1513a; and on bare glass as trace 1513c for reference. Direct calibration curves (intensity and phase shift) are for no wash of detection probe (AF635-SA). The numbers show limits of detection (LOD) in ng/ml (baseline plus 2 standard deviations).

An advantage of using combined intensity and lifetime calibrations is large concentration dynamic range of more than 4 decades. This is because the sensitivity of each mode of calibration is different. A direct method of using phase measurement shown a trace 1511 displays the best sensitivity. This is because of favorable weighting of the short lifetime component from bound probes. For comparison, a standard method using a commercial glass substrate (need washing out) is included. It is clear that plasmonic substrates provide significantly better detection limits and the option of no washing. In a similar way several cytokine assays were tested (Table 2) and the results are satisfactory for use in assays. It is evident that the S/N ratio is excellent for plasmonic substrates allowing detection cytokines in the range of 10 pg/ml and better are expected for optimized assays when using dye-labeled antibodies as detection probes.

TABLE 2

Limit of detection (pg/ml) on MEF substrates

|  | TNFa | IFNg | IL-8 | IL-5 | VEGF | TNFa |
|---|---|---|---|---|---|---|
| Glass | 235 | 380 | 585 | 1256 | 2540 | 2650 |
| MEF washed | 25 | 30 | 15 | 36 | 90 | 210 |
| Direct intensity | 75 | 75 | 42 | 235 | 450 | 750 |
| Direct phase | 6 | 8 | 6 | 9 | 60 | 105 |
| Normal serum | 1-10 | 1-10 | >10 | 1-10 | ~180 | ~50 ng/ml |

The performance of MEF substrates is comparable to ELISA and ELISPOT using cell-free conditions. To carry out biochemical procedures and imaging, an adhesive silicon gasket was placed which served as a liquid reservoir for solution exchange and later for cell wells. The substrate was activated with capture antibodies immobilized using EDC/NHS procedure followed by blocking solution (5% BSA). The activated substrate was kept in culture media RPMI-1640 for 24 hrs in a $CO_2$ incubator at 37° C. Next, using dilutions of a mixture of recombinant TNFα and IFNγ (0.8 pg/ml-500 ng/ml) and the AF647 labeled detection antibodies (1 μg/ml each) were added to the wells. After 1 hour incubation, the wells were imaged with a FLIM instrument. The intensities were averaged over the entire spots and normalized to the baseline intensity (area outside the spots).

In graph 1520, the logarithmic horizontal axis 1522 indicates concentration of IFNg or TNFa in nanograms per milliliter. The left side logarithmic vertical axis 1524 indicates intensity ratio, a dimensionless quantity; and the right side vertical axis 1525 indicates lifetime in nanoseconds. Graph 1520 illustrates example calibration curves for two cytokines using Ab2-AF647. The fixed target includes two different capture antibodies that were spotted as 1 μl drops on different areas of the substrate. The assay was performed with a mixture of equimolar concentration of TNFα and IFNγ. The intensity curves are IFNγ direct trace 1531, TNFα direct trace 1532, and TNFα with washed probes trace 1533. The lifetime trace 1534 is for TNFa direct. LODs were determined as baseline plus 2 standard deviations; and were 60 pg/ml for traces 1531 and 1532, 16 pg/ml for trace 1533 and 6 pg/ml for trace 1534.

The lifetime parameter is more general than the phase shift because it can be applied to either time-domain or frequency-domain fluorometry. As shown here, lifetime modality is as highly sensitive as the phase shift measurements (FIG. 15A). In addition images were acquired after washing out dye-labeled antibodies, and a calibration curve generated for TNFα. FIG. 16A and FIG. 16B are images 1610 and 1620 that illustrate example spot quantification of two cytokines with and without washing, according to various embodiments. Image 1610 illustrates example direct (in presence of detection probes) active fluorescence spots 1611 for IFNγ and 1612 for TNFa at concentration of 0.51 ng/ml. Clearly there is a significant background signal seen between active spots that is also present over the active spots but does not prevent quantification of cytokine concentration at the active spots. Image 1620 illustrates example washed active fluorescence spots 1621 for IFNγ and 1622 for TNFa at concentration of 0.51 ng/ml after washing out.

The performance of the assay using various calibration modalities are characterized with LODs. The obtained sensitivities which are comparable with ELISA/ELISPOT indicate that the MEFspot method has great potential for sensing secreted proteins in cell culture environments.

Cytokine secretion is usually measured by ELISA in cell supernatants. This method works well if there is sufficient number of activated cells to produce cytokine concentration above the ELISA sensitivity limit, typically 10 pg/ml. The MEFspot quantifies the local concentration of cytokine(s) and thus, enables the direct measurement of cytokine secretion from a single cell. To demonstrate the capability of MEFspot for quantification of secretion in a cellular environment, human macrophages stimulated with macrophage colony stimulating factor (MCSF) for 12 hours were used for detection of secreted TNFα. In order to test real sensitivity, different cell numbers per well were used. The substrate was activated with a capture antibody (EDC/NHS protocol) and incubated with cells during stimulation. Cell supernatants were collected for subsequent ELISA measurements.

FIG. 17A, FIG. 17B and FIG. 17C are images that illustrate example spot quantification of fluorescence in the presence of cells for three concentrations of cells, respectively, according to various embodiments. FIG. 17A, FIG. 17B and FIG. 17C illustrate example quantification of secreted TNFa by macrophages stimulated with MCFS with different cell numbers of 30,000 per well, 10,000 per well, and 5,000 per well, respectively. Top image panel, i.e., images 1711, 1721 and 1731, shows cells stained with Calcein AM for the three different cell numbers. Bottom image panel, i.e., images 1712, 1722, 1732, shows the normalized fluorescence from bound Ab2-A647 after washing the unbound detection antibodies. Calcein AM excitation wavelength is 473 nm and emission wavelength is 525 nm to 530 nm. The AF647-antibody pair excitation wavelength is 640 nm and emission wavelength is >655 nm.

Figure 18A:
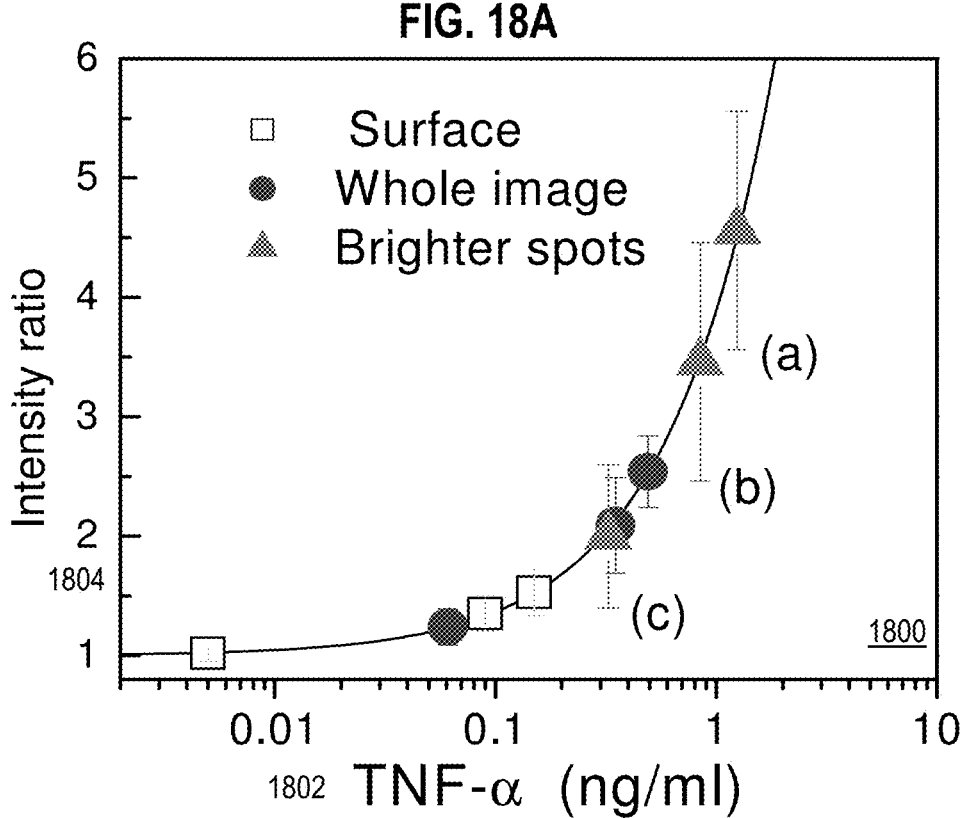
FIG. 18A is a graph that illustrates example calibration curve, according to an embodiment.

FIG. 18A is a graph 1800 that illustrates example calibration curve, according to an embodiment. The logarithmic horizontal axis 1802 indicates TNFα concentration in nanograms per milliliter. The linear vertical axis 1804 indicates intensity ratio, a dimensionless quantity. Three areas were considered for quantification of TNFα: (1) surface between cells, (2) whole image, and (3) bright spots. The intensities were normalized to the baseline (non-active area in the wells) correlated with calibration curve and plotted as symbols on the calibration curve. The supernatant was used as input to the ELISA process. Comparisons of readout from various areas and ELISA are depicted in FIG. 18B.

Figure 18B:
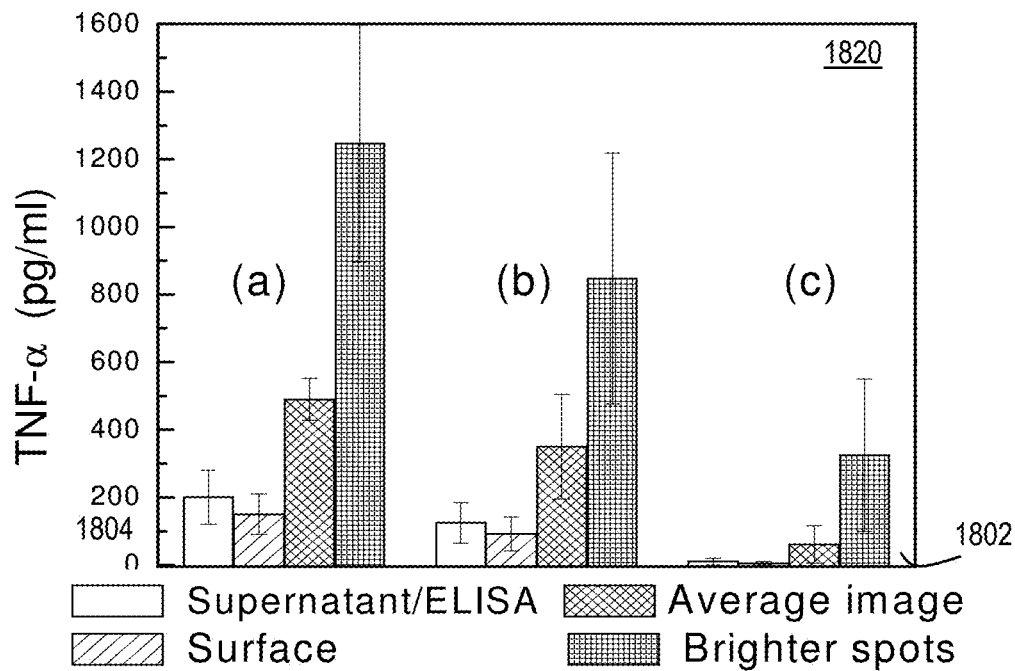
FIG. 18B is a graph that illustrates example advantages over a prior art approach, according to an embodiment.

FIG. 18B is a graph 1820 that illustrates example advantages over a prior art approach, according to an embodiment. The horizontal axis indicates different methods of quantification for the three cell counts depicted in FIG. 17A through FIG. 17C and designated (a), (b) and (c) in FIG. 18B. The vertical axis indicates the TNFα concentration deduced, in picograms per milliliter. The results are excellent. There is correlation between the supernatant and the surface-detected TNFα for all three cell counts. The average concentration decreases with a decreased number of cells. Production of secreted TNFα per active cell is larger for the high cell counts (a) that exhibit cell clusters than low cell counts (c) that exhibit primarily isolated cells, in agreement with other studies. These data illustrate the potential of MEFspot for immediate quantification with additional options compared to only post-experimental ELISA measurements, which may be not sensitive enough, e.g. for low cell counts (c). This experimental embodiment also confirmed the ability to elucidate information that cell clusters play crucial roles in the function of macrophages. It should be mentioned that MEFspot allows for imaging (or reimaging) of desired areas including selection of individual cells with high spatial resolution. In some embodiments, bright spots due to artifacts are rejected from analysis when lifetime analysis is included, because such artifacts often produce longer lifetimes than expected in solution.

Figure 19A:
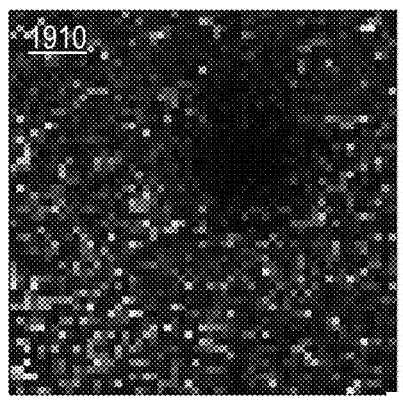
FIG. 19A, FIG. 19B and FIG. 19C are images that illustrate example real-time measurement of time-dependent secretion of a cytokine from a subset of cells in a population, according to various embodiments.
Figure 19B:
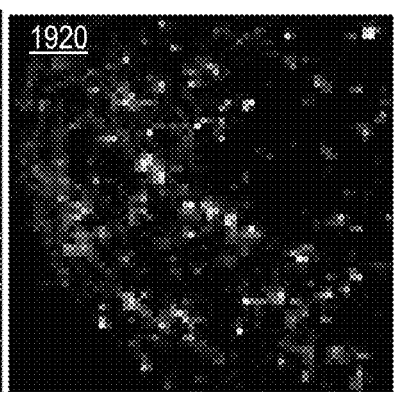
Figure 19C:
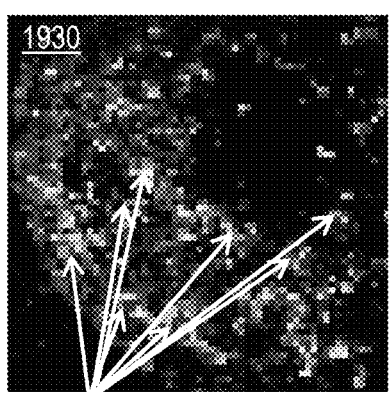

A new and unique feature of the MEFspot is the ability for real-time monitoring of protein secretion by cells. FIG. 19A, FIG. 19B and FIG. 19C are images 1910, 1920, 1930, respectively, that illustrate example real-time measurement of time-dependent secretion of a cytokine from a subset of cells in a population, according to various embodiments. The intensity gray scale is shown in bar 1902 for all three images. The highest intensities appear in image 1930 at the spots indicated by arrows 1932. These images show the result of monitoring the secretion of TNFα by macrophages activated with 30 ng/ml of lipopolysaccharide (LPS) over an eight hour period. In image 1910, cells are visualized with Calcein AM, for an image size of 2,000×2,000 μm². Image 1920 illustrates example intensity of Ab2-AF647 at one hour after stimulation; and, image 1930 illustrates example intensity at eight hours after stimulation.

Figure 19D:
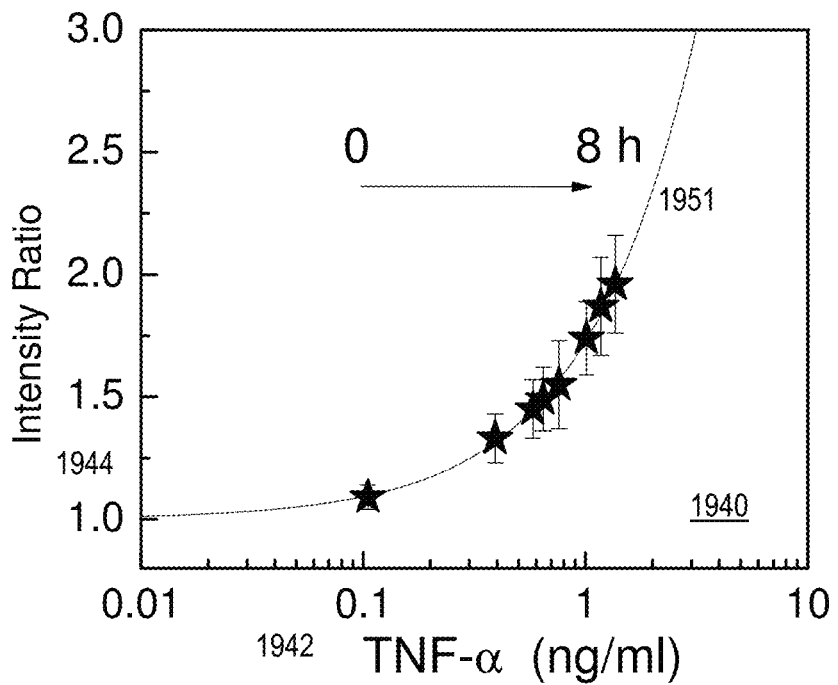
FIG. 19D is a graph that illustrates example use of calibration curve, according to an embodiment.
Figure 19E:
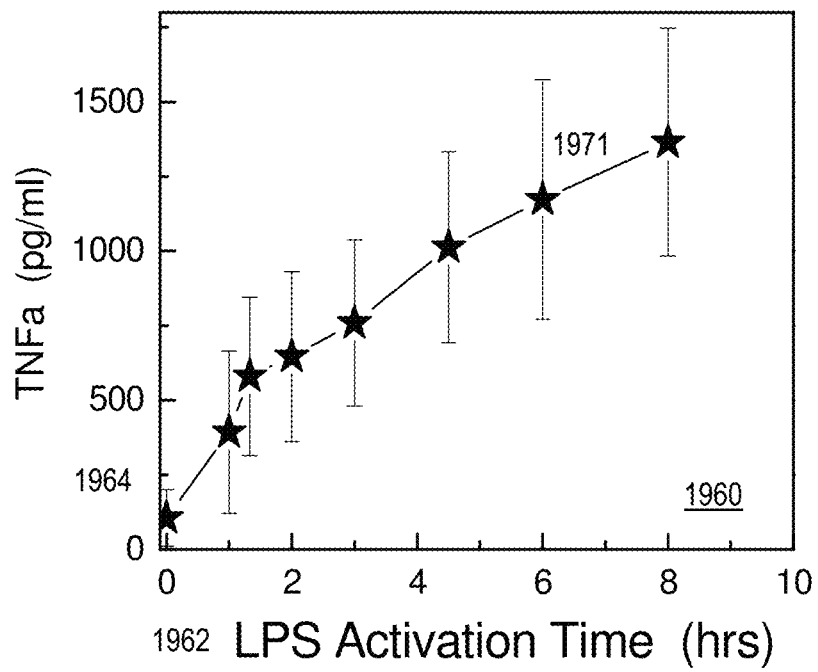
FIG. 19E is a graph that illustrates example measured time series of cytokine secretion, according to an embodiment.

FIG. 19D is a graph 1940 that illustrates example use of calibration curve 1951, according to an embodiment. The logarithmic horizontal axis 1942 indicates TNFa concentration in nanograms per milliliter. The vertical axis 1944 indicates intensity ratio, which is dimensionless. As time increases, the intensity ratio observations signified by points slide up the calibration curve 1951, as signified by the arrow indicating time after start of stimulation, thus indicating an increase in TNFa concentration with time. FIG. 19E is a graph 1960 that illustrates example measured time series of cytokine secretion, according to an embodiment. The horizontal axis 1962 indicates time of LPS activation in hours; and, the vertical axis 1964 indicates TNFa concentration in picograms per milliliter, now on a linear scale. Trace 1971 and observation points signified by stars are based on mapping the observed intensity values to concentration values using the calibration curve 1951 at each time point. Quantification was performed using average intensities from whole images and correlated to the calibration curve (in the presence of the detection probe). The large error bars (one standard deviation) in the effective TNFα concentration are due to large differences between bright spots and dim surface, which reflects variations in individual (or cell clusters) secretion and average supernatant.

A significant increase in cytokine production was observed over time. One can imagine a low number of active cells and monitor cytokine production by individual cells with high spatial resolution. High dye photostability in the presence of plasmonic substrates allows multiple time imaging without compromising the brightness of spots.

A phasor analysis of FLIM data is a very sensitive "fit-free" method to identify and distinguish different image areas based on the lifetime. The phasor plot is very convenient and powerful tool for analyzing FLIM images, and is gaining attention for cellular studies. The phasor plot is particularly attractive in MEFspot because of intrinsic changes in the lifetime of the detection probe upon binding to functionalized plasmonic substrates. Thus, cells secreting proteins can be visualized based on the lifetime values and provide an additional imaging tool to the biologist in interpreting usually complicated intensity images. The FLIM imager was used with experimental MEFspot assay.

Figure 20A:
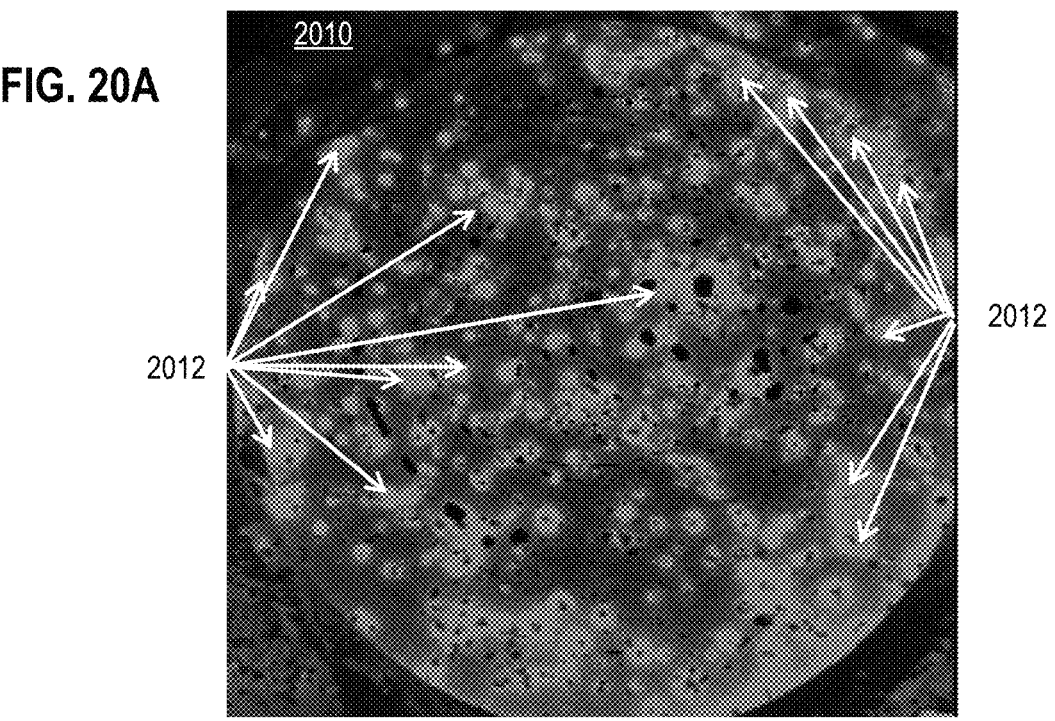
FIG. 20A, FIG. 20B and FIG. 20C, illustrate example enhanced analysis of fluorescence data from both intensity and lifetime measurements, according to an embodiment.
Figure 20C:
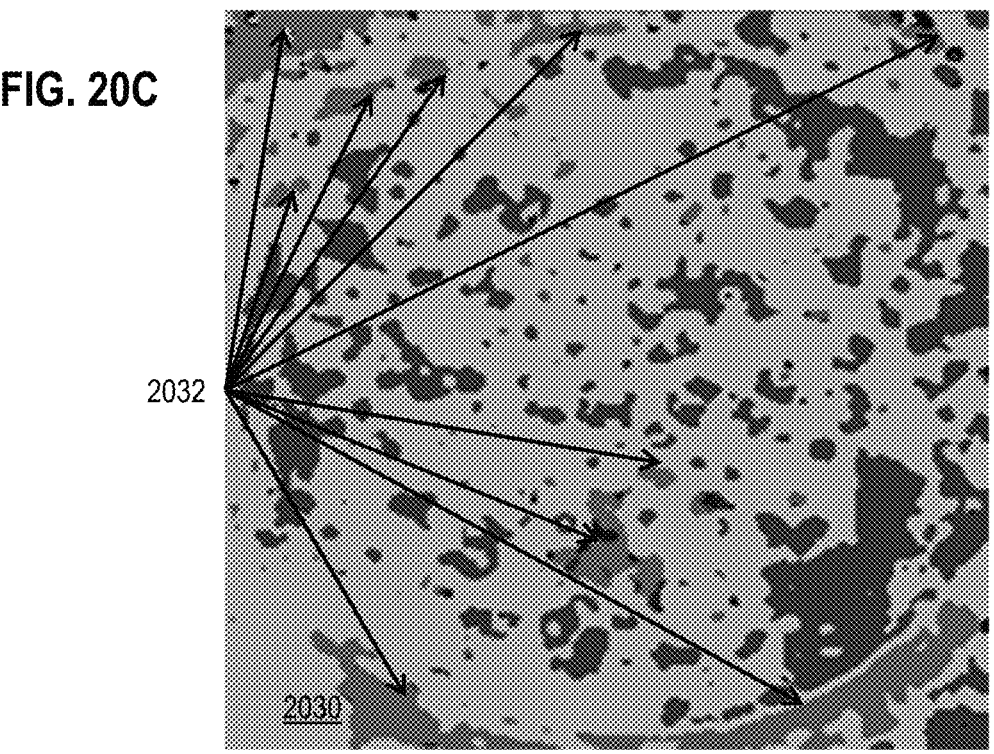
Figure 20B:
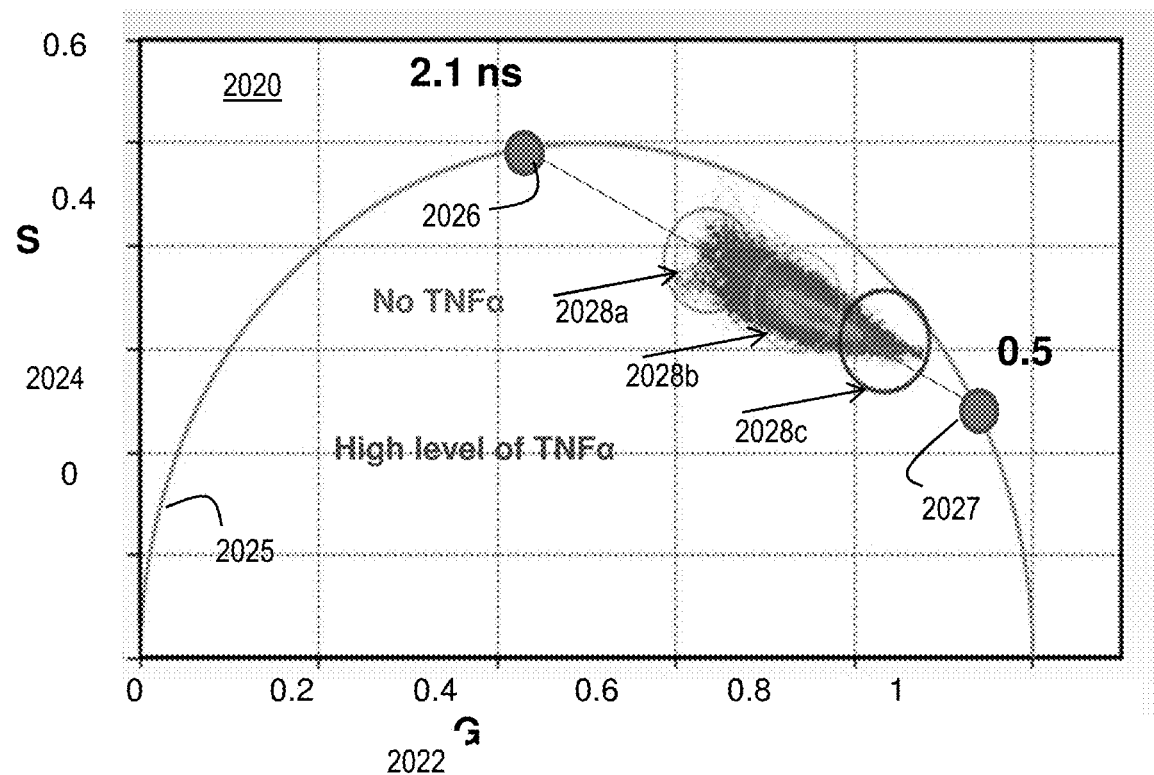

FIG. 20A, FIG. 20B and FIG. 20C, illustrate example enhanced analysis of fluorescence data from both intensity and lifetime measurements, according to an embodiment. FIG. 20A is an image 2010 that illustrates an example FLIM image of intensity of a MEFspot assay. Highest intensity spots are indicated by arrows 2012.

Each pixel in the image 2010 is also associated with a lifetime measurement used to generate a phasor plot. FIG. 20B is a graph 2020 that illustrates an example phasor plot. The horizontal axis 2022 indicates a G coordinate of the lifetime information, which is dimensionless; and the vertical axis 2024 indicates an S coordinate of the lifetime information, also dimensionless. The S and G coordinates are the Fourier sine (S) and cosine (G) transforms related to lifetime components, amplitudes and modulation frequency. Pixels with single exponential decay lifetimes are located on the semicircle 2025. For bi-exponential decays, the locations of the two component phasors are along the line joining the two lifetime points defined by the fractional contribution of each component ($f_i$) in the observed total intensity. Every pixel of the intensity image is transformed into a point (pixel) in the phasor plot with coordinates S and G defined by the lifetime data for the pixel. The pixel locations are on the line between two single exponential lifetimes depicted as 2.1 ns, point 2026, and 0.5 ns, point 2027. Three regions on the phasor plot are selected (2028a, 2028b and 2028c). The long lifetime pixels (2028a) indicate the area of only free detection probe in solution. The short lifetime pixels (2028c) show areas that correspond to high level of TNF-α secretion. The middle lifetime pixels (2028b) shows intermediate average lifetime of 1.25 ns.

FIG. 20C is an image 2030 that illustrates results of the phasor classification mapped to the spatial arrangement in the assay. The long lifetime pixels indicated by arrows 2032 locate the areas of only free detection probe in solution. The short lifetime pixels are the remaining dark areas on the image 2030. The middle lifetime pixels are bright areas in image 2030. The phasor plot allows identification of spots (cells, cell clusters) generated by secreted TNFα in a heterogeneous intensity image.

In some embodiments, simultaneous imaging of cytokine secretion and cell phenotype is performed. The performance of plasmonic substrates are determined using HEK293T cells transiently transfected with Toll-like receptor (TLR) fused with Cerulen fluorescent protein (Cer). Conventional methods of transient transfection produce cell population heterogeneous with respect to expression of transfected protein. A model cell population is created in which the expression of a function-defining protein in a single cell is visualized simultaneously with protein secretion by the same cell. Exogenous expression of TLR in HEK293T cells promotes a strong cellular response to TLR agonists; e.g., the cells that express TLR produce cytokines in agonist-dependent manner. TLR4-Cer and TLR2-Cer are used in various embodiments. TLR4 recognizes bacterial lipopolysaccharides (LPS) and TLR2 senses bacterial lipoproteins (synthetic lipoproteins are commercially available).

Figure 21:
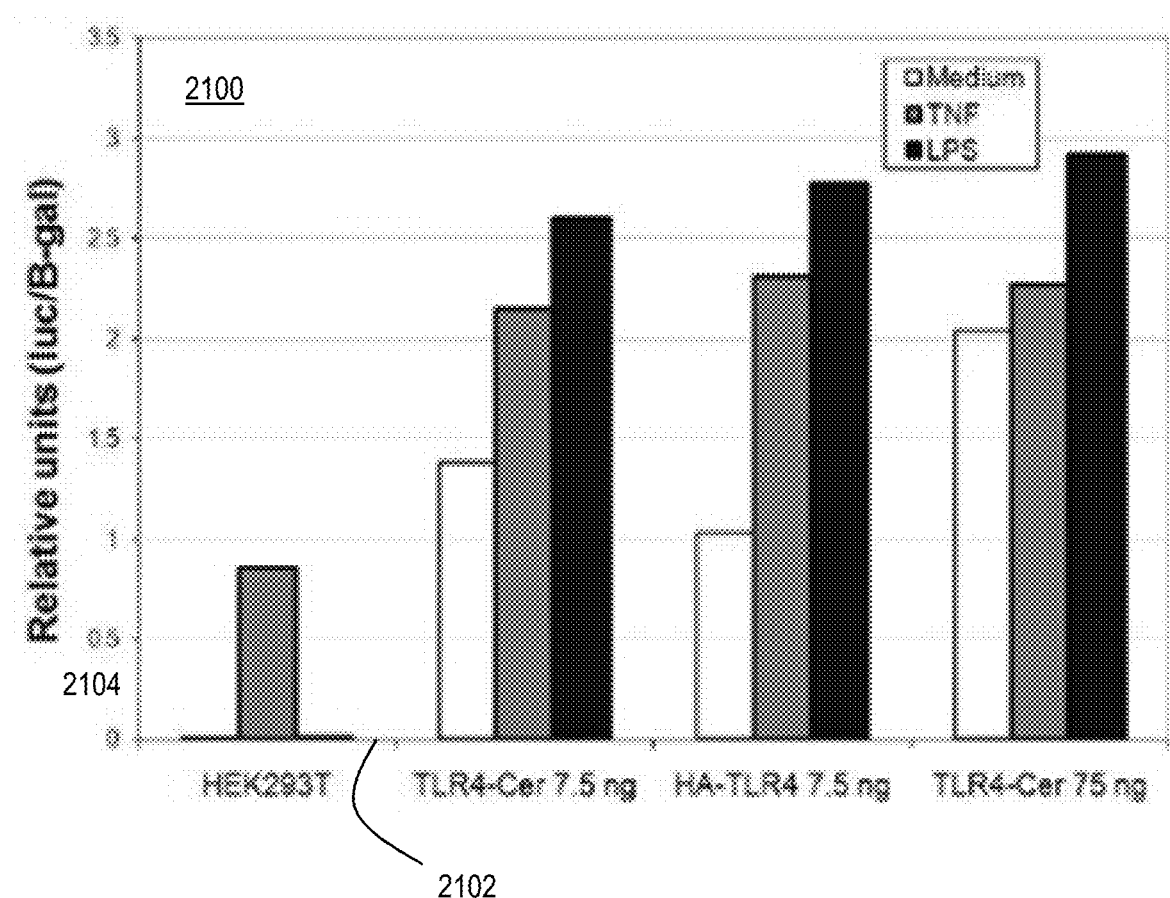
FIG. 21 is a graph that illustrates example correlation of phenotype with profile of secreted cytokines, according to an embodiment.

FIG. 21 is a graph 2100 that illustrates example correlation of phenotype with profile of secreted cytokines, according to an embodiment. The horizontal 2102 axis indicates cell and tag; and, the vertical axis 2104 indicates intensity in relative units. TLR4-Cer fusion protein retains intact signaling properties in HEK293T cells stimulated with LPS. HA-tagged TLR4 and Cer-tagged TLR4 induce NF-κB reporter similarly. These results demonstrate that transfection of HEK293T cells with TLR4-Cer and stimulated with LPS induces NF-κB similarly to the TLR4 HA-tagged through the N terminus. In some embodiments, TLR expression in a single cell is imaged by fluorescence microscopy and used as the phenotype-defining marker for the population of cytokine-secreting cells such as TNFα, IFNγ and dual TNFα/IFNγ. In an example embodiment, a 443 nm laser is used for Cer; and a 532 nm laser is used for IFNγ and a 640 nm laser is used for TNFα.

To correlate cell phenotype with cell function at the single cell level in some embodiments, TLR-Cer-transfected cells are stimulated by a TLR agonist or treated by the TLR agonist in the presence of TLR antagonist. This model permits a demonstration of the feasibility of simultaneous detection of a protein marker expressed in cell and the cytokine secretion profile of this cell in a heterogeneous cell population. To further characterize the capabilities of MEFspot, the level of TLR expression in a single cell is correlated quantitatively with the rate and kinetics of cytokine production by the same cell.

In some embodiments, MEFspot detects dual cytokine secreting cells immediately ex vivo, which would be highly significant to the field of cytokine biology. While early in vitro studies characterized highly polarized helper T-cell subsets capable of producing their signature cytokines (e.g., Th2 make IL-4, IL-5, IL-13), it is becoming appreciated that these cells maintain dynamic plasticity, especially during inflammatory responses in vivo. For example, increased numbers of Th2 cells that are also capable of producing TNFα or IFNγ were correlated with enhanced allergic lung inflammation. Furthermore, a variety of tumor cell types including pancreatic cancer and colorectal cancer can produce IL-4 or IL13. In addition, tumor infiltrating T-cells can produce IL-4 and other cytokines which can protect tumor cells from apoptosis while production of IFNγ promotes antitumor responses.

An example embodiment is directed to the production of IL-4, and IL-13 in combination with other cytokines because of the relationship between double producers and the phenotype of allergic lung inflammation. Detection of IL-4 is critical because it is signature Th2 cytokine and is usually expressed less abundantly than most other cytokines and also is consumed in culture. Thus absent or low IL-4 expression in an otherwise Th2-dominated response might reflect the technical difficulties of IL-4 detection rather than true IL-4⁻ Th2 cells. Cytokine pairs that are examined by MEFspot in various embodiments include single IL-4, IL-5, and IL-13 and dual IL-4/IL-5, IL-4/IL-13, IL-4/IFN-γ, IL-5/IFN-γ, and IL-13/IFN-γ. Cytokines, antibodies, and dye labeling kits are supplied by several vendors.

For example, in some embodiments, secretion of dual cytokines from lymph node and lung cells are imaged as specified above. For this experiment, an in vivo model is used, which results in the development of dual producing T-cells. In vivo-primed CD4+ T cells are transferred into RAG2$^{-/-}$ and γ$_c$xRAG2$^{-/-}$ mice, and are sensitized and challenged with a model allergen (ovalbumin). Lymph nodes and lungs are collected 48 hours after the last challenge; and lymph node cells harvested by mechanical disruption. Lung tissue from each mouse is digested with 150 U/ml Collagenase and 10 U/ml DNase for 1 hour at 37° C. Lymph node and lung cells are incubated on the MEFspot plates immediately ex vivo. They are tested either untreated, as a control, or stimulated on the plate by adding PMA/ionomycin. Expression of IL-4/IL-5, IL-4/IL-13, IL-4/IFN-γ, IL-5/IFN-γ, and IL-13/IFN-γ in these cells are imaged using the MEFspot method. These experiments are performed in the presence and absence of dye conjugated anti-CD4 antibody to distinguish CD4+ T-cells in the complex cell population. This is especially informative in the lung cells samples where T-cells are in the minority and other cell types such as mast cells and basophils can produce IL-4 and IL-13.

This embodiment can validate the MEFspot method to detect double cytokine producers in complex cell populations derived ex vivo from an inflammatory environment. It is anticipated that MEFspot offers a simple biochemical procedure using live cells. Importantly this approach allows time-dependent monitoring of the secreted cytokines and a relatively easy way for quantification of secretion. These new features enhance the approach for cellular analysis and reveal more information on changes in cytokine secretion profiles of T-cells as a result of changes in their environment (RAG2$^{-/-}$ and γ$_c$xRAG2$^{-/-}$). In other embodiments, this approach is utilized to address cytokine secretion by cells in other types of inflammatory environments and in a complex tumor microenvironment. In some embodiments, the results are compared to the benchmark technologies, intracellular cytokine staining (ICCS) and ELISA.

2.3 Assays for Cell Surface Receptors.

Figure 24A:
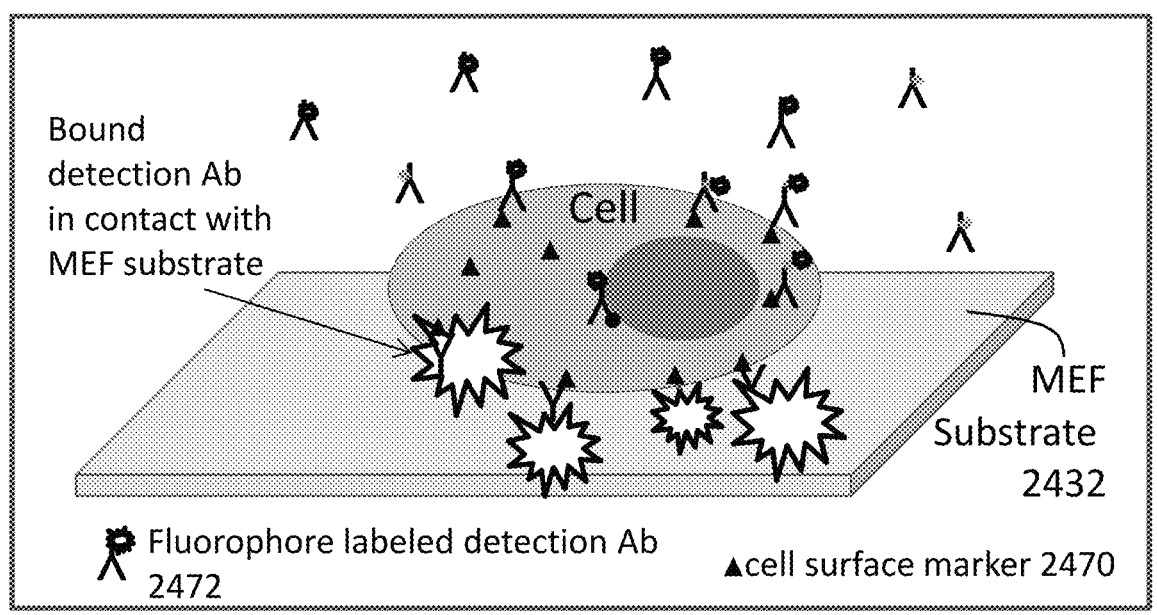
FIG. 24A and FIG. 24B are block diagrams that illustrate example assay for cell surface analytes, such as receptors, using a plasmonic substrate without bioactive layer, according to an embodiment
Figure 24B:
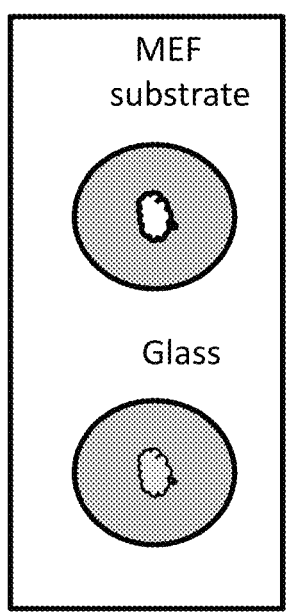

FIG. 24A and FIG. 24B are block diagrams that illustrate example assay for cell surface analytes, such as receptors, using a plasmonic substrate without bioactive layer, according to an embodiment. In this embodiment, gravity or natural cell adhesion to a surface, or both, is used instead of a bioactive layer to ensure close proximity between receptors on the bottom surface of the cell and a plasmonic substrate. This offers the advantage of a much simpler preparation of the substrate and simpler operation of the assay.

As with changes in secretion of cytokines, the expression of cell surface receptors are hallmarks of the activation of T cells by interacting tumor cells. While there are several methods routinely used for detection of secretion and cell surface protein expression, there is a lack of method to visualize T cell activation on a single cell level. T cells represent a qualitatively and functionally heterogeneous population of cells with the ability to produce different cytokines, chemokines and activation/suppression markers. The expression of various proteins on the T cell's surface are important indicators of effector function. Furthermore, the activation status of a T cell can be characterized be the co-expression of inhibitory markers such as PD-1, Lag-3, TIM-3, TIGIT while the ability for T cells to infiltrate tumors is characterized by the expression of chemokine receptors (CCR1, CCR5, CXCR3). Here is proposed novel multicolor fluorescence imaging technology for simultaneous or alternative visualization of protein secretion and expression of cell-surface markers.

Cell-surface expressed receptors (cell markers) 2470 are the analytes; and, are tagged with dye-labeled detection antibodies (Ab) 2472. A dramatic increase in intensity occurs because of the proximity of the dye-labeled antibodies to the MEF substrate 2432 surface via cell adhesion, with contact precipitated by gravity. The MEFspot principles are depicted schematically in FIG. 24A. FIG. 24B depicts enhanced intensity of detection molecules bound to the cell resurface receptors on the MEF substrate versus the glass substrate. Detection dye-labeled antibodies bound to specific cell receptors generate bright spots (cells) when cell settles on the MEF surface, e.g., due to gravity or adhesion or both. In some embodiments, one or more cells of a particular type are bound to the substrate surface by using surface immobilized antibodies specific to cell-surface receptors, e.g., cluster differentiation proteins, as a bioactive functionalized layer. This approach will facilitate using the MEFspot method for weakly adherent or non-adherent cells. The spots intensity correlates with the surface density of markers. The fraction of active cells can be quantified and ascribed to different phenotypes. For multicolor MEFspot embodiments, multiple capture antibodies and multicolor multiple detection antibodies are used.

In some embodiments, simultaneous secretions and receptors are visualized. One embodiment for development and optimization of multicolor imaging technology is performed using three panels of multiple-protein assays and their combinations for simultaneous detection of cytokines secretion and cell-surface markers on a single cell level—called a multi cytokines/phenotype assay (MCPA). Multilayer MEF substrates are fabricated using our multi-target magnetron sputtering system (Hummer RF6.6 from Anatech, USA) capable of fabrication of 10 glass slides at a time. Fabrication protocol and substrate performance testing are already established, as described above.

The three protein panels are the following. Panel A (cell functions with secreted cytokines): IL-2, IFN-γ, TNF-α; Panel B (phenotypes with cell-surface chemokine receptors): CXCR3 (CD183), CCR1 (CD191), CCR5 (CD195); and Panel C (phenotypes with cell-surface markers): PD-1, Lag-3 (CD223), TIM-3 (CD366) and TIGIT. Potential 10-colors were identified for design of multicolor MEFspot which allows for simultaneous detection of secreted cytokines (Panel A) and cell-surface expressed markers (Panel B or C). Table 3 shows initial selections of 7 colors panel based on availability of dye-conjugated antibodies. Three additional colors are available such as Pacific Blue (laser 405 nm), and use of tandem probes such as PE/Cy5 and PE/Cy7 (laser 473 nm).

TABLE 3

Multicolor panels for simultaneous imaging of cytokines (A) and cell-surface markers (B and C).

| A: Secreted Cytokines Laser 405 nm | | | B: Cell Surface Chemokines Laser 475 and 640 nm | | | C: Cell surface Markers Laser 475 and 640 nm | | | | Additional 475 405 nm | |
|---|---|---|---|---|---|---|---|---|---|---|---|
| TNF-α | IFN-γ | IL-2 | CCR1 CD191 | CCR5 CD195 | CXCR3 CD183 | PD-1 | Lag-3 CD223 | TIGIT | TIM-3 CD366 | CD8 | |
| BV421 | BV605 | BV711 | AF488 | PE | APC | FITC | PE | APC | AF750 | PE/Cy5,/ Cy7 | PB |

Multicolor MEFspot can be easily customized for detection of other sets of secreted/surface expressed proteins. Expected limit of detection (LOD) for 3-colors soluble cytokines is in the range of 1-10 pg/ml. It is anticipated that intensities of spots will remain stable for extended time up to 4 days because of typically high affinities of antibodies for cytokine assays. Sensitivity for cell surface densities is anticipated of about 1,000-2,000 receptors/cell. Cell culture media and cellular conditions will assure that the protocol can be easily transferred for T cell assays.

In some embodiments, a cell or cell type is bound to surface of the substrate by using surface immobilized antibodies specific to cell-surface receptors, e.g., certain cluster differentiation (CD) proteins. This approach will facilitate using the MEFspot method for weak or non-adherent cells. In such embodiments the substrate is functionalized with biomolecules with affinity for proteins different from the analyte. The purpose of the bioactive molecule in such embodiments is to bind the cell to the surface, the labeled receptors or secretions in the vicinity of the bound cell are enhanced by proximity of the cell to the substrate.

Figure 25:
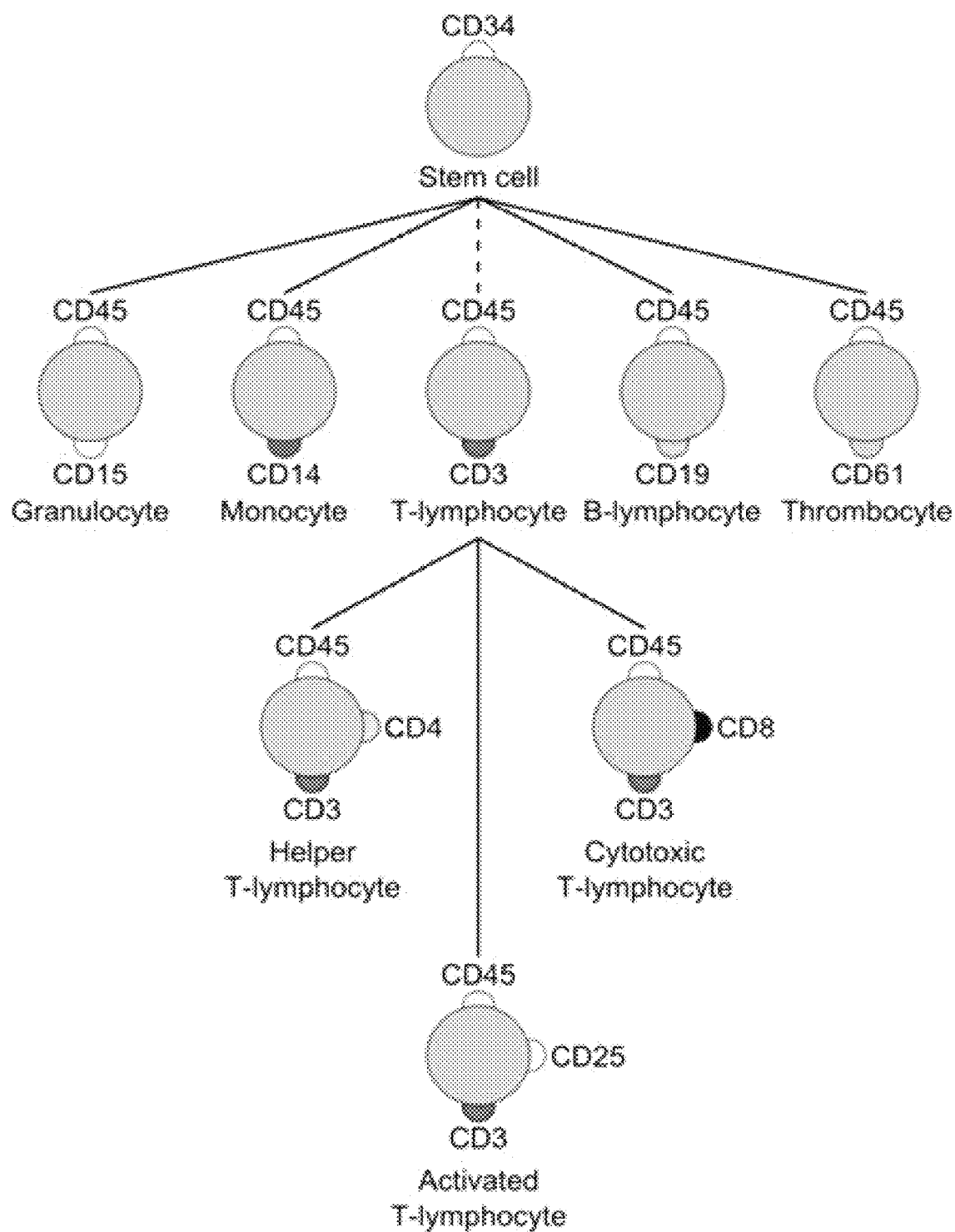
FIG. 25 is a block diagram that illustrates example hierarchy of cell types of the immune system distinguished by cell surface receptors as markers, according to an embodiment.

FIG. 25 is a block diagram that illustrates example hierarchy of cell types of the immune system distinguished by cell surface receptors as markers, according to an embodiment. FIG. 25 illustrates differentiation of cells of the adaptive immune system by their surface receptors. Individual surface receptors are identified by their Cluster of Differentiation (CD) numbering convention. The surface receptors that serve as unique markers for the different cell types are underlined in Table 4.

TABLE 4

Cluster of Differentiation (CD) as cell-surface markers for cell immunophenotyping

| Type of Cell | CD markers |
|---|---|
| Stem cells | CD34+, CD31−, CD117 |
| All leukocyte groups | CD45+ |
| Granulocyte | CD45+, CD11b, CD15+, CD24+, CD114+, CD182+, |
| Monocyte | CD4, CD45+, CD14+, CD114+, CD11a, CD11b, CD91+, CD16+ |

TABLE 4-continued

Cluster of Differentiation (CD) as cell-surface markers for cell immunophenotyping

| Type of Cell | CD markers |
| --- | --- |
| T lymphocyte | CD45+, CD3+ |
| T helper cell | CD45+, CD3+, CD4+ |
| T regulatory cell | CD4, CD25, Foxp3 |
| Cytotoxic T cell | CD45+, CD3+, CD8+ |
| B lymphocyte | CD45+, CD19+, CD20+, CD24+, CD38, CD22 |
| Thrombocyte | CD45+, CD61+ |
| Natural killer cell | CD16+, CD56+, CD3−, CD31, CD30, CD38 |

2.4 Assays for Cell-Cell Interactions.

In some embodiments, cell-cell interactions are assayed based on secretions in the vicinity of two different cell types identified by their surface receptors. In such embodiments, the sample comprises a plurality of different types of living cells and the analyte is a plurality of analytes including a different surface receptor to distinguish each type of living cell of the plurality of different types and at least one secretion from one type of living cell from the plurality of living types. All such analytes can be separately labeled and detected using multiple different fluorophores.

The capability of MEFspot to visualize the effect of one type of cells on another is extremely important for cell type therapies, e.g., interaction of immune cells with cancer cells. To Applicants' knowledge there is no other method to do this as effective as MEFspot. The most frequent way is to get information from indirect measurements: ELISA for looking of changes in secretion profiles for supernatant (not know how really individual cells are interacting), Flow cytometry by seeing changes in cytokine production and cell surface markers but no information on relative localization of interacting cells.

In an example embodiment, one evaluates how the interaction between T cells and cancer cells impact T cell activation and function. MEF-MCPA offers an advantage of being able to assess spatial localization of interacting cells as well as to determine change in the cytokine secretion profile (or quantity) for T cells that do and do not interact with tumor cells. The hierarchical tree of FIG. 25 is constructed for distinguishing T cell populations; and is used to determine which are in physical contact, in close proximity, and those which are well separated from tumor cells. Furthermore, one can also visualize tumor cell lysis and correlate cytokine production as well as the expression of exhaustion markers (or chemokine receptors) by neighboring T cells. This can be achieved by combining of images of selected fluorophore colors with expected overlapping phenotype spots confined within physical areas of cells with images having more diffusive spots generated by secreted cytokines. In such embodiments, an 8 color assay is used to visualize cytokine secretions (3 colors), expression of cell-surface markers (3 colors for panel A and 4 for panel B), and visualize T-cell (CD8) with additional color as listed in Table 3.

Figure 26A:
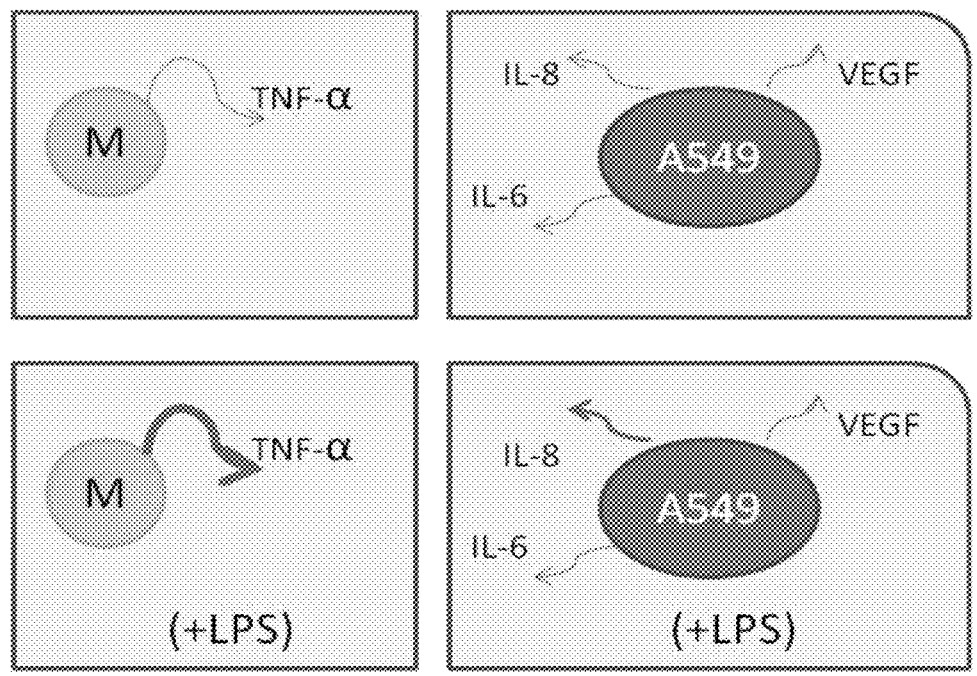
FIG. 26A is a block diagram that illustrates an example measurement of secretions from two different types of cells under two different stimulation conditions, when measured separately, according to an embodiment.
Figure 26B:
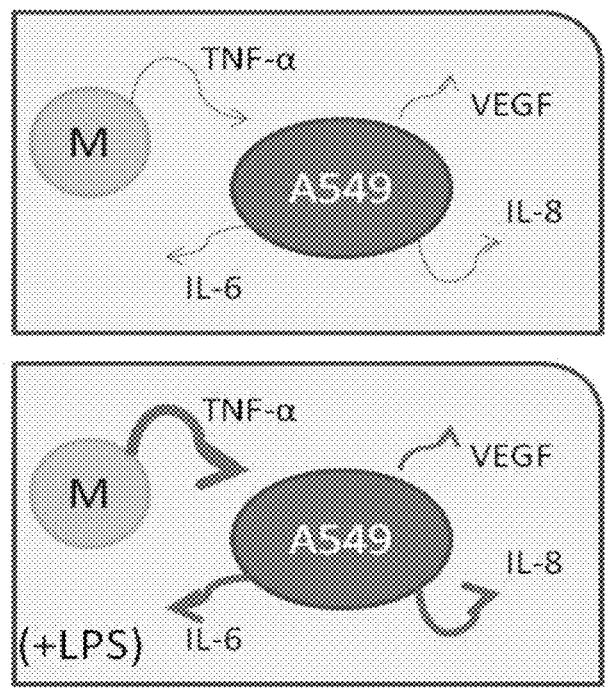
FIG. 26B is a block diagram that illustrates an example measurement of secretions from two different types of cells interacting under two different stimulation conditions, according to an embodiment.

FIG. 26A is a block diagram that illustrates an example measurement of secretions from two different types of cells under two different stimulation conditions, when measured separately, according to an embodiment. FIG. 26B is a block diagram that illustrates an example measurement of secretions from two different types of cells interacting under two different stimulation conditions, according to an embodiment. In these figures, the amount of detected secretion is indicated by the thickness of the arrow associated with each secreted protein, with thicker arrows indicating larger amounts.

Here is illustration of effect of macrophages (M) on small lung cancer cells (A549). First, profiles of secreted cytokines are imaged in mono cultures with and without stimulant, lipopolysaccharide (LPS). As shown in FIG. 26A, when stimulated separately (bottom panels), the M cell secretes enhanced amounts of TNF-a, while the A549 cell secretes only enhanced amount of IL-8 compared to non-stimulated cells (top panels).

Next cells are co-cultured and again imaged with and without stimulant. As shown in FIG. 26B (top panel), the M and A549 cells secrete cytokines in cells co-culture with the same amounts as in cell monocultures (FIG. 26A top panel). When stimulant is added to cells co-culture, it directly stimulates enhanced secretion of TNF-a from M cells. Higher concentration of TNF-a in co-culture activates A549 cells resulting in enhanced secretion of cytokine VEGF, IL-6, IL8. This demonstrates the effect of drugs that stimulate one type of cell may also cause the first type of cell to affect the function of another type of cell. FIG. 26B illustrate cell-cell interaction in general where function and phenotype of one type of cells affect function and phenotype of another type of cell. As an example, modified T cells as one type and cancer cells as another type of cells can be envisioned. Secreted and cell-surface expressed receptors on T cells may lead to alter cancer cell function, damage or apoptosis. Looking on the secretions and cell surface markers of both types of cells and their relative locations within co-culture likely provides very valuable information on the potency of modified T cells for killing tumor cells.

3. COMPUTER HARDWARE OVERVIEW

Figure 22:
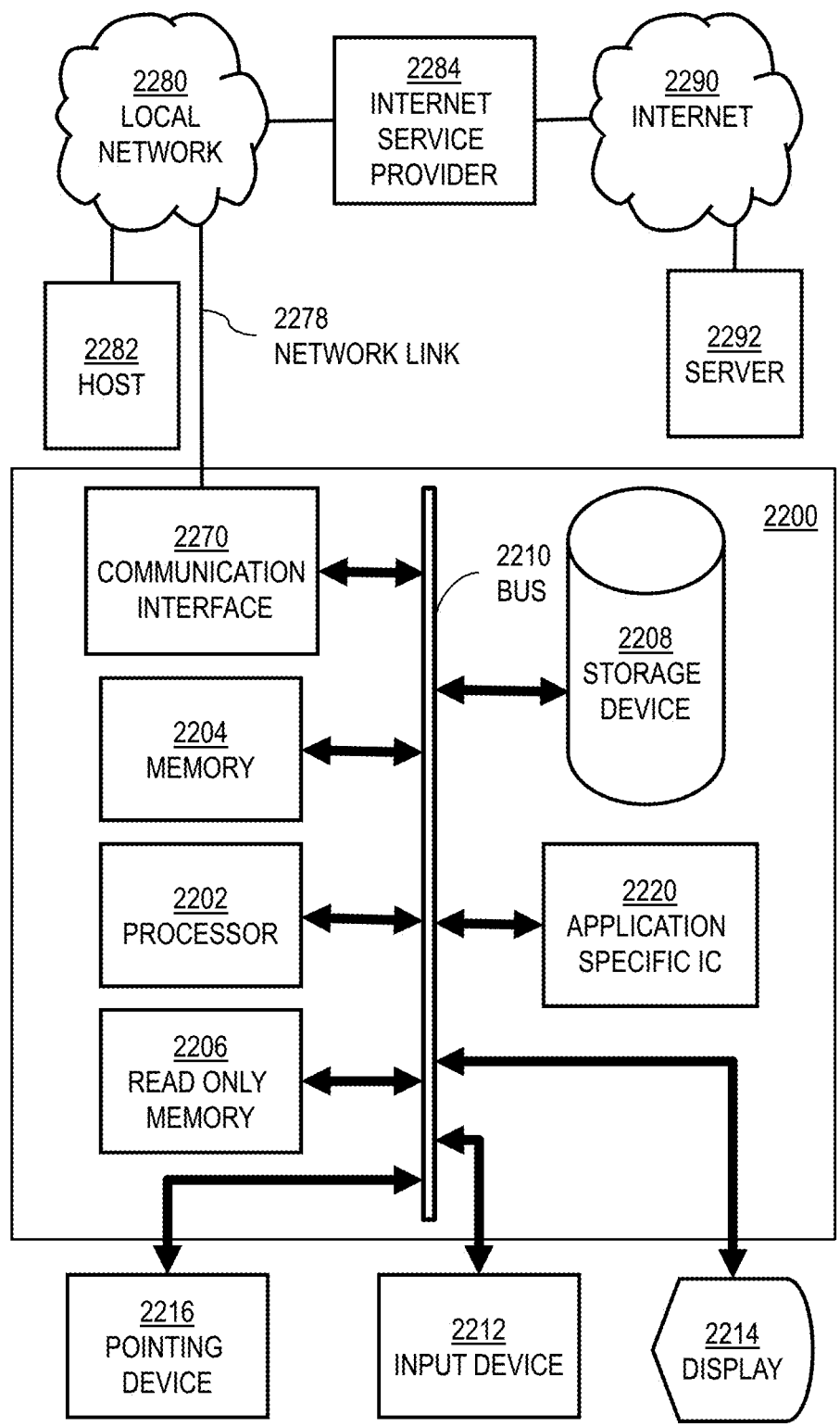
FIG. 22 is a block diagram that illustrates a computer system upon which an embodiment of the invention may be implemented.

FIG. 22 is a block diagram that illustrates a computer system 2200 upon which an embodiment of the invention may be implemented. Computer system 2200 includes a communication mechanism such as a bus 2210 for passing information between other internal and external components of the computer system 2200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 2200, or a portion thereof, constitutes a means for performing one or more steps of one or more methods described herein.

A sequence of binary digits constitutes digital data that is used to represent a number or code for a character. A bus 2210 includes many parallel conductors of information so that information is transferred quickly among devices coupled to the bus 2210. One or more processors 2202 for processing information are coupled with the bus 2210. A processor 2202 performs a set of operations on information. The set of operations include bringing information in from the bus 2210 and placing information on the bus 2210. The set of operations also typically include comparing two or more units of information, shifting positions of units of information, and combining two or more units of information, such as by addition or multiplication. A sequence of operations to be executed by the processor 2202 constitute computer instructions.

Computer system 2200 also includes a memory 2204 coupled to bus 2210. The memory 2204, such as a random access memory (RAM) or other dynamic storage device, stores information including computer instructions. Dynamic memory allows information stored therein to be changed by the computer system 2200. RAM allows a unit of information stored at a location called a memory address to be stored and retrieved independently of information at neighboring addresses. The memory 2204 is also used by the processor 2202 to store temporary values during execution of computer instructions. The computer system 2200 also includes a read only memory (ROM) 2206 or other static storage device coupled to the bus 2210 for storing static information, including instructions, that is not changed by the computer system 2200. Also coupled to bus 2210 is a non-volatile (persistent) storage device 2208, such as a magnetic disk or optical disk, for storing information, including instructions, that persists even when the computer system 2200 is turned off or otherwise loses power.

Information, including instructions, is provided to the bus 2210 for use by the processor from an external input device 2212, such as a keyboard containing alphanumeric keys operated by a human user, or a sensor. A sensor detects conditions in its vicinity and transforms those detections into signals compatible with the signals used to represent information in computer system 2200. Other external devices coupled to bus 2210, used primarily for interacting with humans, include a display device 2214, such as a cathode ray tube (CRT) or a liquid crystal display (LCD), for presenting images, and a pointing device 2216, such as a mouse or a trackball or cursor direction keys, for controlling a position of a small cursor image presented on the display 2214 and issuing commands associated with graphical elements presented on the display 2214.

In the illustrated embodiment, special purpose hardware, such as an application specific integrated circuit (IC) 2220, is coupled to bus 2210. The special purpose hardware is configured to perform operations not performed by processor 2202 quickly enough for special purposes. Examples of application specific ICs include graphics accelerator cards for generating images for display 2214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 2200 also includes one or more instances of a communications interface 2270 coupled to bus 2210. Communication interface 2270 provides a two-way communication coupling to a variety of external devices that operate with their own processors, such as printers, scanners and external disks. In general the coupling is with a network link 2278 that is connected to a local network 2280 to which a variety of external devices with their own processors are connected. For example, communication interface 2270 may be a parallel port or a serial port or a universal serial bus (USB) port on a personal computer. In some embodiments, communications interface 2270 is an integrated services digital network (ISDN) card or a digital subscriber line (DSL) card or a telephone modem that provides an information communication connection to a corresponding type of telephone line. In some embodiments, a communication interface 2270 is a cable modem that converts signals on bus 2210 into signals for a communication connection over a coaxial cable or into optical signals for a communication connection over a fiber optic cable. As another example, communications interface 2270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 2270 sends and receives electrical, acoustic or electromagnetic signals, including infrared and optical signals, that carry information streams, such as digital data.

The term computer-readable medium is used herein to refer to any medium that participates in providing information to processor 2202, including instructions for execution. Such a medium may take many forms, including, but not limited to, non-volatile media, volatile media and transmission media. Non-volatile media include, for example, optical or magnetic disks, such as storage device 2208. Volatile media include, for example, dynamic memory 2204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 2202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 2202, except for carrier waves and other signals.

Logic encoded in one or more tangible media includes one or both of processor instructions on a computer-readable storage media and special purpose hardware, such as ASIC 2220.

Network link 2278 typically provides information communication through one or more networks to other devices that use or process the information. For example, network link 2278 may provide a connection through local network 2280 to a host computer 2282 or to equipment 2284 operated by an Internet Service Provider (ISP). ISP equipment 2284 in turn provides data communication services through the public, world-wide packet-switching communication network of networks now commonly referred to as the Internet 2290. A computer called a server 2292 connected to the Internet provides a service in response to information received over the Internet. For example, server 2292 provides information representing video data for presentation at display 2214.

The invention is related to the use of computer system 2200 for implementing the techniques described herein. According to one embodiment of the invention, those techniques are performed by computer system 2200 in response to processor 2202 executing one or more sequences of one or more instructions contained in memory 2204. Such instructions, also called software and program code, may be read into memory 2204 from another computer-readable medium such as storage device 2208. Execution of the sequences of instructions contained in memory 2204 causes processor 2202 to perform the method steps described herein. In alternative embodiments, hardware, such as application specific integrated circuit 2220, may be used in place of or in combination with software to implement the invention. Thus, embodiments of the invention are not limited to any specific combination of hardware and software.

The signals transmitted over network link 2278 and other networks through communications interface 2270, carry information to and from computer system 2200. Computer system 2200 can send and receive information, including program code, through the networks 2280, 2290 among others, through network link 2278 and communications interface 2270. In an example using the Internet 2290, a server 2292 transmits program code for a particular application, requested by a message sent from computer 2200, through Internet 2290, ISP equipment 2284, local network 2280 and communications interface 2270. The received code may be executed by processor 2202 as it is received, or may be stored in storage device 2208 or other non-volatile storage for later execution, or both. In this manner, computer system 2200 may obtain application program code in the form of a signal on a carrier wave.

Various forms of computer readable media may be involved in carrying one or more sequence of instructions or data or both to processor 2202 for execution. For example, instructions and data may initially be carried on a magnetic disk of a remote computer such as host 2282. The remote computer loads the instructions and data into its dynamic memory and sends the instructions and data over a telephone line using a modem. A modem local to the computer system 2200 receives the instructions and data on a telephone line and uses an infra-red transmitter to convert the instructions and data to a signal on an infra-red a carrier wave serving as the network link 2278. An infrared detector serving as communications interface 2270 receives the instructions and data carried in the infrared signal and places information representing the instructions and data onto bus 2210. Bus 2210 carries the information to memory 2204 from which processor 2202 retrieves and executes the instructions using some of the data sent with the instructions. The instructions and data received in memory 2204 may optionally be stored on storage device 2208, either before or after execution by the processor 2202.

Figure 23:
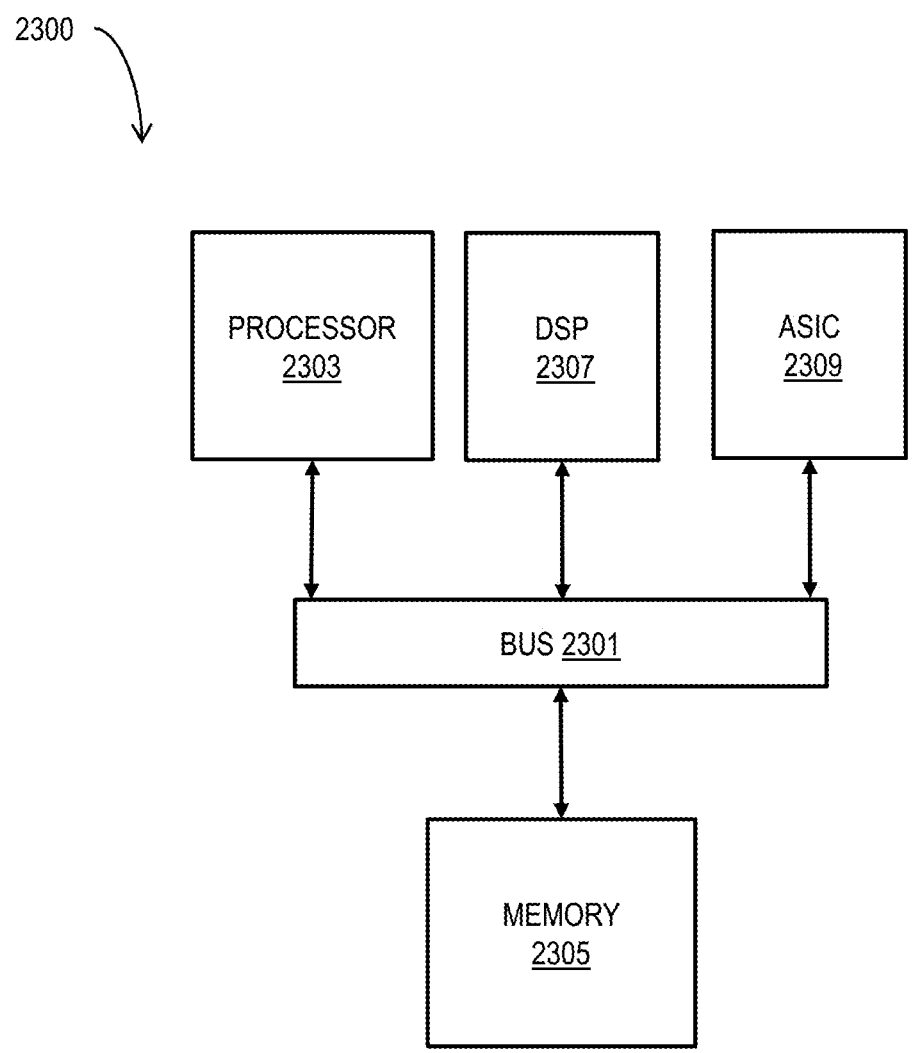
FIG. 23 illustrates a chip set upon which an embodiment of the invention may be implemented.

FIG. 23 illustrates a chip set 2300 upon which an embodiment of the invention may be implemented. Chip set 2300 is programmed to perform one or more steps of a method described herein and includes, for instance, the processor and memory components described with respect to FIG. 22 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 2300, or a portion thereof, constitutes a means for performing one or more steps of a method described herein.

In one embodiment, the chip set 2300 includes a communication mechanism such as a bus 2301 for passing information among the components of the chip set 2300. A processor 2303 has connectivity to the bus 2301 to execute instructions and process information stored in, for example, a memory 2305. The processor 2303 may include one or more processing cores with each core configured to perform independently. A multi-core processor enables multiprocessing within a single physical package. Examples of a multi-core processor include two, four, eight, or greater numbers of processing cores. Alternatively or in addition, the processor 2303 may include one or more microprocessors configured in tandem via the bus 2301 to enable independent execution of instructions, pipelining, and multithreading. The processor 2303 may also be accompanied with one or more specialized components to perform certain processing functions and tasks such as one or more digital signal processors (DSP) 2307, or one or more application-specific integrated circuits (ASIC) 2309. A DSP 2307 typically is configured to process real-world signals (e.g., sound) in real time independently of the processor 2303. Similarly, an ASIC 2309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 2303 and accompanying components have connectivity to the memory 2305 via the bus 2301. The memory 2305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 2305 also stores the data associated with or generated by the execution of one or more steps of the methods described herein.

4. EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

5. REFERENCES

1. Giakos G. C., Meehan K. and Tuma M. (2002). Exploitation of Enhanced Fluorescence via Cross-Coupling Principles Toward the Design of an Optical Integrated Thin-Film Sensor for Nanotechnology and Biomedical Applications. *IEEE Trans. Instr. Measurem.* 51 (5):970-975.
2. Matveeva E., Gryczynski Z., Malicka J., Gryczynski I., Lakowicz J. R. (2004). Metal-enhanced fluorescence immunoassays using total internal reflection and silver island-coated surfaces. *Anal. Biochem,* 334:303-311.

3. Matveeva E. G., Gryczynski I., Barnett A., Leonenko Z., Lakowicz J. R., Gryczynski Z. (2007). Metal particle-enhanced fluorescent immunoassays on metal mirrors. *Anal. Biochem.* 361: 239-245.

4. Zhang J., Malicka J., Gryczynski I. and Lakowicz J. R. (2005). Surface-enhanced fluorescence of fluorescein-labeled oligonucleotides capped on silver nanoparticles, *J. Phys. Chem. B* 109:7643-7648.

5. Szmacinski H., Smith D. S., Hanson M. A., Kostov Y., Lakowicz J. R., Rao G. (2008). A novel method for monitoring monoclonal antibody production during cell culture. *Bioeng. Biotechnol.* 100: 448-457.

6. Szmacinski H., Murtaza Z., Lakowicz J. R. (2010). Time-resolved fluorometric method for one-step immunoassays using plasmonic nanostructures. *J. Phys. Chem. C* 114: 7236-7241

What is claimed is:

1. A method comprising:
   providing a plasmonic substrate comprising
      a layer configured as a mirror to reflect light,
      a layer of dielectric material disposed on the mirror wherein a thickness of the dielectric layer is greater than about 20 nanometers, and
      a layer of metal nanoparticles disposed on the layer of dielectric material;
   providing a reagent comprising a detection molecule for a particular analyte;
   determining a calibration curve that relates concentration of the particular analyte to at least one of intensity or lifetime of fluorescent emissions at the plasmonic substrate in response to incident light for a plurality of known concentrations of the particular analyte mixed with the reagent,
   contacting a sample comprising a cell and the reagent to the plasmonic substrate;
   obtaining measurements of at least one of intensity or lifetime of fluorescent emissions at the plasmonic substrate in contact with the cell and reagent in response to the incident light; and
   determining a concentration of the particular analyte in a vicinity of the cell directly from the calibration curve and the measurements.

2. A method as recited in claim 1, wherein the sample and reagent are not rinsed from the substrate before obtaining the measurements.

3. A method as recited in claim 1, wherein the sample comprises a living cell and the analyte is a surface receptor on the living cell.

4. A method as recited in claim 3, wherein the analyte is a cytokine receptor, a chemokine receptor, a cluster differentiation protein, or an inhibitory marker, or some combination.

5. A method as recited in claim 1, further comprising;
   obtaining second measurements of at least one of intensity or lifetime of fluorescent emissions at the plasmonic substrate in contact with the cell and reagent in response to the incident light at a later time; and
   determining a concentration of the particular analyte in the cell at the later time directly from the calibration curve and the second measurements.

6. A method as recited in claim 1 wherein:
   the particular analyte comprises a plurality of different analytes; and
   the fluorescent emissions comprise emissions in a corresponding plurality of emission wavelength bands associated with a corresponding plurality of detection molecules comprising a corresponding plurality of different fluorophores.

7. A method as recited in claim 6, wherein the plurality of different analytes consists of about ten different analytes.

8. A method as recited in claim 3, further comprising determining viability of the living cell based on the concentration of the particular analyte.

9. A method as recited in claim 3, further comprising determining phenotype of the living cell based on the concentration of the particular analyte.

10. A method as recited in claim 1, wherein the layer of metal nanoparticles has an optical density below about 1.

11. A method as recited in claim 1, wherein a thickness of the dielectric layer is in a range from about 20 nanometers to about 80 nanometers.

12. A method as recited in claim 1, wherein a thickness of the dielectric layer is in a range from about 25 nanometers to about 80 nanometers.

13. A method as recited in claim 1, wherein a thickness of the dielectric layer is selected to maximize fluorescent enhancement for a particular fluorophore in the detection molecule.

14. A method as recited in claim 6, wherein the sample comprises a plurality of different types of living cells and the plurality of different analytes includes a different surface receptor to distinguish each type of living cell of the plurality of different types and at least one secretion from one type of living cell from the plurality of living types.

15. A method as recited in claim 14, wherein the plurality of different types of living cells are co-cultured.

16. A method as recited in claim 15, further comprising comparing an amount of the at least one secretion from the plurality of different types of living cells co-cultured with an amount of the at least one secretion when the plurality of different cell types are cultured separately to determine cell-cell interactions.

17. A method as recited in claim 1, wherein plasmonic substrate is functionalized with bioactive molecules that bind to a receptor of a cell wherein the receptor is different from the analyte.

18. An apparatus comprising:
    a source of incident light,
    an optical coupler configured to direct incident light onto a plasmonic substrate in contact with a mixture of a reagent and a sample comprising a cell, wherein the reagent comprises a detection molecule for the particular analyte and the plasmonic substrate comprises
       a layer configured as a mirror to reflect light,
       a layer of dielectric material disposed on the mirror wherein a thickness of the dielectric layer is greater than about 20 nanometers, and
       a layer of metal nanoparticles disposed on the layer of dielectric material;
    a detector configured to measure fluorescent emissions from the plasmonic substrate;
    at least one processor; and
    at least one memory including one or more sequences of instructions, the at least one memory and the one or more sequences of instructions configured to, with the at least one processor, cause the apparatus to perform at least the following,
       determining a calibration curve that relates concentration of a particular analyte to at least one of intensity or lifetime of fluorescent emissions at the plasmonic substrate in response to the incident light for a plurality of known concentrations of the particular analyte mixed with the reagent; a determining a concentration of the particular analyte in a vicinity of the cell directly from the calibration curve and measurements of at least one of intensity or lifetime of fluorescent emissions at the functionalized substrate in contact with the cell and reagent in response to the incident light; and operating a device based on the concentration of the particular analyte.

19. A method as recited in claim 1, wherein the plasmonic substrate is configured for resonance within a silica layer for selected wavelengths.

* * * * *